United States Patent
Cortez, Jr. et al.

(10) Patent No.: US 11,065,120 B2
(45) Date of Patent: Jul. 20, 2021

(54) METHOD AND APPARATUS FOR CARDIAC PROCEDURES

(71) Applicants: University of Maryland, Baltimore, Baltimore, MD (US); Harpoon Medical, Inc., Baltimore, MD (US)

(72) Inventors: Felino V. Cortez, Jr., Bowie, MD (US); James S. Gammie, Stevenson, MD (US); Peter Wilson, Killingworth, CT (US); Luke Anthony Zanetti, Parkton, MD (US); Julie Marie Etheridge, Ellicott City, MD (US); Stephen Cournane, Severn, MD (US)

(73) Assignees: University of Maryland, Baltimore, Baltimore, MD (US); Harpoon Medical, Inc., Baltimore, MD (US)

(*) Notice: Subject to any disclaimer, the term of this patent is extended or adjusted under 35 U.S.C. 154(b) by 130 days.

(21) Appl. No.: 16/167,069

(22) Filed: Oct. 22, 2018

(65) Prior Publication Data

US 2019/0117401 A1 Apr. 25, 2019

Related U.S. Application Data

(60) Provisional application No. 62/576,364, filed on Oct. 24, 2017.

(51) Int. Cl.
  *A61F 2/24* (2006.01)
  *A61B 17/04* (2006.01)
  (Continued)

(52) U.S. Cl.
  CPC ........ *A61F 2/2466* (2013.01); *A61B 17/0469* (2013.01); *A61B 17/0482* (2013.01);
  (Continued)

(58) Field of Classification Search
  CPC ............ A61B 17/0401; A61B 17/0466; A61B 17/0469; A61B 17/0482;
  (Continued)

(56) References Cited

U.S. PATENT DOCUMENTS 3,131,957 A 5/1964 Must
3,752,516 A 8/1973 Mumma
(Continued)

FOREIGN PATENT DOCUMENTS

DE 912619 C 5/1954
EP 0791330 A3 11/1997
(Continued)

OTHER PUBLICATIONS

Alfieri, O. el al., "The double-orifice technique in mitral valve repair: a +A198:A225simple solution for complex problems," (2001) J. Thorne. Cardiovasc. Surg., 122(4):674-681.
(Continued)

*Primary Examiner* — Wade Miles
*Assistant Examiner* — Mohammed S Adam
(74) *Attorney, Agent, or Firm* — David S. Barnhill; Chang & Hale

(57) ABSTRACT

Described herein are methods and apparatus for approximating targeted tissue using locking sutures. The locking sutures can be configured to receive suture ends that are interweaved through portions of the locking sutures. In a pre-deployment configuration, a locking suture can slide along suture tails and can be positioned at a target location within a target region. Once a desired position and/or tension is achieved, the locking suture can be transitioned to a post-deployment configuration where the locking suture constricts around the suture tails to inhibit relative movement between the suture tails and the locking suture.

20 Claims, 77 Drawing Sheets

(51) Int. Cl.
　　　*A61B 17/00*　　(2006.01)
　　　*A61B 90/00*　　(2016.01)
(52) U.S. Cl.
　　　CPC .......... *A61B 17/0485* (2013.01); *A61B 90/03* (2016.02); *A61B 2017/00243* (2013.01); *A61B 2017/00783* (2013.01); *A61B 2017/0406* (2013.01); *A61B 2017/048* (2013.01); *A61B 2017/0417* (2013.01); *A61B 2017/0464* (2013.01); *A61B 2017/0474* (2013.01); *A61B 2017/0477* (2013.01); *A61B 2017/0496* (2013.01); *A61B 2090/08021* (2016.02); *A61F 2/2445* (2013.01); *A61F 2/2457* (2013.01)
(58) Field of Classification Search
　　　CPC .... A61B 2017/0409; A61B 2017/0474; A61B 2017/0496; A61F 2/2466
　　　See application file for complete search history.

(56) References Cited

U.S. PATENT DOCUMENTS

| | | |
|---|---|---|
| 4,403,797 A | 9/1983 | Ragland, Jr. |
| 4,662,376 A | 5/1987 | Belanger |
| 4,807,625 A | 2/1989 | Singleton |
| 5,144,961 A | 9/1992 | Chen et al. |
| 5,147,316 A | 9/1992 | Castillenti |
| 5,312,423 A | 5/1994 | Rosenbiuth et al. |
| 5,391,176 A | 2/1995 | de la Torre |
| 5,405,352 A | 4/1995 | Weston |
| 5,454,821 A | 10/1995 | Harm et al. |
| 5,472,446 A | 12/1995 | de la Torre |
| 5,507,754 A | 4/1996 | Green et al. |
| 5,527,323 A | 6/1996 | Jervis et al. |
| 5,554,184 A | 9/1996 | Machiraju |
| 5,626,614 A | 5/1997 | Hart |
| 5,643,293 A | 7/1997 | Kogasaka et al. |
| 5,681,331 A | 10/1997 | de la Torre et al. |
| 5,716,368 A | 2/1998 | de la Torre et al. |
| 5,727,569 A | 3/1998 | Benetti et al. |
| 5,728,109 A | 3/1998 | Schulze et al. |
| 5,746,752 A | 5/1998 | Burkhart |
| 5,769,862 A | 6/1998 | Kammerer et al. |
| 5,797,928 A | 8/1998 | Kogasaka |
| 5,824,065 A | 10/1998 | Gross |
| 5,931,868 A | 8/1999 | Gross |
| 5,957,936 A | 9/1999 | Yoon et al. |
| 5,971,447 A | 10/1999 | Steck, III |
| 6,010,531 A | 1/2000 | Donlon et al. |
| 6,074,417 A | 6/2000 | Peredo |
| 6,269,819 B1 | 8/2001 | Oz et al. |
| 6,332,893 B1 | 12/2001 | Mortier et al. |
| 6,562,051 B1 | 5/2003 | Bolduc et al. |
| 6,626,930 B1 | 9/2003 | Allen et al. |
| 6,629,534 B1 | 10/2003 | St. Goar et al. |
| 6,752,810 B1 | 6/2004 | Gao et al. |
| 6,840,246 B2 | 1/2005 | Downing |
| 6,860,890 B2 * | 3/2005 | Bachman ........... A61B 17/0469 606/148 |
| 6,921,408 B2 | 7/2005 | Sauer |
| 6,940,246 B2 | 9/2005 | Mochizuki et al. |
| 6,978,176 B2 | 12/2005 | Lattouf |
| 6,991,635 B2 | 1/2006 | Takamoto et al. |
| 6,997,950 B2 | 2/2006 | Chawla |
| 7,112,207 B2 | 9/2006 | Allen et al. |
| 7,291,168 B2 | 11/2007 | Macoviak et al. |
| 7,294,148 B2 | 11/2007 | McCarthy |
| 7,309,086 B2 | 12/2007 | Carrier |
| 7,316,706 B2 | 1/2008 | Bloom et al. |
| 7,373,207 B2 | 5/2008 | Lattouf |
| 7,431,692 B2 | 10/2008 | Zollinger et al. |
| 7,513,908 B2 | 4/2009 | Lattouf |
| 7,534,260 B2 | 5/2009 | Lattouf |
| 7,608,091 B2 | 10/2009 | Goldfarb et al. |
| 7,618,449 B2 | 11/2009 | Tremulis et al. |
| 7,632,308 B2 | 12/2009 | Loulmet |
| 7,635,386 B1 | 12/2009 | Gammie |
| 7,666,196 B1 | 2/2010 | Miles |
| 7,744,609 B2 | 6/2010 | Allen et al. |
| 7,837,727 B2 | 11/2010 | Goetz et al. |
| 7,871,368 B2 | 1/2011 | Zollinger et al. |
| 7,871,433 B2 | 1/2011 | Lattouf |
| 7,959,650 B2 | 6/2011 | Kaiser et al. |
| 8,029,518 B2 | 10/2011 | Goldfarb et al. |
| 8,029,565 B2 | 10/2011 | Lattouf |
| 8,043,368 B2 | 10/2011 | Crabtree |
| 8,147,542 B2 | 4/2012 | Maisano et al. |
| 8,226,711 B2 | 7/2012 | Mortier et al. |
| 8,241,304 B2 | 8/2012 | Bachman |
| 8,252,050 B2 | 8/2012 | Maisano et al. |
| 8,292,884 B2 | 10/2012 | Levine et al. |
| 8,303,622 B2 | 11/2012 | Alkhatib |
| 8,333,788 B2 | 12/2012 | Maiorino |
| 8,382,829 B1 | 2/2013 | Call et al. |
| 8,439,969 B2 | 5/2013 | Gillinov et al. |
| 8,454,656 B2 | 6/2013 | Tuval |
| 8,465,500 B2 | 6/2013 | Speziali |
| 8,475,525 B2 | 7/2013 | Maisano et al. |
| 8,500,800 B2 | 8/2013 | Maisano et al. |
| 8,608,758 B2 | 12/2013 | Singhatat et al. |
| 8,663,278 B2 | 3/2014 | Mabuchi et al. |
| 8,771,296 B2 | 7/2014 | Nobles et al. |
| 8,828,053 B2 | 9/2014 | Sengun et al. |
| 8,652,213 B2 | 10/2014 | Gammie et al. |
| 8,888,791 B2 | 11/2014 | Jaramillo et al. |
| 8,940,008 B2 | 1/2015 | Kunis |
| 9,131,884 B2 | 9/2015 | Holmes et al. |
| 9,192,287 B2 | 11/2015 | Saadat et al. |
| 2002/0013571 A1 | 1/2002 | Goldfarb et al. |
| 2003/0023254 A1 | 1/2003 | Chiu |
| 2003/0094180 A1 | 5/2003 | Benetti |
| 2003/0105519 A1 | 6/2003 | Fasol et al. |
| 2003/0120264 A1 | 6/2003 | Lattouf |
| 2003/0120341 A1 | 6/2003 | Shennib et al. |
| 2004/0044365 A1 | 3/2004 | Bachman |
| 2004/0093023 A1 | 5/2004 | Allen et al. |
| 2004/0199183 A1 | 10/2004 | Oz et al. |
| 2005/0004667 A1 | 1/2005 | Swinford et al. |
| 2005/0019735 A1 | 1/2005 | Demas |
| 2005/0075654 A1 | 4/2005 | Kelleher |
| 2005/0149067 A1 | 7/2005 | Takemoto et al. |
| 2005/0149093 A1 | 7/2005 | Pokorney |
| 2005/0154402 A1 | 7/2005 | Sauer et al. |
| 2005/0216036 A1 | 9/2005 | Nakao |
| 2005/0216077 A1 | 9/2005 | Mathis et al. |
| 2005/0261710 A1 | 11/2005 | Sakamoto et al. |
| 2005/0267493 A1 | 12/2005 | Schreck et al. |
| 2006/0030866 A1 | 2/2006 | Schreck |
| 2006/0100698 A1 | 5/2006 | Lattouf |
| 2006/0111739 A1 | 5/2006 | Staufer et al. |
| 2006/0167541 A1 | 7/2006 | Lattouf |
| 2006/0190030 A1 | 8/2006 | To et al. |
| 2006/0282088 A1 | 12/2006 | Ryan |
| 2007/0001857 A1 | 1/2007 | Hartmann et al. |
| 2007/0049952 A1 | 3/2007 | Weiss |
| 2007/0055292 A1 | 3/2007 | Ortiz et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0149995 A1 | 6/2007 | Quinn et al. |
| 2007/0197858 A1 | 8/2007 | Goldfarb et al. |
| 2007/0213582 A1 | 9/2007 | Zollinger et al. |
| 2007/0270793 A1 | 11/2007 | Lattouf |
| 2008/0004597 A1 | 1/2008 | Lattouf et al. |
| 2008/0009888 A1 | 1/2008 | Ewers et al. |
| 2008/0065203 A1 | 3/2008 | Khalapyan |
| 2008/0140093 A1 | 6/2008 | Stone et al. |
| 2008/0167714 A1 | 7/2008 | St. Goar et al. |
| 2008/0188893 A1 * | 8/2008 | Selvitelli ........... A61B 17/0401 606/232 |
| 2008/0228223 A1 | 9/2008 | Alkhatib |
| 2008/0249504 A1 | 10/2008 | Lattouf et al. |
| 2008/0269781 A1 | 10/2008 | Funamura et al. |

(56) References Cited

U.S. PATENT DOCUMENTS

| | | |
|---|---|---|
| 2009/0005863 A1 | 1/2009 | Goetz et al. |
| 2009/0043153 A1 | 2/2009 | Zollinger et al. |
| 2009/0105729 A1 | 4/2009 | Zentgraf |
| 2009/0105751 A1 | 4/2009 | Zentgraf |
| 2009/0276038 A1 | 11/2009 | Tremulis et al. |
| 2010/0023056 A1 | 1/2010 | Johansson et al. |
| 2010/0023117 A1 | 1/2010 | Yoganathan et al. |
| 2010/0023118 A1 | 1/2010 | Medlock et al. |
| 2010/0042147 A1 | 2/2010 | Janovsky et al. |
| 2010/0210899 A1 | 6/2010 | Schankereli |
| 2010/0174297 A1 | 7/2010 | Speziali |
| 2010/0179574 A1 | 7/2010 | Longoria et al. |
| 2010/0249809 A1 | 9/2010 | Singhatat et al. |
| 2010/0298929 A1* | 11/2010 | Thornton ............. A61F 2/2445 623/2.1 |
| 2010/0298930 A1 | 11/2010 | Orlov |
| 2011/0015476 A1 | 1/2011 | Franco |
| 2011/0022083 A1 | 1/2011 | DiMatteo et al. |
| 2011/0022084 A1 | 1/2011 | Sengun et al. |
| 2011/0028995 A1 | 2/2011 | Miraki et al. |
| 2011/0029071 A1 | 2/2011 | Zlotnick et al. |
| 2011/0060407 A1 | 3/2011 | Ketai et al. |
| 2011/0106106 A1 | 5/2011 | Meier et al. |
| 2011/0144743 A1 | 6/2011 | Lattouf |
| 2011/0264208 A1 | 10/2011 | Duffy et al. |
| 2011/0270278 A1 | 11/2011 | Overes et al. |
| 2011/0288637 A1 | 11/2011 | De Marchena |
| 2011/0307055 A1 | 12/2011 | Goldfarb et al. |
| 2012/0004669 A1 | 1/2012 | Overes et al. |
| 2012/0143215 A1 | 6/2012 | Corrao et al. |
| 2012/0150223 A1 | 6/2012 | Manos et al. |
| 2012/0179184 A1 | 7/2012 | Orlov |
| 2012/0184971 A1 | 7/2012 | Zentgraf et al. |
| 2012/0203072 A1 | 8/2012 | Lattouf et al. |
| 2012/0226294 A1 | 9/2012 | Tuval |
| 2012/0226349 A1 | 9/2012 | Tuval et al. |
| 2013/0018459 A1 | 1/2013 | Maisano et al. |
| 2013/0035757 A1 | 2/2013 | Zentgraf et al. |
| 2013/0253641 A1 | 9/2013 | Lattouf |
| 2013/0282059 A1 | 10/2013 | Ketai et al. |
| 2013/0345749 A1 | 12/2013 | Sullivan et al. |
| 2014/0031926 A1 | 1/2014 | Kudlik et al. |
| 2014/0039607 A1 | 2/2014 | Kovach |
| 2014/0067052 A1 | 3/2014 | Chau et al. |
| 2014/0114404 A1 | 4/2014 | Gammie et al. |
| 2014/0214152 A1 | 7/2014 | Bielefeld |
| 2014/0243968 A1 | 8/2014 | Padala |
| 2014/0364938 A1 | 12/2014 | Longoria et al. |
| 2015/0032127 A1 | 1/2015 | Gammie et al. |
| 2015/0045879 A1 | 2/2015 | Longoria et al. |
| 2016/0317144 A1 | 11/2016 | Popovici et al. |
| 2016/0317304 A1* | 11/2016 | Spence ............. A61B 17/0401 |

FOREIGN PATENT DOCUMENTS

| | | |
|---|---|---|
| JP | 2013517110 A | 5/2013 |
| WO | 2004037463 A1 | 5/2004 |
| WO | 2006127509 A2 | 11/2006 |
| WO | 2007119057 A1 | 10/2007 |
| WO | 2008013869 A2 | 1/2008 |
| WO | 2007100268 A3 | 10/2008 |
| WO | 2008124110 A3 | 12/2008 |
| WO | 2008143740 A3 | 2/2009 |
| WO | 2006078694 A3 | 4/2009 |
| WO | 2009081396 A2 | 7/2009 |
| WO | 2010070649 A1 | 6/2010 |
| WO | 2010105046 A1 | 9/2010 |
| WO | 2012137208 A1 | 10/2012 |
| WO | 2013003228 A1 | 1/2013 |
| WO | 2014093861 A1 | 6/2014 |
| WO | 2015020816 A1 | 2/2015 |
| WO | 2016192481 A1 | 12/2016 |

OTHER PUBLICATIONS

Barbero-Marcial, M. et al., "Transxiphoid Approach Without Median Sternotomy for the Repair of Atrial Septal Defects," (1998) Ann. Thorne. Burg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitra! valve repair by replacement of chordae tendineae with polytetrafluoroethylene sutures," (1991) J. Thorne. Cardiovasc. Surg., 101 (3):495-50 I.

David, T. E. et al., "Replacement of chordae tendineae with Gore-Tex sutures: a ten-year experience," (1996) J. Heart Valve Dis., 5(4):352-355.

Doty, D. B. et al., "Full-Spectrum Cardiac Surgery Through a Minimal Incision: Mini-Sternotomy (Lower Half) Technique," (1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitrnl valve prolapse," (1997) J. Heal1 Valve Dis., 6(6):594-598.

Frater, R. W. M. ct al., "Chordal replacement in mitral valve repair," (1990) Circulation, 82(suppl. IV):IV-125-IV-130.

Frater, R. W. M., "Anatomical rules for the plastic repair of a diseased mitral valve," (1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thorne. Surg., 75:809-811.

Kasegawa, H. ct al., "Simple method for determining proper length of al1ificial chordae in mitral valve repair," (1994) Ann. Thorne. Surg., 57(1):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylcnc suture: a finite element study," (1996) J. Card. Surg., 11(2):136-145.

Langer, F. et al., "RING plus STRING: Padillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique," (2000) European journal of Cardiothoracic Surgery, 17(3):201-205.

Merendino, K. A. et al., "The open con-ection of rheumatic mitral regurgitation and/or stenosis with special reference to regurgitation treated by posterornedial annuloplasty utilizing a pump-oxygenator," (1959) Annals of Surgery, 150(1):5-22.

Minatoya, K. et al., "Pathologic aspects of polytetrafluoroethylene sutures in human heart," (1996) Ann. Thorac. Surg., 61 (3):883-887.

Mohty, D. ct al., "Very long-term survival and durability ofmitral valve repair for mitral valve prolapse," (2001) Circulation, 104:1-1-1-7.

*Neochord, Inc. v. Iiniversity of Maryland, Baltimore*, Case No. IPR2016-00208, Petition for inter ParlesReview of U.S. Pat. No. 7,635,386, dated Nov. 18, 2015, 65 pages.

*Neochord, Inc. v. University of Maryland, Bal tim ore*, Case No. JPR2016-00208, Decision on Institution of Inter Faries Review,37 CFR §42. I 08, Paper 6, Entered May 24, 2016, 28 pages.

(56) References Cited

OTHER PUBLICATIONS

*Neochord, Inc.* v. *University of Maryland, Baltimore*, Case No. IPR2016-00208, Declaration of Dr. Lishan Aklog, dated Nov. 17, 2015, 91 pages.

Nigro, J. J. et al., "Neochordal repair of the posterior mitral leaflet," (2004) J. Thorne. Cardiovasc. Surg., 127 (2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al. •Transapical Approach for Mitra! Valve Repair during Insertion of a Left Ventricular Assist Device, Hindawi Publishing Corporation, The Scientific World Journal, vol. 2013, Article ID 925310, [ online], Retrieved from the internet: <URL: http://dx.doi.org/J 0.1155/2013/92531 O> Apr. 11, 2013, 4 pages.

Sarsam, M.A. I., "Simplified technique for determining the length of artificial cl1ordae in milral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database, . . . (2003) Ann. Thorne. Surg., 75:820-825.

Speziali, G. et al., "Collection of Mitra! Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heaii surgery without cardiopulmonary bypass: Atrial septa! defect closure in a swine model," (2005) J. Thorne. Cardiovasc. Surg., 130: 1348-1357.

Von Oppell, U. 0. et al., "Chordal replacement for both minimally invasive and conventional mitral valve surgery using prcrncasurcd Gore-Tex loops," (2000) Ann. Thorne, Surg., 70(6):2166-2168.

Zussa, C. et al., Artificial rnitral valve chordae: experimental and clinical experience;• ( 1990) Ann. Thorne. Surg., 50(3):367-373.

Zussa, C. et al., "Seven-year experience with chordal replacement with expanded polytetrafluoroethylene in floppyrnitral valve," (1994)1. Thorac. Cardiovasc. Surg., 108(1):37-41.

Zussa, C. et al., "Surgical technique for artificial mitral chordae implantation," ( 1991) Journal of Cardiac Surgery, 6(4):432-438.

Zussa, C., "Artificial chordae," (1995) J. Heart Valve Dis., 4(2):S249-S256.

\* cited by examiner

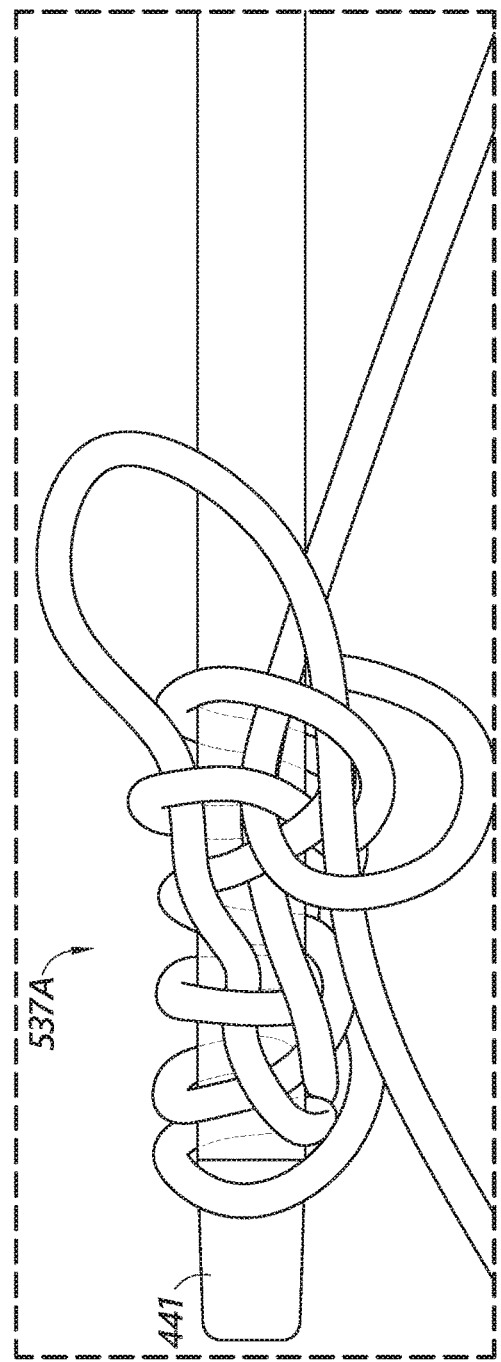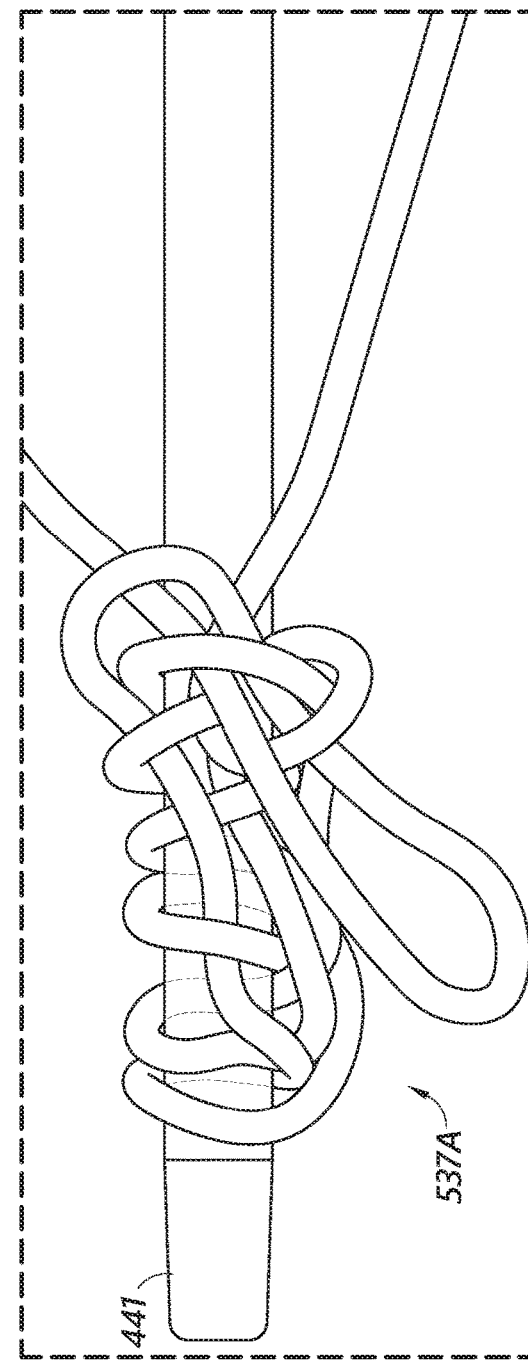

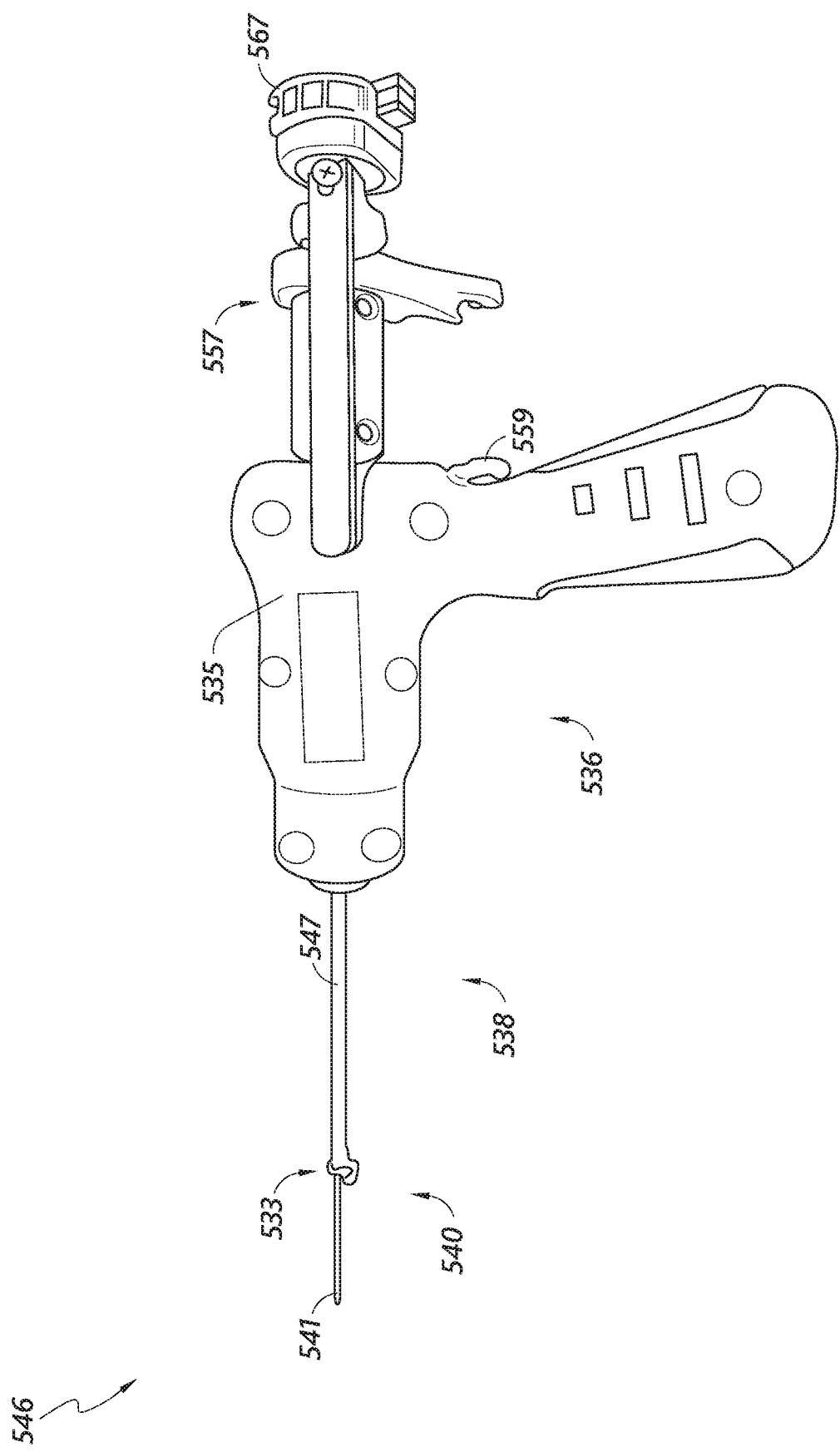

FIG. 15H
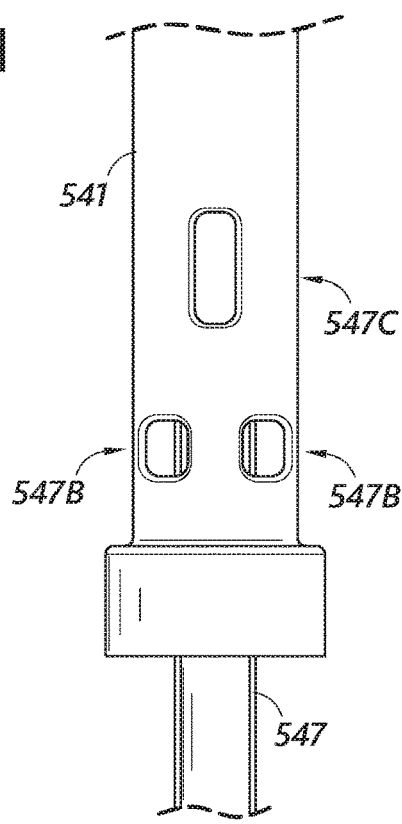
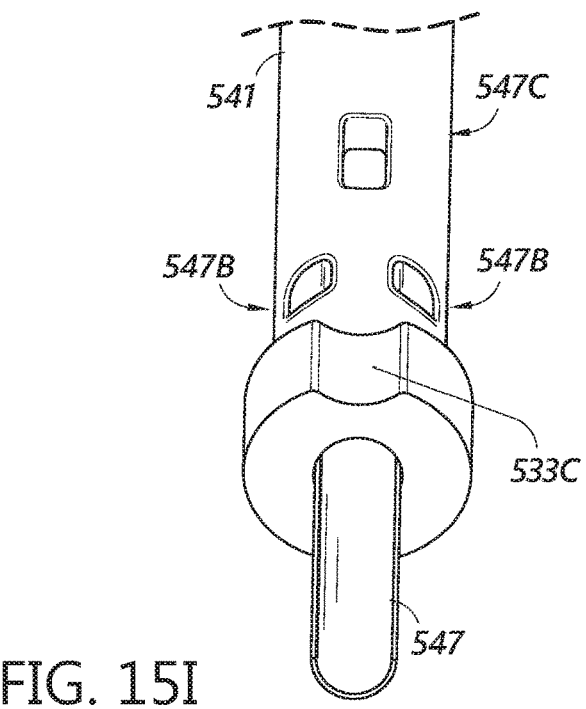
FIG. 15I

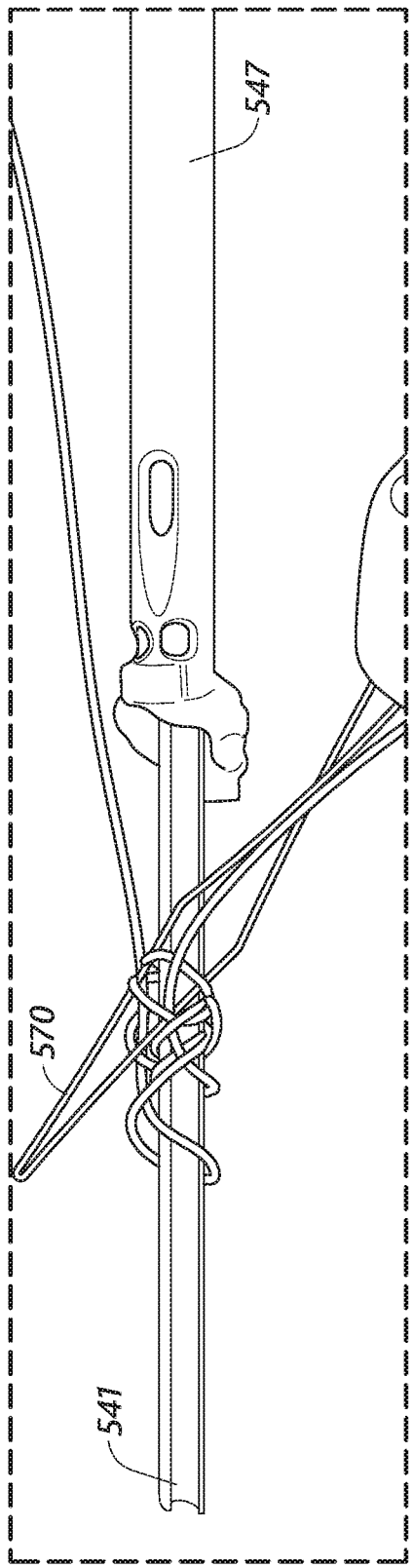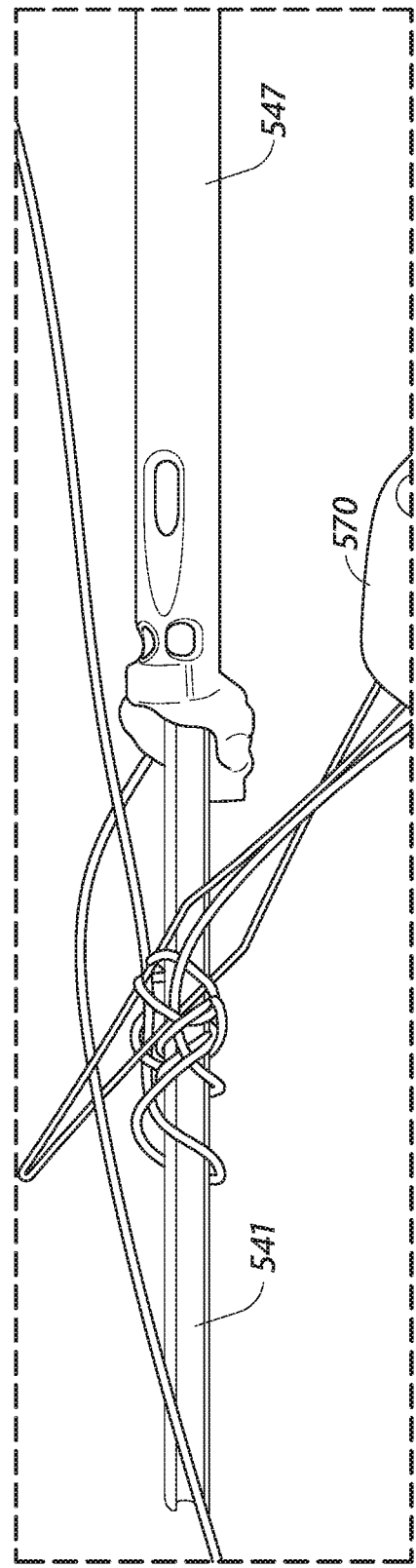

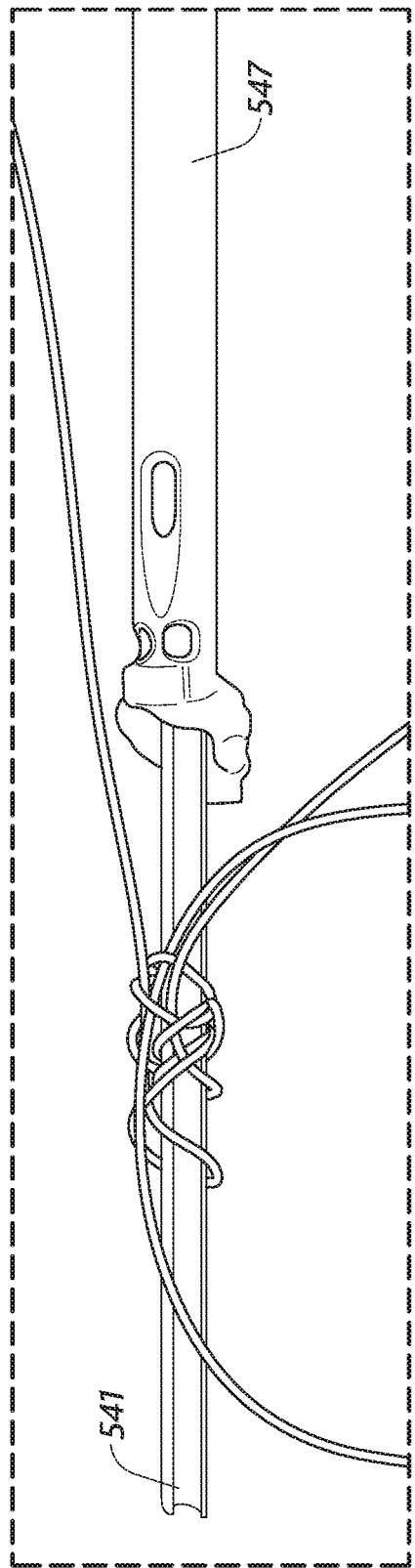
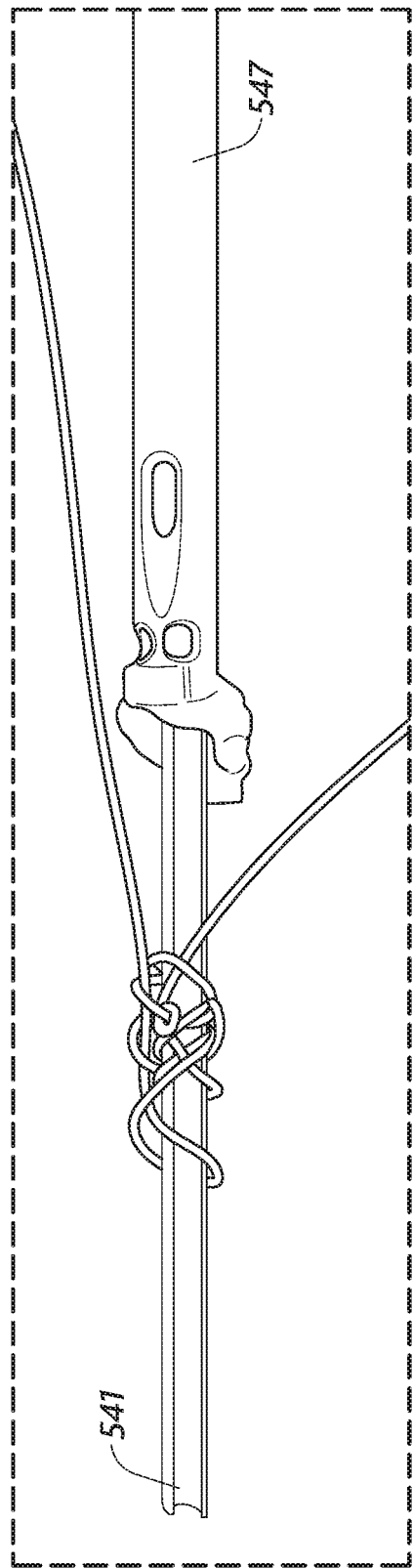

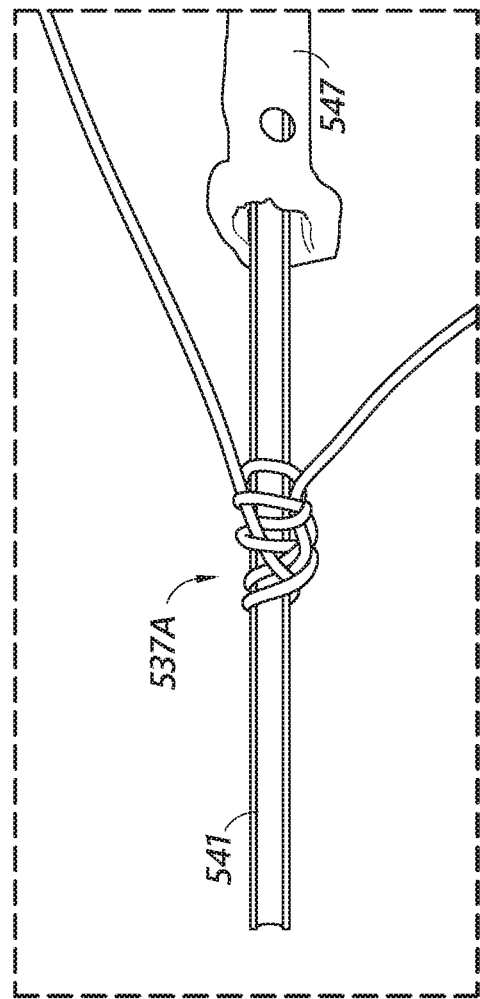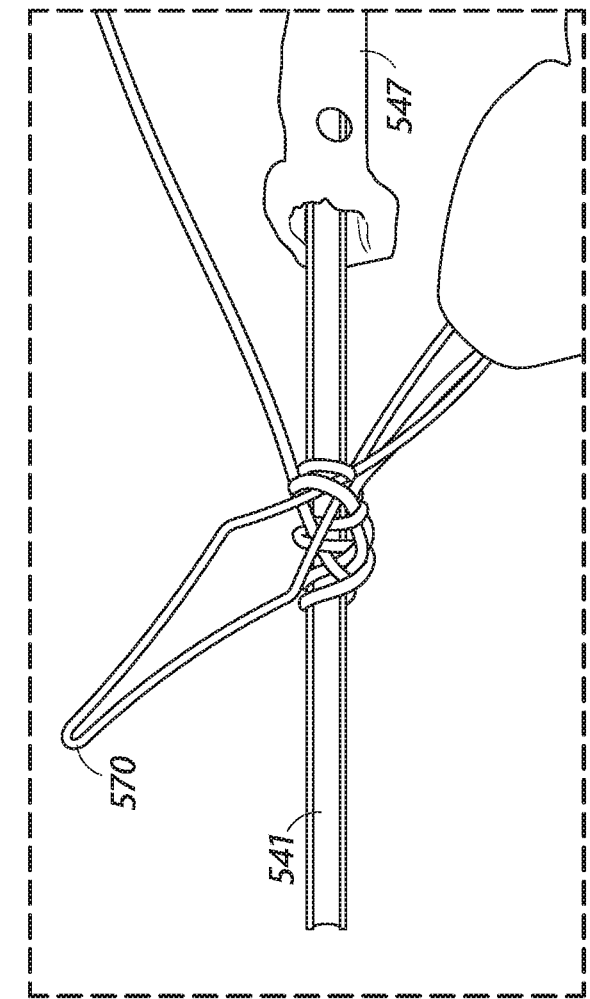
FIG. 17A
FIG. 17B

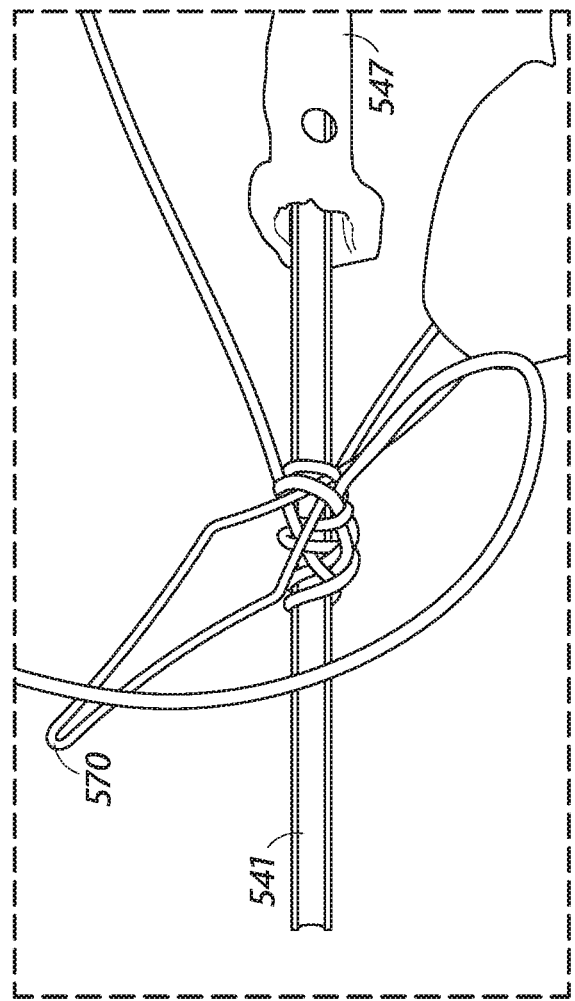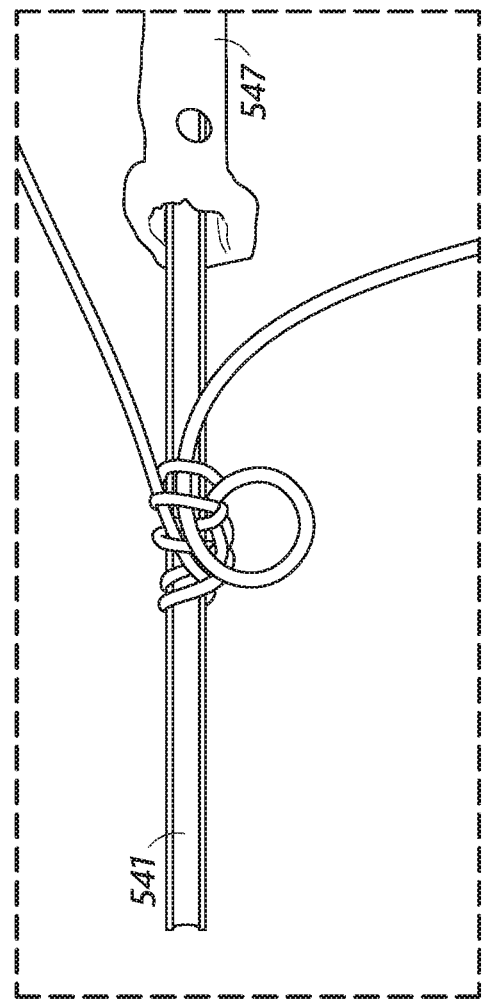

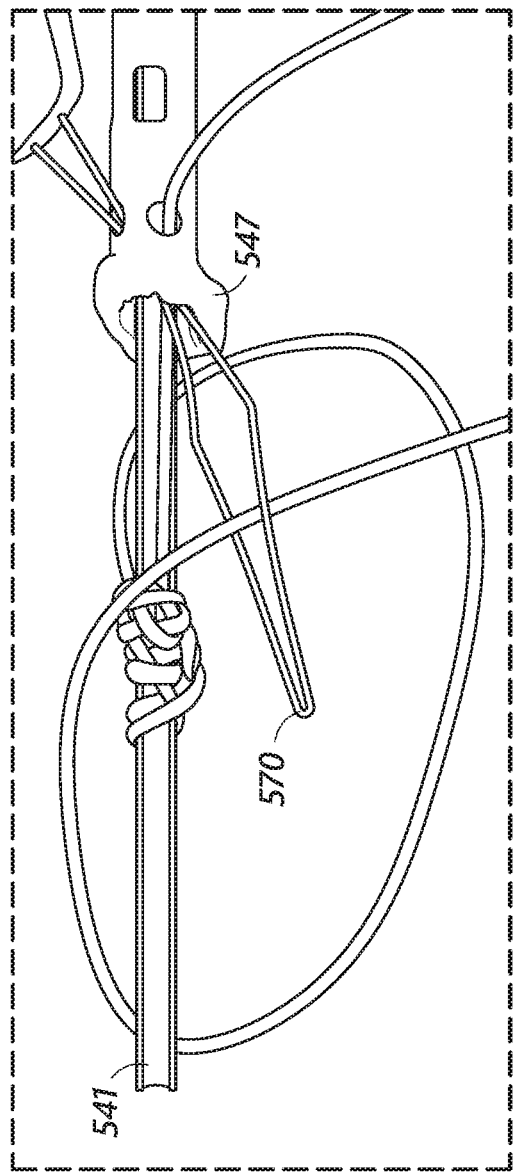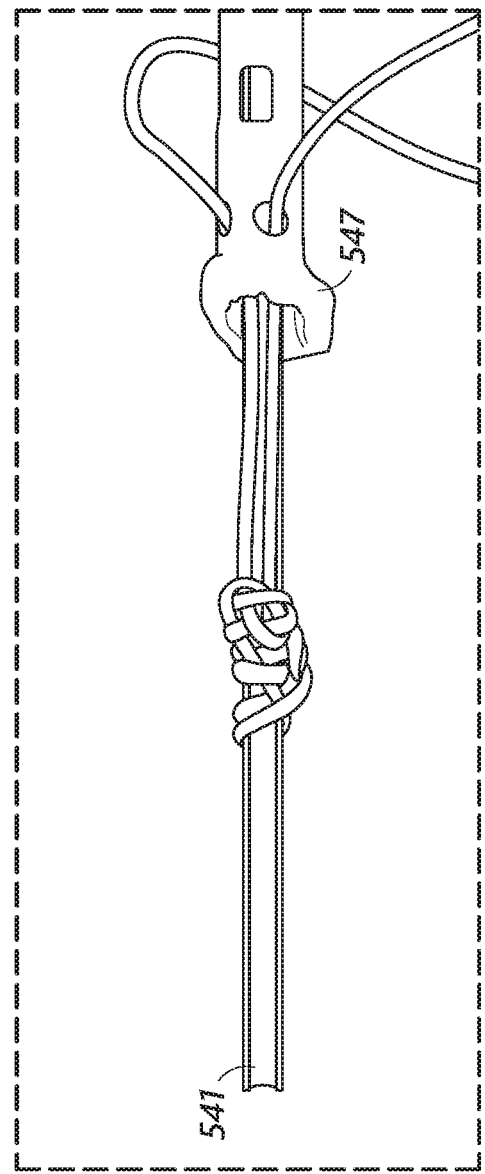

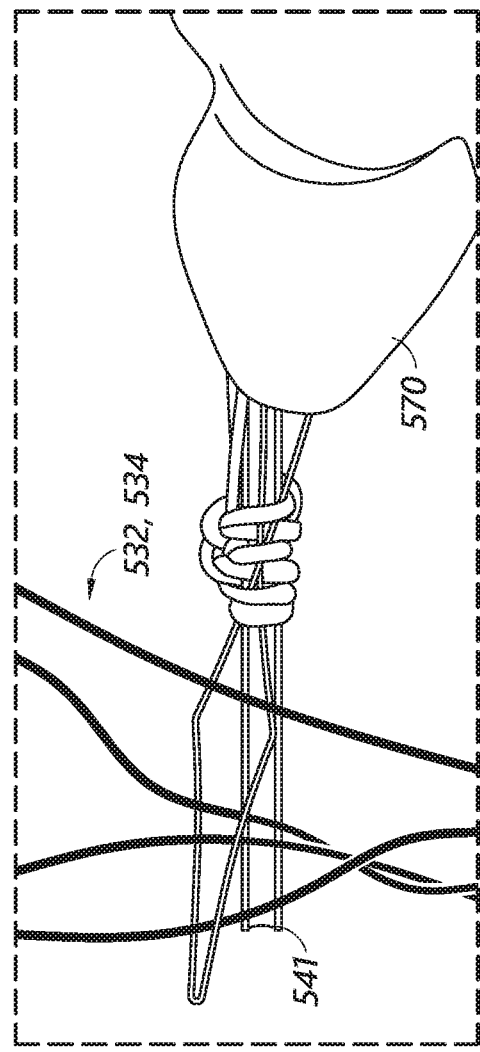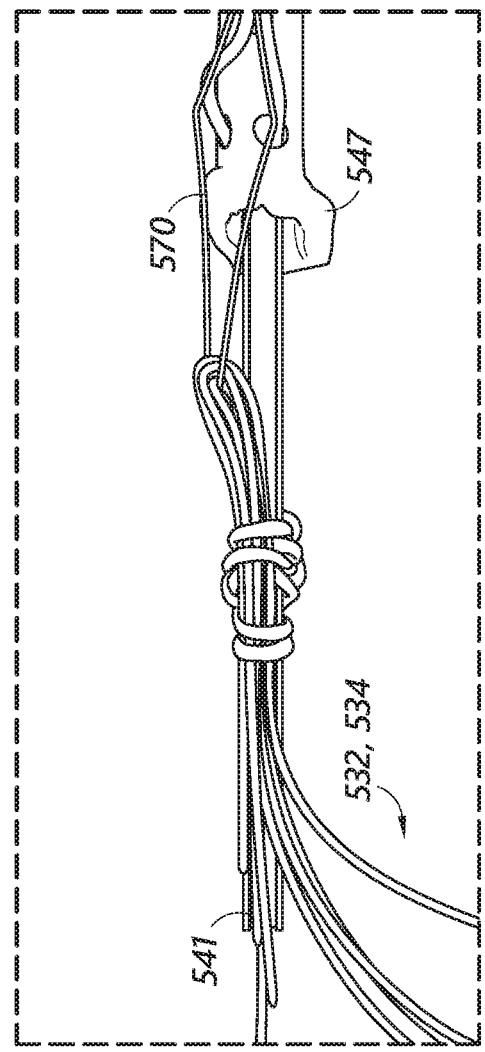
FIG. 17U
FIG. 17V

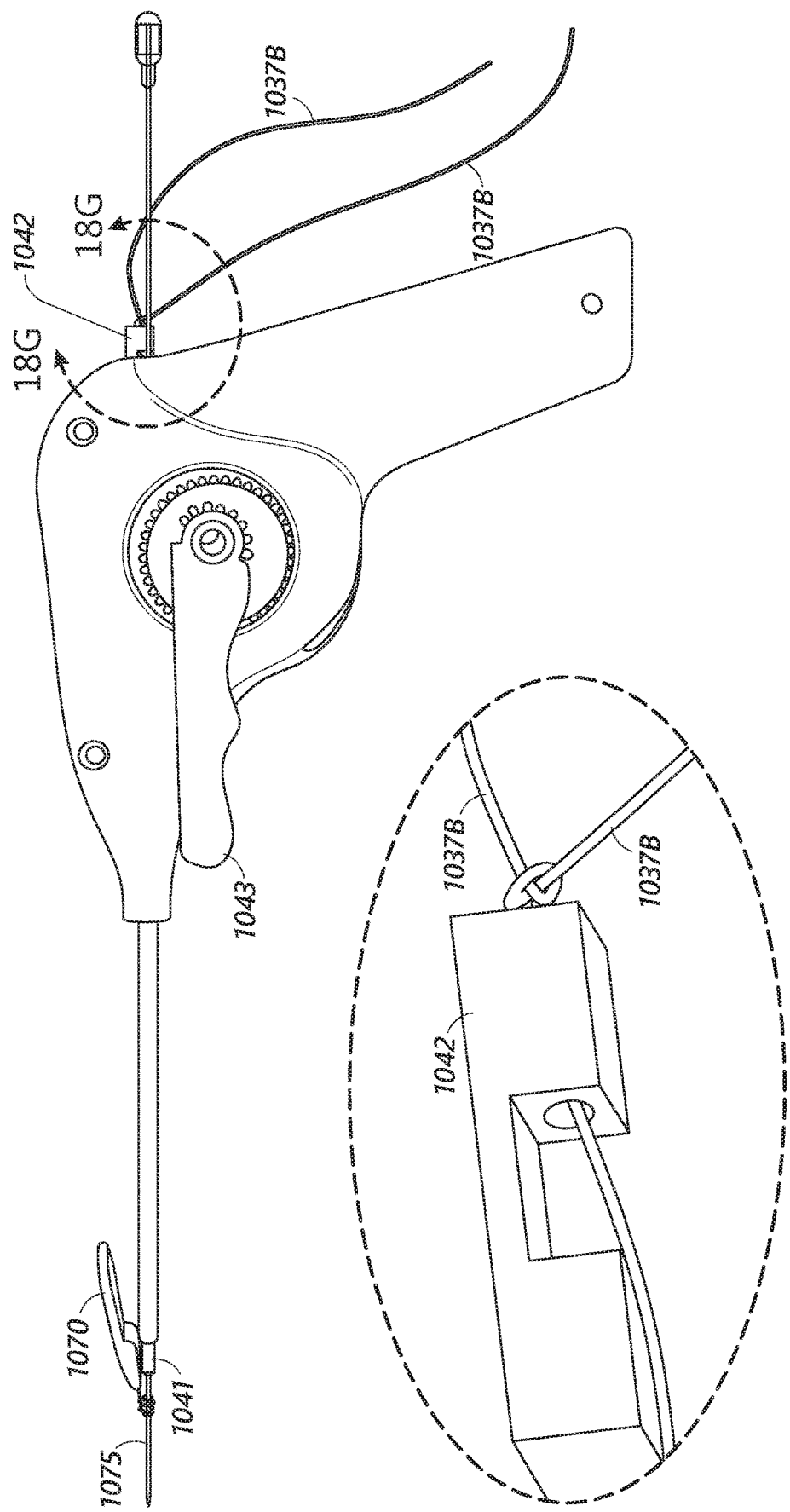

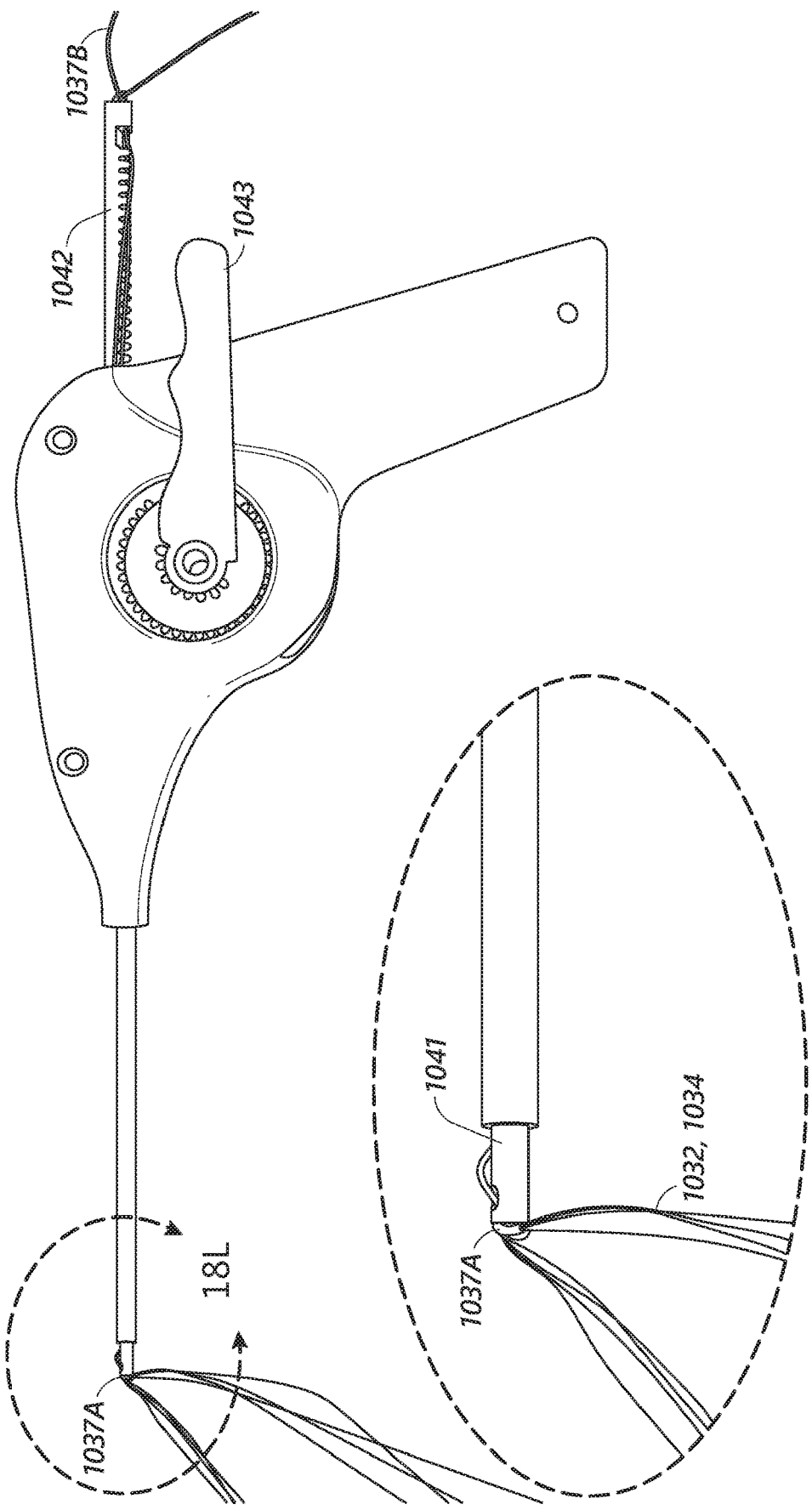

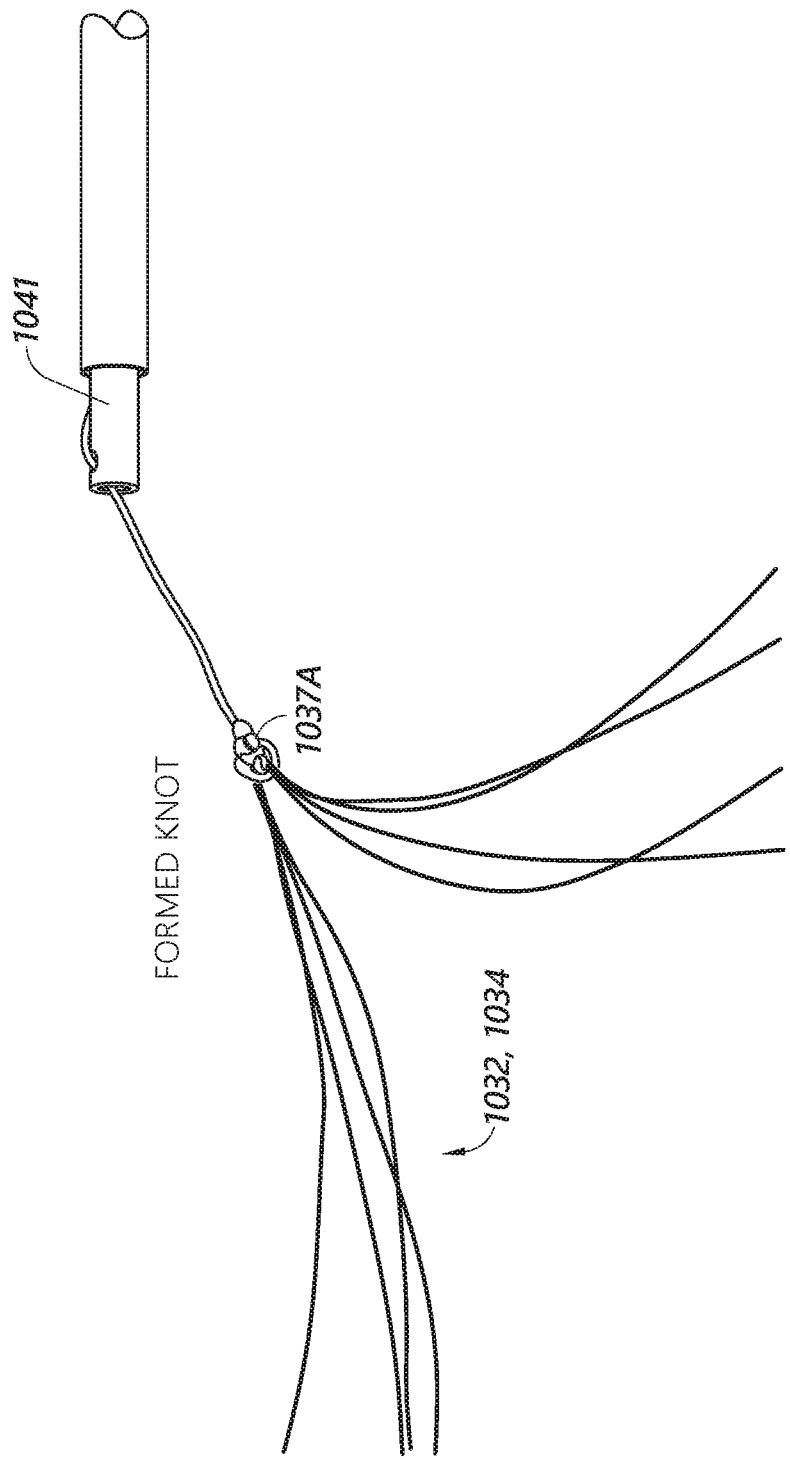

METHOD AND APPARATUS FOR CARDIAC PROCEDURES

CROSS-REFERENCE TO RELATED APPLICATION

This application claims the benefit of U.S. Application No. 62/576,364, filed Oct. 24, 2017, which is expressly incorporated by reference herein in its entirety for all purposes.

BACKGROUND

Field

Some embodiments described herein relate to methods and apparatus for joining two or more sutures together during surgical procedures, such as cardiac valve repairs, and more particularly, methods and apparatus for performing minimally invasive mitral or tricuspid valve repairs.

Description of Related Art

Various disease processes can impair the proper functioning of one or more of the valves of the heart. These disease processes include degenerative processes (e.g., Barlow's Disease, fibroelastic deficiency), inflammatory processes (e.g., Rheumatic Heart Disease), and infectious processes (e.g., endocarditis). Additionally, damage to the ventricle from prior heart attacks (e.g., myocardial infarction secondary to coronary artery disease) or other heart diseases (e.g., cardiomyopathy) can distort the geometry of the heart causing valves in the heart to dysfunction. The vast majority of patients undergoing valve surgery, such as mitral valve surgery, suffer from a degenerative disease that causes a malfunction in a leaflet of the valve, which results in prolapse and regurgitation.

Generally, a heart valve may malfunction in two different ways. One possible malfunction, valve stenosis, occurs when a valve does not open completely and thereby causes an obstruction of blood flow. Typically, stenosis results from buildup of calcified material on the leaflets of the valves causing the leaflets to thicken, thereby impairing their ability to fully open and permit adequate forward blood flow.

Another possible malfunction, valve regurgitation, occurs when the leaflets of the valve do not close completely thereby allowing blood to leak back into the prior chamber when the heart contracts. There are three mechanisms by which a valve becomes regurgitant or incompetent; they include Carpentier's type I, type II and type III malfunctions. A Carpentier type I malfunction involves the dilation of the annulus such that the area of the valve orifice increases. The otherwise normally functioning leaflets do not have enough surface area to cover the enlarged orifice and fail to form a tight seal (e.g., do not coapt properly) causing regurgitation. Included in a type I mechanism malfunction are perforations of the valve leaflets, as in endocarditis. A Carpentier's type II malfunction involves prolapse of a segment of one or both leaflets above the plane of coaptation. This is the most commonly treated cause of mitral regurgitation and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic heart disease (IIIa) or dilation of the ventricle (IIIb).

Mitral valve disease is the most common valvular heart disorder, with nearly 4 million Americans estimated to have moderate to severe mitral valve regurgitation ("MR"), with similar numbers of individuals impacted outside of the United States. MR results in a volume overload on the left ventricle which in turn progresses to ventricular dilation, decreased ejection performance, pulmonary hypertension, symptomatic congestive heart failure, atrial fibrillation, right ventricular dysfunction and death. Successful surgical mitral valve repair restores mitral valve competence, abolishes the volume overload on the left ventricle, improves symptom status, and prevents adverse left ventricular remodeling. While generally safe and effective, conventional open-heart operations are invasive, result in significant disability, and require extended post-procedure recovery. Patients routinely spend five to seven days in the hospital and often are not able to return to normal daily activities for a month or more.

Malfunctioning valves may either be repaired or replaced. Repair typically involves the preservation and correction of the patient's own valve. Replacement typically involves replacing the patient's malfunctioning valve with a biological or mechanical substitute. Typically, replacement is preferred for stenotic damage sustained by the leaflets because the stenosis is irreversible. The mitral valve and tricuspid valve, on the other hand, are more prone to deformation. Deformation of the leaflets, as described above, prevents the valves from closing properly and allows for regurgitation or back flow of blood from the ventricle into the atrium, which results in valvular insufficiency. Deformations in the structure or shape of the mitral valve or tricuspid valve are often repairable.

In many instances of mitral valve regurgitation, repair is preferable to valve replacement. Mitral valve replacement operations have a 2× higher risk of operative mortality (Risk Standardized Mortality 1.65% vs. 2.96%), 2$x$ higher risk of stroke per year (1.15% vs. 2.2%) and a 10$x$ higher risk of infection per year (0.1% vs. 1.0%). Patients who receive a quality mitral valve repair operation do not require anticoagulation and rarely require reoperation. This is in stark contrast to mechanical valve replacement which mandates lifelong anticoagulation and bioprosthetic valve replacement with the eventual certainty of prosthetic valve dysfunction and reoperation. Compared to mitral valve replacement, mitral valve repair results in improved left ventricular function and has superior long-term survival. Therefore, an improperly functioning mitral valve or tricuspid valve is ideally repaired, rather than replaced. Because of the complex and technical demands of the current repair procedures, however, the mitral valve is still replaced in approximately one third of all mitral valve operations performed in the United States.

Studies suggest that Carpentier type II malfunction, often referred to as "Degenerative," "Primary" or "Organic" MR, accounts for as much as 60% of MR. Resectional mitral valve repair techniques, initially described by Dr. Carpentier, involve cutting out (resecting) a section of the prolapsed leaflet tissue, stitching the remaining tissue together and implanting an annuloplasty ring around the annulus. Removing a portion of one or both of the mitral valve leaflets during such a resectional repair decreases the available leaflet tissue to seal the mitral orifice. To accommodate the decrease caused by the resectional repair, in many instances, an annuloplasty ring must be implanted to decrease the size of the mitral orifice.

Implanting an annuloplasty ring introduces various risks. For example, implanting an annuloplasty ring can increase pressure gradients across the valve. Further, an annuloplasty ring can lead to infection and/or annuloplasty ring dehiscence—a well-documented failure mode of valve repair surgery. Implanting an annuloplasty ring can further impact the dynamic nature of the mitral valve annulus throughout the cardiac cycle. In a healthy person, for example, the mitral valve annulus relaxes during diastole and contracts with the rest of the left ventricle during systole, causing the annulus to expand and contract as the heart beats. Implanting an annuloplasty ring can interfere with such normal functioning of the heart. To combat such interference, flexible annuloplasty rings and partial bands have been developed to minimize the impact a rigid or complete annuloplasty ring can have on the dynamic movement of the mitral annulus. To avoid the aforementioned complications and risks, an effective mitral valve repair procedure that eliminated the need for an annuloplasty ring is desirable, particularly a repair that can be performed minimally-invasively and off-pump in which implanting an annuloplasty ring would be present technical challenges.

More recently many surgeons have moved to a "non-resectional" repair technique where artificial chordae tendineae ("cords") made of expanded polytetrafluoroethylene ("ePTFE") suture, or another suitable material, are placed in the prolapsed leaflet and secured to the heart in the left ventricle, normally to the papillary muscle. Because the native leaflet tissue is maintained in non-resectional repairs, they often result in a larger surface of coaptation between the posterior and anterior mitral valve leaflets, but properly sizing the cords on a flaccid heart can be very challenging, especially for the low volume mitral valve surgeon. Implanting an annuloplasty ring with such non-resectional repairs on a stopped heart is currently the standard of care. Implanting an annuloplasty ring in a beating heart repair is technically challenging and rarely done in practice due in large part to the costs associated with two separate procedures (e.g., cordal repair and annuloplasty). A device that can quickly and easily perform a beating-heart cordal repair while also addressing the mitral annulus would be a major advancement.

Carpentier type I malfunction, sometimes referred to as "Secondary" or "Functional" MR, is associated with heart failure and affects between 1.6 and 2.8 million people in the United States alone. Studies have shown that mortality doubles in patients with untreated mitral valve regurgitation after myocardial infarction. Unfortunately, there is no gold standard surgical treatment paradigm for functional MR and most functional MR patients are not referred for surgical intervention due to the significant morbidity, risk of complications and prolonged disability associated with cardiac surgery. Surgeons use a variety of approaches ranging from valve replacement to insertion of an undersized mitral valve annuloplasty ring for patients suffering from functional MR and the long-term efficacy is still unclear. In a randomized study of on-pump, open-heart mitral valve repair versus mitral valve replacement for functional MR, mitral valve replacement had a similar mortality rate and resulted in significantly less recurrent MR after one year and two years. According to some, a subsequent sub-analysis of subjects in the repair group suggests that the people who received a "good repair" did better than the replacement group but that when the repair arm was compared to mitral valve replacement, the "bad repairs" caused the replacement arm to perform better. Either way, there is a need for better treatment options for functional MR. Less invasive, beating-heart, transcatheter repair and replacement technologies are of particular interest because they do not require cardiopulmonary bypass, cardioplegia, aortic cross-clamping or median sternotomy.

Dr. Alfieri has demonstrated the benefit of securing the midpoint of both leaflets together creating a double orifice valve in patients with MR known as an "Edge-to-Edge" repair or an Alfieri procedure. The ability to combine a neochordal repair with an edge-to-edge repair in degenerative MR patients with a dilated annulus and who do not receive an annuloplasty ring because the repair is done in a minimally-invasive, off-pump procedure, has particular promise. Further, performing a facilitated edge-to-edge repair in which sutures placed on both the posterior and anterior leaflets are secured together and then pulled toward the base of the heart has the potential to improve the overall repair. Performing a facilitated edge-to-edge procedure in a minimally-invasive beating heart procedure is a further advancement. Further, in addition to or instead of creating the edge-to-edge relationship, to promote a larger surface of coaptation between the anterior and posterior leaflets, and thereby to promote proper valve function and limit or prevent undesirable regurgitation, sutures extending from the leaflets can be secured together to pull or to otherwise move the posterior annulus towards the anterior leaflet and/or the anterior annulus towards to posterior leaflet. This reduces the distance between the anterior annulus and the posterior annulus (or the septal-lateral distance) (e.g., by about 10%-30%). Approximating the anterior annulus and the posterior annulus in this manner can decrease the valve orifice, and thereby decrease, limit, or otherwise prevent undesirable regurgitation.

Regardless of whether a replacement or repair procedure is being performed, conventional approaches for replacing or repairing cardiac valves are typically invasive open-heart surgical procedures, such as sternotomy or thoracotomy, which require opening up of the thoracic cavity so as to gain access to the heart. Once the chest has been opened, the heart is bypassed and stopped. Cardiopulmonary bypass is typically established by inserting cannulae into the superior and inferior vena cavae (for venous drainage) and the ascending aorta (for arterial perfusion) and connecting the cannulae to a heart-lung machine, which functions to oxygenate the venous blood and pump it into the arterial circulation, thereby bypassing the heart. Once cardiopulmonary bypass has been achieved, cardiac standstill is established by clamping the aorta and delivering a "cardioplegia" solution into the aortic root and then into the coronary circulation, which stops the heart from beating. Once cardiac standstill has been achieved, the surgical procedure may be performed. These procedures, however, adversely affect almost all of the organ systems of the body and may lead to complications, such as strokes, myocardial "stunning" or damage, respiratory failure, kidney failure, bleeding, generalized inflammation, and death. The risk of these complications is directly related to the amount of time the heart is stopped ("cross-clamp time") and the amount of time the subject is on the heart-lung machine ("pump time").

Thus, there is a significant need to perform mitral valve repairs using less invasive procedures while the heart is still beating. Accordingly, there is a continuing need for new procedures and devices for performing cardiac valve repairs, such as mitral valve repair, which are less invasive, do not require cardiac arrest, and are less labor-intensive and technically challenging.

SUMMARY

Apparatus and methods for repairing a tissue by remotely securing two or more sutures together are described herein.

In some embodiments, apparatus and methods for performing a non-invasive procedure to repair a cardiac valve are described herein. In some embodiments, apparatus and methods are described herein for repairing a mitral valve using an edge-to-edge procedure (also referred to as an Alfieri procedure) using a locking suture to secure or join portions of the mitral valve leaflets.

In a first aspect, the present disclosure provides a method for using locking sutures to approximate anchor implants attached to targeted tissue. The method includes attaching two or more cords to targeted tissue, individual cords including a distal anchor implant and a suture extending proximally from the distal anchor implant. The method also includes intertwining proximal end portions of the two or more sutures with a locking suture, the locking suture including a knot portion and a tether portion extending from the knot portion and configured to be manipulated to transition the knot portion from a delivery configuration to a deployed configuration. The method also includes positioning the knot portion of the locking suture along the two or more sutures to approximate portions of the targeted tissue. The method also includes transitioning the knot portion from the delivery configuration to the deployed configuration to lock the locking suture. The method also includes receiving feedback from a visualization system, the feedback including an approximation of the targeted tissue.

In some embodiments of the first aspect, transitioning the knot portion to the deployed configuration does not increase proximal forces on the targeted tissue. In some embodiments of the first aspect, the targeted tissue includes a leaflet of a mitral valve. In some embodiments of the first aspect, positioning the locking suture along the sutures of the two or more sutures results in a point of intersection that approaches the targeted tissue to change a force vector on the two or more cords attached to the targeted tissue.

In some embodiments of the first aspect, the targeted tissue is within a targeted region and positioning the knot portion is done utilizing a locking suture device that is operated outside of the targeted region. In further embodiments of the first aspect, the targeted region is the heart. In further embodiments of the first aspect, the method further includes anchoring the proximal end portions of the two or more sutures. In further embodiments of the first aspect, anchoring the proximal end portions includes securing the proximal end portions to an external wall of the heart.

In some embodiments of the first aspect, the method further includes securing the knot portion to a distal end of a locking suture delivery device. In further embodiments of the first aspect, transitioning the knot portion to the deployed configuration includes manipulating an element of the locking suture delivery device to which the locking suture is secured. In some embodiments of the first aspect, the method further includes applying sequential proximal forces to the proximal end portions using the locking suture delivery device.

In a second aspect, the present disclosure provides a locking suture delivery and deployment device. The device includes a body having a tip portion at a distal end, the tip portion being configured to be atraumatic to targeted tissue. The device also includes a holding component coupled to the body, the holding component having one or more features to secure a pre-formed knot of a locking suture at the distal end, the locking suture including a tether portion with two proximal ends. The device also includes a release component in communication with the holding component, the release component configured to release the pre-formed knot after it has been transitioned from a delivery configuration to a deployed configuration. The device also includes a tensioning component coupled to the body, the tensioning component configured to apply proximal forces to individual proximal ends of the tether portion at different times with targeted tension.

In some embodiments of the second aspect, the tensioning component is configured to transition the pre-formed knot from the delivery configuration to the deployed configuration without increasing tension on the targeted tissue. In some embodiments of the second aspect, the tensioning component includes a rack and pinion configuration. In some embodiments of the second aspect, the release component includes a pusher member to push the pre-formed knot from the holding component.

In some embodiments of the second aspect, the tensioning component is configured to apply a first force to a first proximal end portion of the tether portion and to apply a second force to a second proximal end of the tether portion. In further embodiments of the second aspect, the tensioning component is configured to apply the first force and the second force sequentially without human intervention between application of the first force and the second force. In further embodiments of the second aspect, the first force and the second force are different from one another.

In some embodiments of the second aspect, the tensioning component is configured to automatically stop increasing tension at a targeted tension. In some embodiments of the second aspect, the tensioning component includes a feedback mechanism to indicate when a targeted tension is achieved.

For purposes of summarizing the disclosure, certain aspects, advantages and novel features have been described herein. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

FIGS. 12A, 12B, 12C, 12D, and 12E illustrate an alternate approach for forming the locking suture knot portion of FIGS. 11A-11G.

FIG. 13 illustrates in right side view a LS delivery device, according to an embodiment.

FIG. 15H illustrates a detailed top view version of FIG. 15E.

FIG. 15I illustrates a detailed front perspective view version of FIG. 15E.

FIGS. 16A, 16B, 16C, 16D, 16E, 16F, 16G, 16H, 16I, 16J, 16K, 16L, 16M, 16N, 16O, 16P, 16Q, 16R, 16S, 16T, 16U, 16V, 16W, 16X, 16Y, 16Z, 16AA, 16AB, 16AC, 16AD, 16AE, 16AF, 16AG, 16AH, 16AI, 16AJ, and 16AK illustrate a method of preparing the locking suture of the LS delivery device of FIG. 13 for delivery and deployment.

FIG. 16AL illustrates the locking suture of FIGS. 16A-16AK deployed and secured to sutures extending from implants.

FIGS. 17A, 17B, 17C, 17D, 17E, 17F, 17G, 17H, 17I, 17J, 17K, 17L, 17M, 17N, 17O, 17P, 17Q, 17R, 17S, 17T, 17U, 17V, and 17W illustrate an alternate method of forming the locking suture described with reference to FIGS. 16A-16AK.

FIGS. 18A, 18B, 18C, 18D, 18E, 18F, 18G, 18H, 18I, 18J, 18K, 18L, and 18M illustrate another example LS delivery device with a tensioning mechanism that includes a rack and pinion configuration.

DETAILED DESCRIPTION OF SOME EMBODIMENTS

Figure 1:
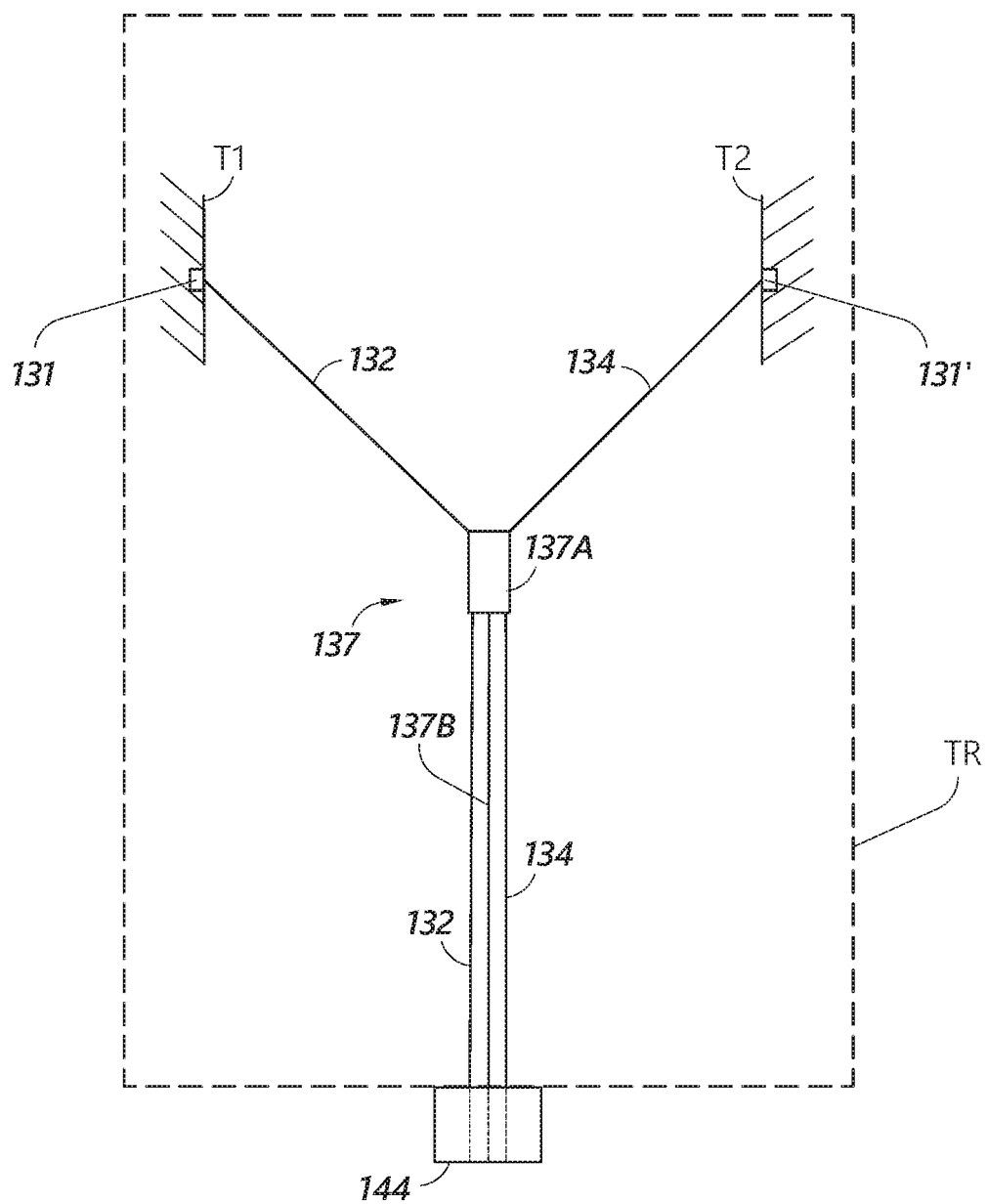
FIG. 1 illustrates schematically a locking suture deployed within a target region for approximating tissues therein, according to an embodiment.

The headings provided herein, if any, are for convenience only and do not necessarily affect the scope or meaning of the claimed invention.

Overview

During conventional, on-pump cardiac operations, the heart is stopped and the doctor has vision of and direct access to the internal structures of the heart. In conventional operations, doctors perform a wide range of surgical procedures on a defective valve. In degenerative mitral valve repair procedures, techniques include, for example and without limitation, various forms of resectional repair, chordal implantation, and edge-to-edge repairs. Clefts or perforations in a leaflet can be closed and occasionally the commissures of the valve sutured to minimize or eliminate MR. Although devices have been developed to replicate conventional mitral valve procedures on a beating heart (see, e.g., International Patent Application No. PCT/US2012/043761, published as WO 2013/003228 A1, and referred to herein as "the '761 PCT Application") there is a need to expand the "toolbox" available to doctors during these minimally invasive procedures.

The ability to remotely (e.g., from outside the heart during a cardiac valve repair) and adjustably secure two or more otherwise separate strands of suture together within a body has wide ranging applications. One application, for example, is in minimally-invasive, beating-heart, cardiac procedures. The ability to remotely secure two or more suture strands together while the heart is beating should dramatically expand the utility of the devices that have been used in cardiac operations to date.

In some embodiments, a method for repairing tissue includes inserting a delivery device, such as a delivery device described in the '761 PCT Application and/or in International Patent Application No. PCT/US2016/055170 (published as WO 2017/059426A1 and referred to herein as "the '170 PCT Application"), the entire disclosure of each of which is incorporated herein by reference, into a body and extending a distal end of the delivery device to a proximal side of the tissue. Advancement of the delivery device may be performed in conjunction with sonography or direct visualization (e.g., direct transblood visualization), and/or any other suitable remote visualization technique. With respect to cardiac procedures, for example, the delivery device may be advanced in conjunction with transesophageal (TEE) guidance or intracardiac echocardiography (ICE) guidance to facilitate and to direct the movement and proper positioning of the device for contacting the appropriate target cardiac region and/or target cardiac tissue (e.g., a valve leaflet, a valve annulus, or any other suitable cardiac tissue). Typical procedures for use of echo guidance are set forth in Suematsu, Y., J. Thorac. Cardiovasc. Surg. 2005; 130:1348-56 ("Suematsu"), the entire disclosure of which is incorporated herein by reference.

A piercing portion of the delivery device can be used to form an opening in the tissue, through which the distal end of the delivery device can be inserted. The delivery device can be used to form or deliver an implant (e.g., a distal anchor) to the distal side of the tissue. The delivery device can be used in this manner to deliver two or more implants to the distal side of the tissue. The implants can be delivered to a single tissue (e.g., a posterior mitral valve leaflet), or one or more implants can be delivered to a first tissue (e.g., a posterior mitral valve leaflet), and one or more other implants can be delivered to a second tissue (e.g., an anterior mitral valve leaflet, a mitral valve annulus, or any other suitable tissue) separate from the first tissue. The delivery device can then be withdrawn, and suture portions extending from the implants can extend to a location (e.g., an outside surface of the heart or other suitable organ) remote from the tissue(s). The remote suture portions can then be coupled to a locking suture delivery and deployment device (also referred to as a locking suture device or locking suture delivery device) that can be operated from outside the target region to deliver and to deploy a locking suture within the targeted region about the suture portions extending from the tissue(s). Advantageously, using the methods and apparatus disclosed herein, introducing additional foreign objects, such as, for example, a securing device, to an area within the target region (e.g., the heart) within which the tissues are located, can be avoided. For example, in a non-invasive cardiac procedure to repair cardiac tissue(s) within the heart, the locking suture device can remain outside the heart and can be used to selectively and remotely secure the suture portions extending from the implants and to selectively, reversibly, and controllably approximate the tissue(s) from which the suture portions extend.

In addition, applications exist that use knotting, joining, securing, and/or approximating multiple sutures together. In connection with an annuloplasty procedure, for example, one or more pairs of sutures can be used to secure the annuloplasty ring around the mitral annulus. The suture pairs may be joined using embodiments of the devices and methods disclosed herein. As another example, in connection with a procedure (e.g., a mitral valve repair) in which multiple suture tails or free ends extend outside the heart, it may be useful to join those sutures and secure them to an anchor (e.g., a pledget) outside the heart. In yet a further example, it may be useful to join and to tie down multiple sutures in connection with addressing congenital intracardiac defects. As yet another example, knotting, joining, securing, and/or approximating multiple sutures together may be useful in minimally invasive thoracic and/or abdominal surgeries where, for example, there is restrictive or limited space (e.g., when working through relatively small trocar portal(s)). Another example includes using sutures to restrict or cut off blood flow in a damaged blood vessel, such as in the brain. The disclosed locking sutures, devices, and methods can be used to secure sutures in a way that restricts blood flow through targeted blood vessels.

Thus, there is a significant need to knot, join, secure, and/or approximate multiple sutures together in various medical applications in addition to mitral valve repairs. Accordingly, there is a continuing need for new procedures and devices which are less invasive, less labor-intensive, and less technically challenging. Examples of such procedures and devices are disclosed herein.

FIG. 1 illustrates schematically an example of a locking suture 137 deployed within a target region TR for approximating tissues T1, T2 therein. The locking suture 137 includes a knot portion 137A configurable between a delivery configuration and a deployed configuration, and a tether portion 137B extending from the knot portion 137A and configured to be manipulated outside the target region TR to transition the knot portion 137A within the target region TR from its delivery configuration to its deployed configuration.

As shown, with a first suture portion 132 extending from an implant 131 secured to tissue T1 and a second suture portion 134 extending from an implant 131' secured to tissue T2, the locking suture 137 can be secured within the target region TR to both the first suture portion 132 and the second suture portion 134, and can be anchored to a location outside the target region TR.

As described in greater detail herein, translating or moving the locking suture 137 distally and/or proximally along the free ends of the sutures 132, 134 can change the distance between the implants 131, 131' and therefore the tissues T1, T2. Once a targeted tissue or implant approximation is achieved, the locking suture 137 can be locked by transitioning the knot portion 137A from its delivery configuration to its deployed configuration using the tether portion 137B.

The locking suture 137 can be formed of any suitable material. In some instances, for example, the locking suture can made of one or more of expanded polytetrafluoroethylene ("ePTFE") suture, polybutylate-coated polyester suture, or polyester suture (such as, for example, Ethibond Excel® Polyester Suture, Johnson & Johnson, New Brunswick, N.J.). In some instances, the locking suture can be modified to increase its coefficient of friction to improve its locking capability. The locking suture, made from ePTFE for example, can be braided, twisted, or knotted (e.g., with overhand knots). Additionally, or alternatively, in some instances, the locking suture's thickness and/or surface texture (e.g., textured surface, coating, etc.) can be configured to increase its coefficient of friction and/or improve its locking capabilities.

In some implementations, the implants 131, 131' can be delivered and disposed on an atrial, distal, or top side of heart valve leaflets (e.g., mitral valve leaflets). The implants 131, 131' can be formed with a suture material that forms a loop on the atrial, distal, or top side of the leaflets and extends through the leaflets, with two loose suture end portions that extend on the ventricular, proximal, or bottom side of the leaflets. In some embodiments, implants can be formed separately from and then attached to the suture end portions. In this manner, the implants can be attached to the suture material, deployed on the atrial side of the leaflets, and the suture end portions can extend from the implants and through the leaflets to the ventricular side of the leaflets, and then anchored outside the target region TR (e.g., the heart) as described in further detail herein.

The knot portion 137A of the locking suture 137 when in its delivery configuration (as described in further detail below) can be slidably coupled to and delivered (e.g., pushed distally) along the suture portions 132, 134 into and through the target region TR using a delivery device that is operated from outside the target region TR (e.g., controlled remotely and delivered minimally invasively). The knot portion 137A can be in the form of braided, twisted, coiled, looped, and/or knotted lines (e.g., sutures). In a delivery configuration, the knot portion 137A can be loose enough to allow a plurality of sutures to slide therethrough. In a delivery configuration, the knot portion 137A can be constricted to create a tortuous path for the plurality of sutures passing through the knot portion. For example, the knot portion 137A can be in the form of one or more multi-turn coils distributed about various regions of the suture portions 132, 134, and the coils can be changed from an elongated, delivery configuration, in which the knot portion 137A is slidable, translatable, and/or pushable along or about the suture portions 132, 134 while maintaining its integrity (e.g., its coiled formation), to a deployed configuration by constricting the coils and/or approximating opposite ends of the coil(s) towards each other to lock or secure the knot portion 137A to the suture portions 132, 134 and inhibit relative motion therebetween.

As described in further detail below, to deploy knot portion 137A (e.g., to transition the knot portion 137A from its delivery configuration to its deployed configuration), the tether portion 137B can be pulled proximally. This causes the knot portion 137A to constrict on the suture portions 132, 134 so that they are secured together within the knot portion 137A at a targeted location within the target region TR relative to the tissues T1, and T2. In addition, the knot portion 137A can be secured in a way that the knot portion 137A does not move distally or proximally along the suture portions 132, 134. With the knot portion 137A secured or locked to the suture portions 132, 134 at a targeted location within the target region TR, the free ends of the suture portions 132, 134 and the free ends of the tether portion 137B extend to a location outside the target region TR. In this configuration, the tether portion 137B and the free ends of the suture portions 132, 134 can be coupled to and secured outside the target region TR using a proximal anchor 144. For example, the tether portion 137B and the free ends of the suture portions 132, 134 can be secured via the proximal anchor 144 to an external or outer surface of a tissue, such as the heart.

FIGS. 2A, 2B, 2C, and 2D illustrate schematically examples of a method and a device for approximating tissues T1, T2 (e.g., mitral valve leaflets within a heart) by delivering and deploying a locking suture 237 using a locking suture (LS) delivery device 246. Advantageously, with the LS delivery device 246 disposed partially outside the target region TR, a user can control or manipulate the LS delivery device 246 from outside the target region TR to deliver and to deploy the locking suture 237 within the target region TR.

Figure 2A:
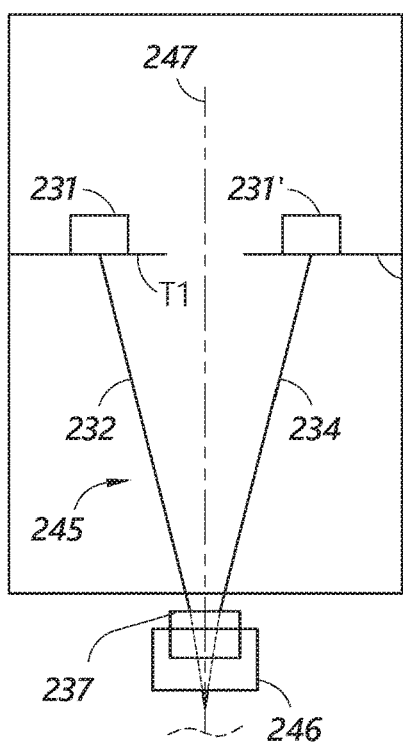
FIGS. 2A, 2B, 2C, and 2D illustrate schematically a method and device for approximating tissues using a LS delivery device, according to an embodiment.

FIG. 2A illustrates a first suture portion 232 extending from a first implant 231 secured to a first tissue T1 and a second suture portion 234 extending from a second implant 231' secured to a second tissue T2. The first suture portion 232 and the second suture portion 234 can extend to a location remote from the tissues T1, T2 (e.g., an outer surface of the heart), and can be operably coupled to the LS delivery device 246 outside the target region TR. The first and second suture portions 232, 234 can be passed through the locking suture 237 that is coupled to an end of the LS delivery device 246. In some embodiments, the first and second suture portions 232, 234 can be threaded through portions of the locking suture. In some embodiments, the first and second suture portions 232, 234 can pass through a central portion of the locking suture 237 (e.g., a lumen formed by one or more coils of the locking suture 237). Advantageously, although each suture portion 232, 234 is coupled to the LS delivery device 246 remote from the tissues T1, T2 and is outside the target region TR, the LS delivery device 246 can deliver and deploy the locking suture 237 within the target region TR to approximate the tissues T1, T2.

Figure 2B:
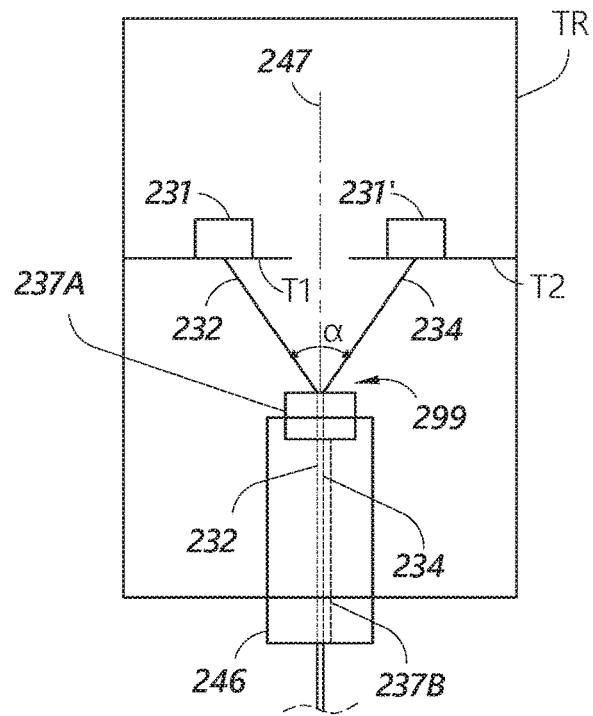

FIG. 2B illustrates inserting a portion of the LS delivery device 246 into the target region TR to move the locking suture 237 to a targeted location. In some embodiments, actuation of the LS delivery device 246 can operate (1) to deliver the locking suture 237 in its delivery configuration, and (2) to transition the locking suture 237 into its deployed configuration. In its delivery configuration, the knot portion 237A of the locking suture 237 is able to slide or translate along, or otherwise move relative to, the suture portions 232, 234, to a targeted location within the target region TR. In its deployed configuration, the knot portion 237A of the locking suture 237 is tightened, compressed (e.g., radially and/or laterally), cinched, or otherwise secured to the suture portions 232, 234.

More specifically, to deliver the locking suture 237, the LS delivery device 246 is used to push, urge, slide, translate or otherwise move the knot portion 237A in its delivery configuration distally along the suture portions 232, 234 within the target region TR. Movement of the knot portion 237A can be along a translation axis 247 that is preferably, but not necessarily, oriented between the axes of the suture portions 232, 234. In some embodiments, the axis 247 may approximately bisect the angle α defined between the axes of the suture portions 232, 234.

As the LS delivery device 246 is used to move the knot portion 237A distally into the target region TR and towards the tissues T1, T2, the suture portions 232, 234 define a point of intersection 299 of the axes of the suture portions 232, 234. As the LS delivery device 246 further urges the knot portion 237A distally within the target region TR, the point of intersection 299 is moved towards the implants 231, 231' (and thus the tissues T1, T2), the lengths of the suture portions 232, 234 between the point of intersection 299 and the respective tissues T1, T2 shorten, and the angle α defined between the axes of the suture portions 232, 234 increases.

With the knot portion 237A delivered to a targeted, suitable, or desirable position (e.g., causing a targeted approximation of the tissues T1, T2), the tether portion 237B can be pulled proximally or withdrawn to deploy the knot portion 237A. Deployment of the knot portion 237A inhibits relative movement between the knot portion 237A and the suture portions 232, 234 disposed therein. Advantageously, pulling the tether portion 237B does not significantly increase or alter the tension on the suture portions 232, 234 and, consequently, the force or tension on the distal anchors 231, 231' and the tissue T1, T2 does not significantly change during deployment of the knot portion 237A. Likewise, while deploying the knot portion 237A, the force or tension applied to the tether portion 237B that causes the knot portion 237A to deploy is directed to the knot portion 237A at the distal tip of the LS delivery device 246 and not to the distal anchors 231, 231' or the tissues T1, T2. Thus, the suture portions 232, 234, the distal anchors 231, 231', and/or the tissues T1, T2 can be free from any additional tension or force applied when deploying the knot portion 237A. This may be due at least in part to the design of the distal end of the LS delivery device 246. For example, as described herein, the distal tip of the LS delivery device 246 can include one or more features that angle the tether portion 237B at a desired angle so that stress applied to the tether portion 237B causes the knot portion 237A to constrict or tighten while not applying significant proximal force that may cause the knot portion 237A to pull proximally on the suture portions 232, 234.

Figure 2C:
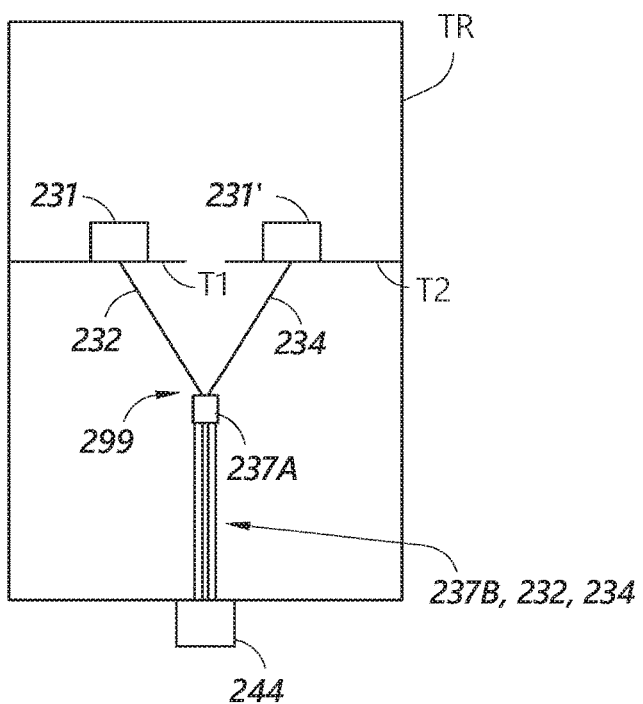

FIG. 2C illustrates the locking suture 237 in its deployed configuration, secured to the first and second suture portions 232, 234. After delivery and deployment of the locking suture 237, the LS delivery device 246 can be withdrawn proximally (e.g., along the suture portions 232, 234 extending proximally from the locking suture 237) and removed from the target region TR. Removing the LS delivery device 246 leaves behind the deployed locking suture 237 secured to the suture portions 232, 234 at a targeted location within the target region TR. In some embodiments, the targeted location can be selected or based on a targeted approximation of tissues T1, T2 and/or a targeted amount of tension applied by the suture portions 232, 234 to the tissues T1, T2.

In certain embodiments, the free ends of the suture end portions 232, 234 and the free ends of the tether portion 237B can extend from the deployed locking suture 237 within the target region TR to an area outside the target region TR. These ends can be secured via a proximal anchor 244 outside the target region TR (e.g., against an outer surface of the heart).

Figure 2D:
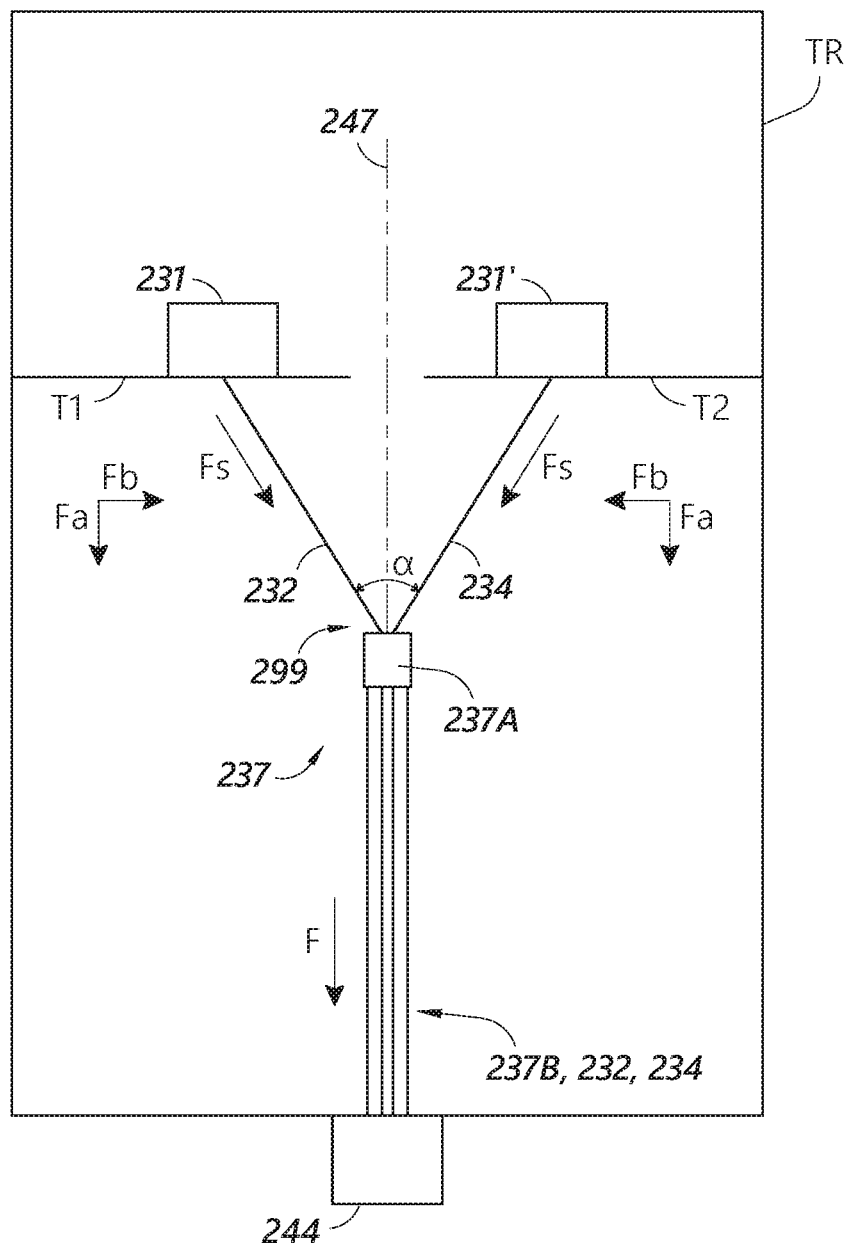

As illustrated in FIG. 2D, a force, F, applied to the locking suture 237 and/or to the two suture portions 232, 234 (and considering each suture portion 232, 234 as a pure tension member), results in an axial force, Fs, carried by each suture portion 232, 234 between the knot portion 237A and the tissues T1, T2 along the respective axes of the suture portions 232, 234. Each axial force, Fs, can be decomposed into a first component, Fa, that is parallel to the axis 247 that bisects the angle α and a second component, Fb, that is perpendicular to the axis 247. The second component, Fb, of the axial force, Fs, in each suture portion 232, 234 acts to approximate, or draw together, the tissue T1, T2 to which the implants 231, 231' are coupled.

The LS delivery device 246 can be used to slide the knot portion 237A distally or proximally along the suture portions 232, 234 to change the angle α and the location of the point of intersection 299. For example, pushing the knot portion 237A distally approximates the implants 231, 231'. Similarly, pulling the knot portion 237A proximally reduces the amount of approximation of the implants 231, 23P. For example, the LS delivery device 246 can be withdrawn (e.g., when in its delivery configuration) proximally before the locking suture 237 is deployed to withdraw the knot portion 237A proximally to reduce the approximation of the implants 231, 231'. Thus, the degree of approximation can be increased or decreased until the desired or targeted approximation is achieved. In some implementations, the targeted degree of approximation can be confirmed under image guidance (e.g., echocardiography). The LS delivery device 246 can then be actuated to transition the knot portion 237A of the locking suture 237 from its delivery configuration to its deployed configuration to lock, radially and/or laterally compress (described in more detail herein), and/or otherwise secure the locking suture 237 in place relative to the suture portions 232, 234. This results in the degree of approximation of the implants 231, 231' being substantially secured and maintained after the LS delivery device 246 is removed. The LS delivery device 246 can then be withdrawn from the target region TR and decoupled or withdrawn from the suture portions 232, 234 and the tether portion 237B. The suture portions 232, 234 and the free ends of the locking suture 237 can be secured outside the target region TR in a suitable location (e.g., an outer surface of the heart) with, for example, a proximal anchor 244.

As described herein, the knot portion 237A has (1) a delivery configuration in which the locking suture 237 is pushable, slidable or deliverable along or about the suture portions 232, 234, and (2) a deployed configuration in which the knot portion 237B is further engaged with, further constricted about, compressed (e.g., radially and/or laterally), cinched, secured, tightened, or fixed to the suture portions 232, 234, such that relative motion between the knot portion 237A and a portion of the suture portions 232, 234 is inhibited and/or prevented. In the delivery configuration, the knot portion 237A is wrapped, intertwined, looped, turned, wound, or otherwise engaged with the suture portions 232, 234 in a manner that allows the locking suture 237 to maintain its structural integrity (e.g., its coiled disposition) such that it is in a ready-state to be deployed, while allowing sufficient relative movement between the locking suture 237 and the suture portions 232, 234. This allows the knot portion 237A to be moved distally and/or proximally along the suture portions 232, 234.

Figure 3A:
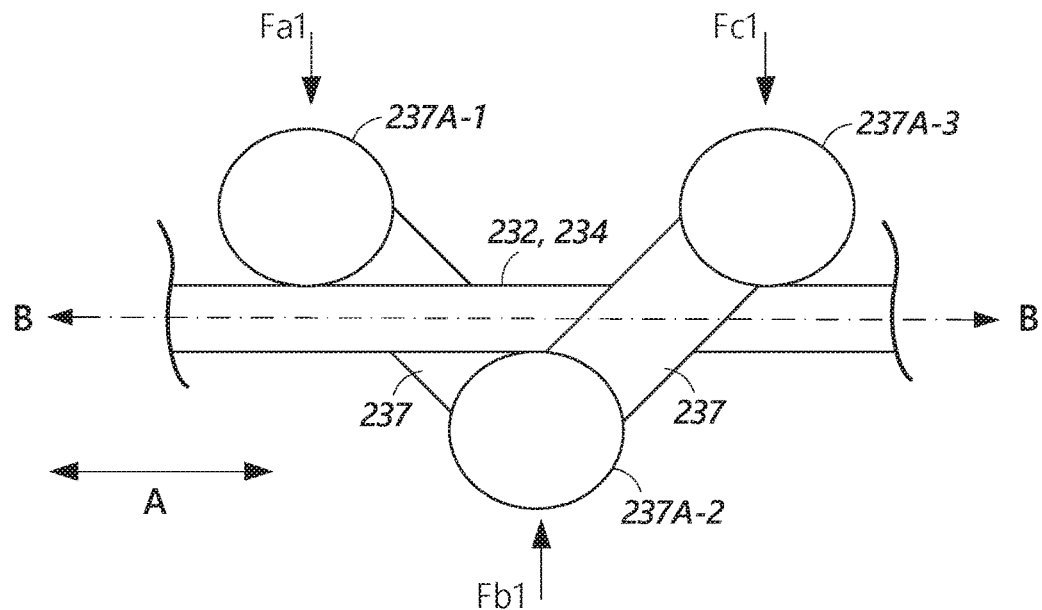
FIGS. 3A, 3B, 3C, and 3D illustrate schematically and conceptually a method of deploying the locking suture of FIGS. 2A-2D.
Figure 3B:
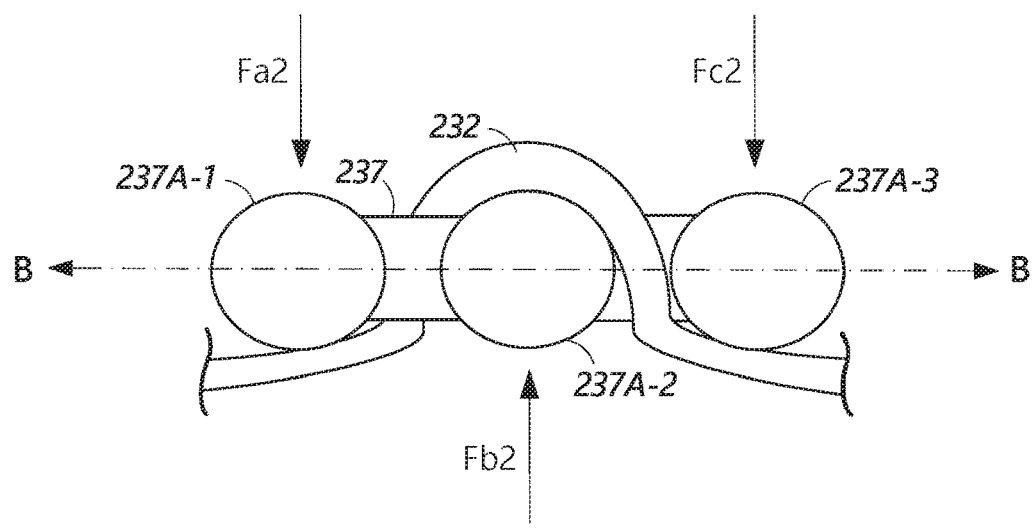
Figure 3C:
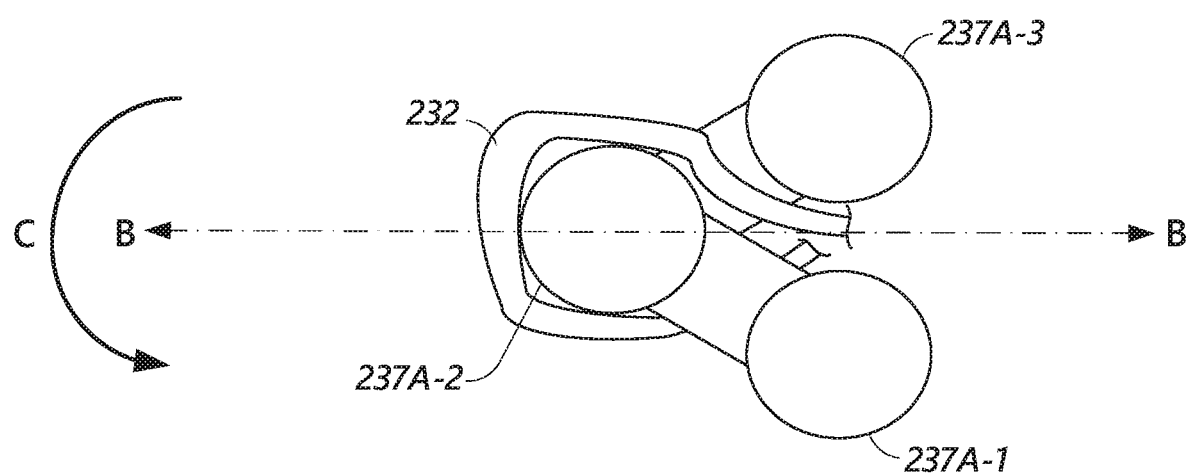
Figure 3D:
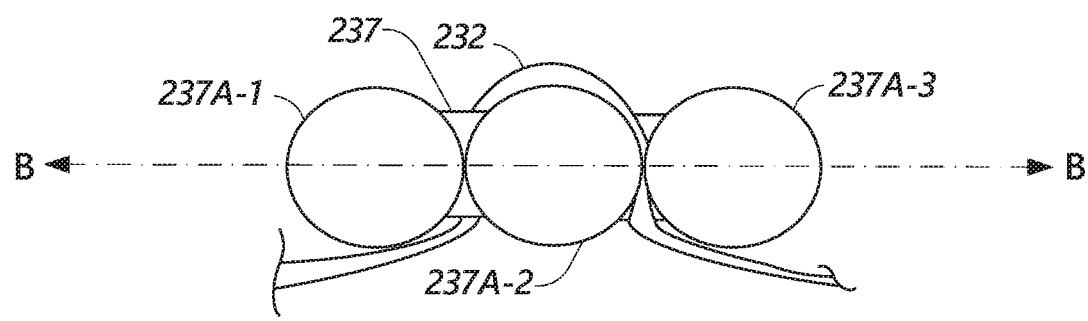

FIGS. 3A-3D conceptually illustrate a segment of the knot portion 237A of FIGS. 2A-2D disposed about the suture portions 232, 234 as it transitions from a delivery configuration to a deployed configuration. For ease of description, transitioning to the deployed configuration is presented as having a number of sequential stages, however, it is to be understood that the stages or portions of the stages may occur simultaneously or in a different order. FIG. 3A illustrates the segment of the knot portion 237A in the delivery configuration disposed about the suture portions 232, 234. FIG. 3B illustrates the segment of the knot portion 237A in a first stage of the deployed configuration where the knot portion 237A experiences radial compression. FIG. 3C illustrates the segment of the knot portion 237A in a second stage of the deployed configuration where the knot portion 237A experiences lateral compression. FIG. 3D illustrates the segment of the knot portion 237A in a different second stage of the deployed configuration that is limited to axial compression of the knot portion 237A.

With reference to FIG. 3A where the knot portion 237A is in the delivery configuration, the locking functionality of the knot portion 237A can be decomposed into multiple locking portions that individually provide forces against the suture portions 232, 234 disposed therebetween. For example, a first portion 237A-1 provides a first force component Fa1, a second portion 237A-2 provides a second force component Fb1, and a third portion 237A-3 provides a third force component Fc1. Note that the three portions 237A-1, 237A-2, 237A-3 and their respective associated force components Fa1, Fb1, Fc1 represent example locations from which forces are applied by the knot portion 237A of the locking suture 237. It should be understood, however, that in practice the knot portion 237A can provide circumferentially continuous compressive, constrictive, or locking force components or vectors about the suture portions 232, 234, as more clearly evident in embodiments described herein.

The arrow A represents a direction of allowable movement or translation of the suture portions 232, 234 relative to the knot portion 237A when in the delivery configuration. That is, in the delivery configuration the locking suture 237 is sufficiently loosely wound, wrapped, and/or coiled around the suture portions 232, 234 in an elongated manner that the locking suture 237 can be moved along the suture portions 232, 234. This can be done, for example, to deliver the locking suture 237 into the target region TR and towards the tissues T1, T2 (which is described in greater detail herein with reference to FIGS. 2A and 2B). With the knot portion 237A delivered to a targeted location, the locking suture 237 can be deployed or transitioned into a tightened, bulky, bunched, or looped knot configuration. This can be accomplished, for example, by approximating opposite ends of the winds or coils of the locking suture 237 towards each other.

During deployment, the coils, wraps, loops, turns, or portions of the knot portion 237A disposed about the suture portions 232, 234 are tightened, shortened, and/or constricted, resulting in a restrained or confined tortuous path for the suture portions 232, 234, as illustrated conceptually in FIGS. 3B, 3C, and 3D. With reference to FIG. 3B, the magnitude of the force components Fa2, Fb2, Fc2 applied by the respective portions 237A-1, 237A-2, 237A-3 of the knot portion 237A in the first stage of its deployed configuration is greater than a magnitude of the force components Fa1, Fb1, Fc1 in the delivery configuration shown in FIG. 3A, resulting in the respective locking suture portions 237A-1, 237A-2, 237A-3 moving towards the suture portions 232, 234, e.g., towards axis B. This biases the suture portions 232, 234 into a tortuous configuration. Said another way, during the first stage of deployment, the knot portion 237A is radially compressed about the suture portions 232, 234 by opposing forces, e.g., forces Fa2 and Fc2 oppose force Fb2, thereby increasing the friction between the knot portion 237A and the suture portions 232, 234 and restricting relative movement therebetween. To deploy this first stage and radially compress the knot portion 237A about the suture portions 232, 234, one strand or free end of the tether portion 237B can be pulled or withdrawn proximally. Such radial compression is illustrated by the opposing movements of the first and third locking portions 237A-1 237A-3 relative to the second locking portion 237A-2. After the first stage, a second stage of deployment can include pulling on the other strand or free end of the tether portion 237B to laterally or angularly deflect the first portion 237A-1 (e.g., along arrow C, about the B axis, and/or about the second portion 237A-2) to create a bulky or looped configuration to further secure and inhibit relative movement of the suture portions 232, 234, as illustrated in FIG. 3C. In some embodiments, examples of which are illustrated in FIG. 3D, the second stage of deployment can involve only axial compression of knot portion 237A, e.g., reducing the axial spacing of first, second, and third locking portions 237A-1, 237A-2, and 237A-3 along axis B. With the knot portion 237A sufficiently secured to the suture portions 232, 234 in this manner, the free ends of the suture portions 232, 234 and the tether portion 237B can be dealt with in any suitable manner. For example, in some instances, the free ends of the suture portions 232, 234 and the tether portion 237B can be secured outside the target region (e.g., to an external surface of the heart).

Although the above embodiment with respect to the LS delivery device 246 describes a method using examples dealing with a cardiac procedure, the methods and devices described herein are readily adaptable for various types of tissue repair procedures. For ease of explanation, embodiments described herein are described with respect to repairing a cardiac mitral valve. It should be understood, however, that the devices and methods described herein can be used to repair other cardiac valves, such as a tricuspid, aortic, or pulmonic valve, or non-valvular cardiac tissue, such as heart walls and/or septa, or non-cardiac tissues, such as in orthopedic applications where two or more tissues are to be approximated. Similarly, the devices and methods described herein can be used in applications in which two or more sutures or the like are to be approximated, knotted, joined, and/or secured together. In connection with cardiac surgery, for example, in a procedure in which artificial cords are secured to a native valve leaflet and/or annulus, the free ends of the cords may extend outside the heart. With the free ends of the cords disposed outside the heart, the devices and methods described herein can be used to secure the cords together outside the heart, and optionally, for example, to a pledget or similar anchor.

In some embodiments, for example, apparatus and methods are described herein for remotely securing two or more sutures together within a non-invasive procedure to repair a cardiac valve. In some embodiments, apparatus and methods are described herein for performing a non-invasive procedure for repairing a mitral valve using an edge-to-edge stitch (also referred to as an Alfieri procedure) to secure two mitral valve leaflets together.

Figure 4:
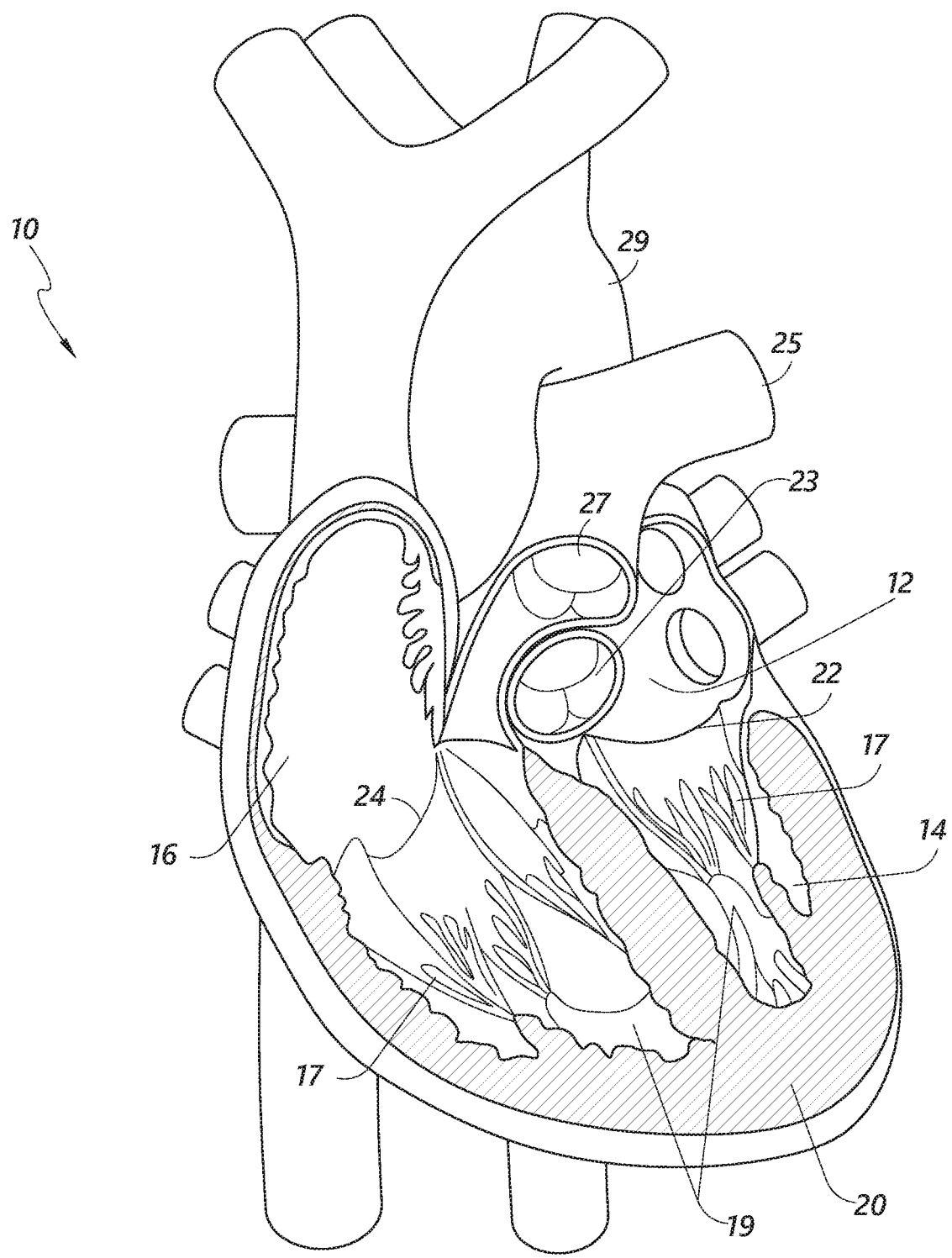
FIG. 4 illustrates a cut-away anterior view of a heart, showing the internal chambers, valves and adjacent structures.

As illustrated in FIG. 4, the human heart 10 has four chambers, which include two upper chambers denoted as atria 12, 16 and two lower chambers denoted as ventricles 14, 18. A septum 20 (see, e.g., FIG. 6) divides the heart 10 and separates the left atrium 12 and left ventricle 14 from the right atrium 16 and right ventricle 18. The heart further contains four valves 22, 23, 26, and 27. The valves function to maintain the pressure and unidirectional flow of blood through the body and to prevent blood from leaking back into a chamber from which it has been pumped.

Two valves separate the atria 12, 16 from the ventricles 14, 18, denoted as atrioventricular valves. The mitral valve 22, also known as the left atrioventricular valve, controls the passage of oxygenated blood from the left atrium 12 to the left ventricle 14. A second valve, the aortic valve 23, separates the left ventricle 14 from the aortic artery (aorta) 29, which delivers oxygenated blood via the circulation to the entire body. The aortic valve 23 and mitral valve 22 are part of the "left" heart, which controls the flow of oxygen-rich blood from the lungs to the body. The right atrioventricular valve, the tricuspid valve 24, controls passage of deoxygenated blood into the right ventricle 18. A fourth valve, the pulmonary valve 27, separates the right ventricle 18 from the main pulmonary artery 25. The right ventricle 18 pumps deoxygenated blood through the pulmonary artery 25 to the lungs wherein the blood is oxygenated and then delivered to the left atrium 12 via the pulmonary vein. Accordingly, the tricuspid valve 24 and pulmonic valve 27 are part of the right heart, which control the flow of oxygen-depleted blood from the body to the lungs.

Both the left and right ventricles 14, 18 constitute pumping chambers. The aortic valve 23 and pulmonic valve 27 lie between a pumping chamber (ventricle) and a major artery and control the flow of blood out of the ventricles and into the circulation. The aortic valve 23 and pulmonic valve 27 have three cusps, or leaflets, that open and close and thereby function to prevent blood from leaking back into the ventricles after being ejected into the lungs or aorta 29 for circulation.

Both the left and right atria 12, 16 are receiving chambers. The mitral valve 22 and tricuspid valve 24, therefore, lie between a receiving chamber (atrium) and a ventricle so as to control the flow of blood from the atria to the ventricles and prevent blood from leaking back into the atrium during ejection from the ventricle. Both the mitral valve 22 and tricuspid valve 24 include two or more cusps, or leaflets (not shown in FIG. 4), that are encircled by a variably dense fibrous ring of tissues known as the annulus (not shown in FIG. 4). The valves are anchored to the walls of the ventricles by chordae tendineae (chordae) 17. The chordae tendineae 17 are cord-like tendons that connect the papillary muscles 19 to the leaflets (not shown in FIG. 4) of the mitral valve 22 and tricuspid valve 24 of the heart 10. The papillary muscles 19 are located at the base of the chordae tendineae 17 and are within the walls of the ventricles. The papillary muscles 19 do not open or close the valves of the heart, which close passively in response to pressure gradients; rather, the papillary muscles 19 brace the valves against the high pressure needed to circulate the blood throughout the body. Together, the papillary muscles 19 and the chordae tendineae 17 are known as the sub-valvular apparatus. The function of the sub-valvular apparatus is to keep the valve leaflets from prolapsing into the atria when they close.

Figure 5A:
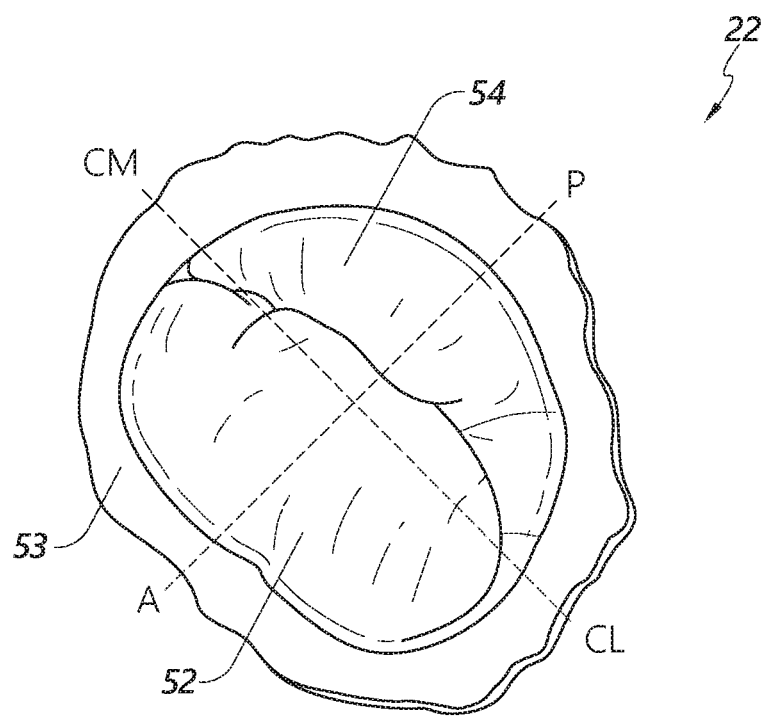
FIG. 5A illustrates a top perspective view of a healthy mitral valve with the mitral leaflets closed.

The mitral valve 22 is illustrated in FIG. 5A. The mitral valve 22 includes two leaflets, the anterior leaflet 52 and the posterior leaflet 54, and a diaphanous incomplete ring around the valve, called the annulus 53. The mitral valve 22 has two papillary muscles 19, the anteromedial and the posterolateral papillary muscles (see, e.g., FIG. 4), which attach the leaflets 52, 54 to the walls of the left ventricle 14 via the chordae tendineae 17 (see, e.g., FIG. 4).

Figure 5B:
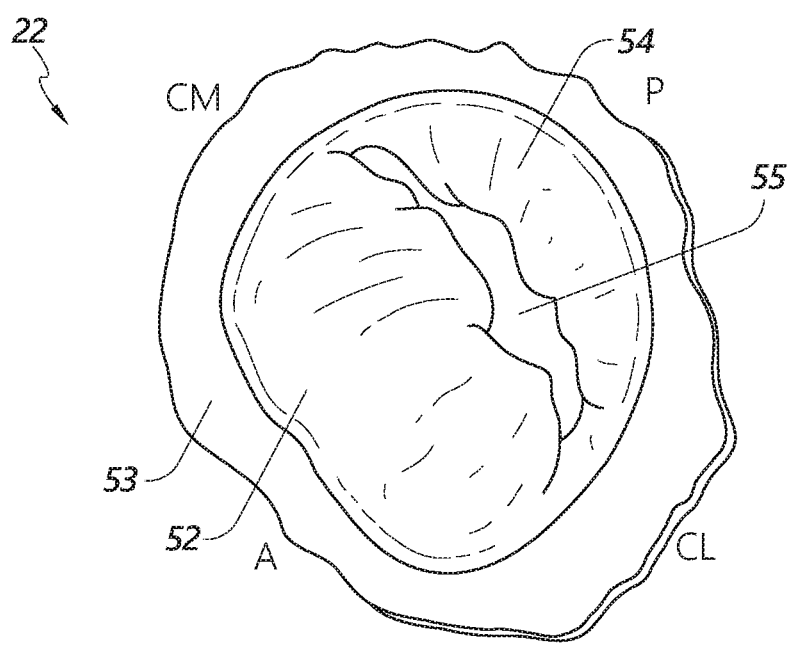
FIG. 5B illustrates a top perspective view of a dysfunctional mitral valve with a visible gap between the mitral leaflets.
Figure 5C:
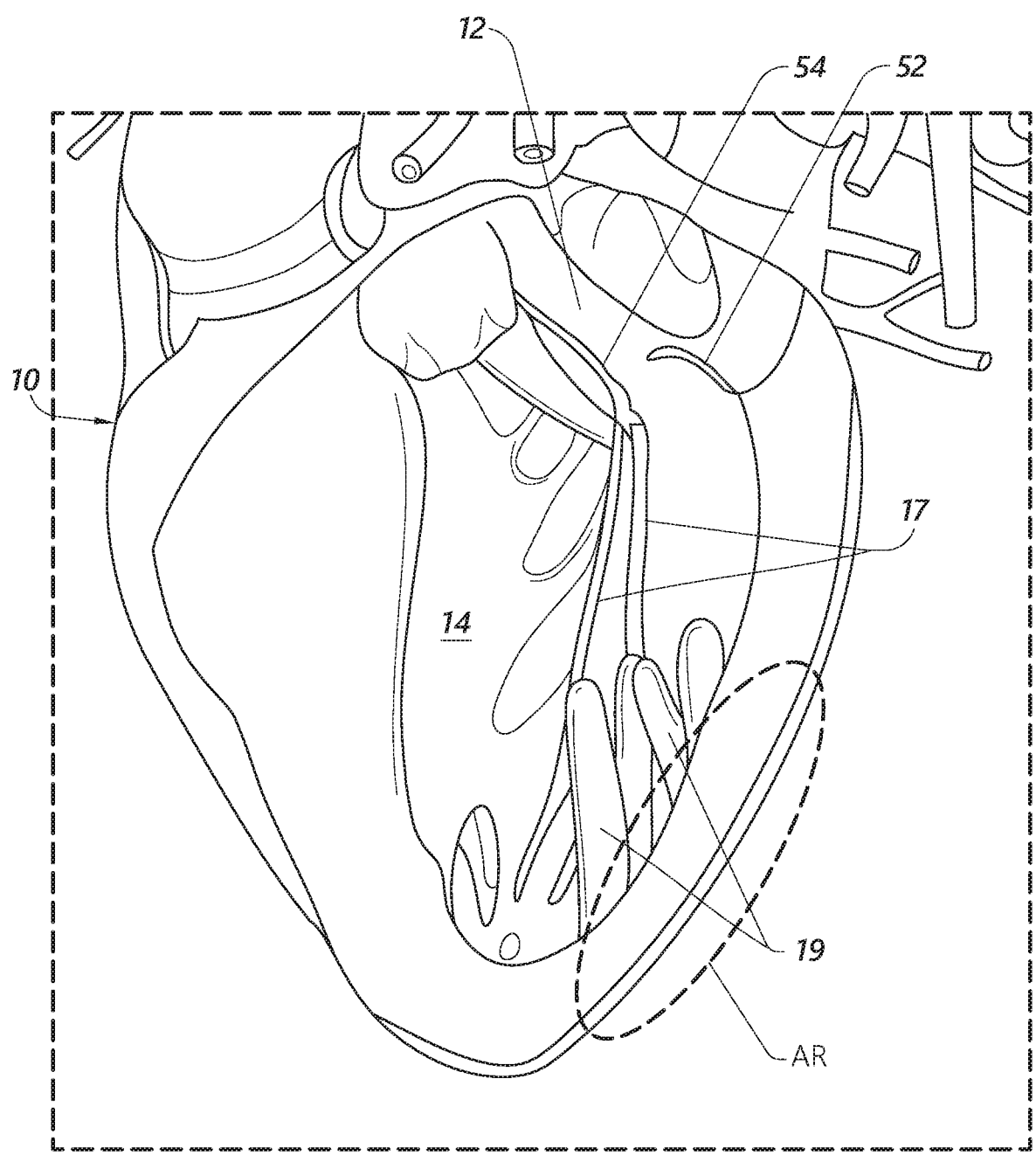
FIG. 5C illustrates a cross-sectional view of a heart illustrating a mitral valve prolapsed into the left atrium.
Figure 5D:
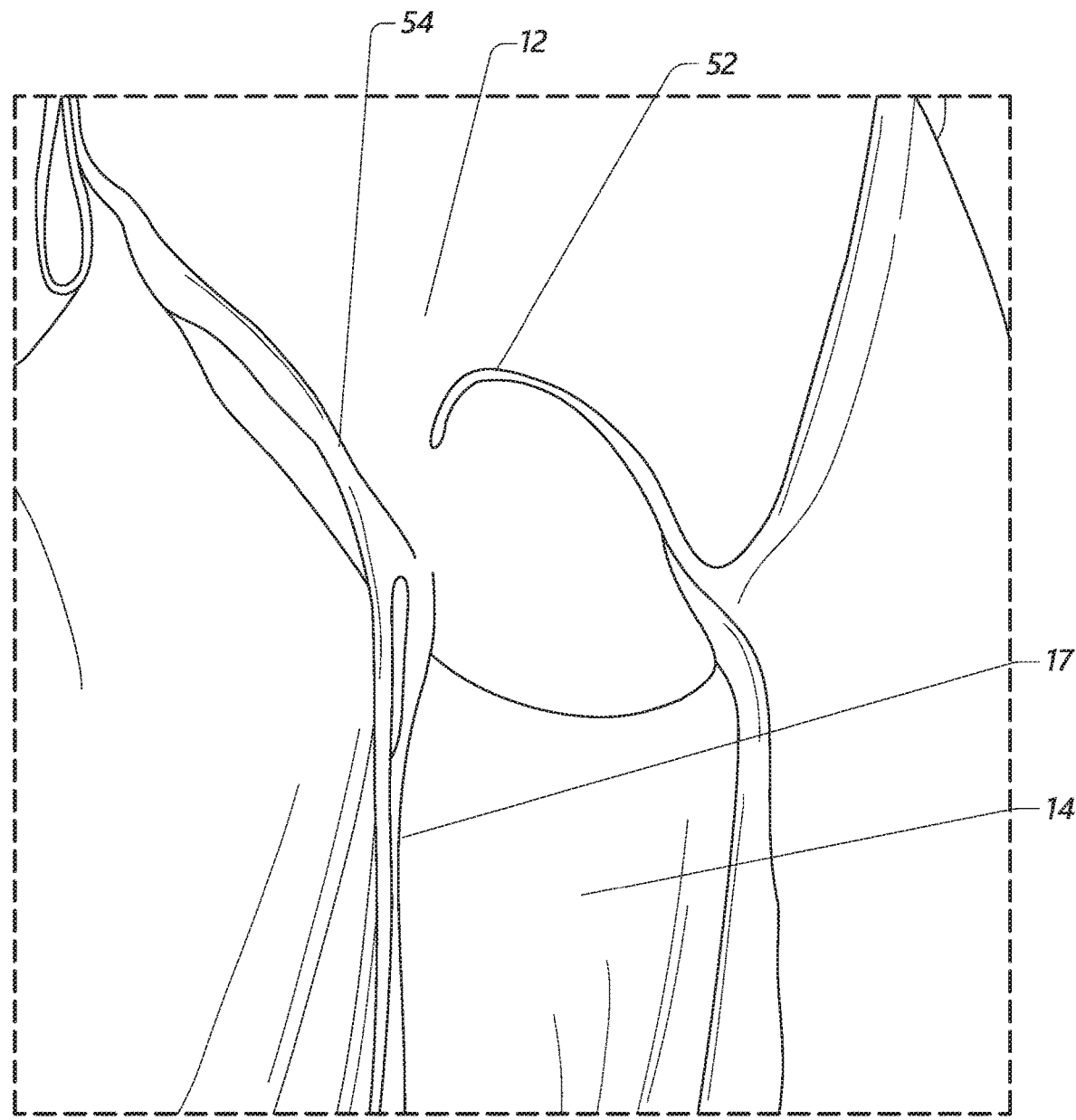
FIG. 5D illustrates an enlarged view of the prolapsed mitral valve of FIG. 5C.

FIG. 5B illustrates a prolapsed mitral valve 22. As can be seen with reference to FIG. 5B-5D, prolapse occurs when a prolapsed segment of a leaflet 52, 54 of the mitral valve 22 is displaced above the plane of the mitral annulus into the left atrium 12 (see FIGS. 5C and 5D) preventing the leaflets from properly sealing together to form the natural plane or line of coaptation between the valve leaflets during systole. Because one or more of the leaflets 52, 54 malfunctions, the mitral valve 22 does not close properly, and, therefore, the leaflets 52, 54 fail to coapt. This failure to coapt causes a gap 55 between the leaflets 52, 54 that allows blood to flow back into the left atrium, during systole, while it is being ejected by the left ventricle. As set forth above, there are several different ways a leaflet may malfunction, which can thereby lead to regurgitation.

Mitral valve regurgitation increases the workload on the heart and may lead to very serious conditions if left untreated, such as decreased ventricular function, pulmonary hypertension, congestive heart failure, permanent heart damage, cardiac arrest, and ultimately death. Since the left heart is primarily responsible for circulating the flow of blood throughout the body, malfunction of the mitral valve 22 is particularly problematic and often life threatening.

As described in detail in the '761 PCT Application and the '170 PCT Application, methods and devices are provided for performing non-invasive procedures to repair a cardiac valve, such as a mitral valve. Such procedures include procedures to repair regurgitation that occurs when the leaflets of the mitral valve do not coapt at peak contraction pressures, resulting in an undesired back flow of blood from the ventricle into the atrium. As described in the '761 PCT Application and the '170 PCT Application, after the malfunctioning cardiac valve has been assessed and the source of the malfunction verified, a corrective procedure can be performed. Various procedures can be performed in accordance with the methods described therein to effectuate a cardiac valve repair, which will depend on the specific abnormality and the tissues involved.

After preparing and placing the subject under anesthesia, a transesophageal echocardiogram (TEE) (2D or 3D), a transthoracic echocardiogram (TTE), intracardiac echo (ICE), or cardio-optic direct visualization (e.g., via infrared vision from the tip of a 7.5 F catheter) may be performed to assess the heart and its valves.

After a minimally invasive approach is determined to be advisable, one or more incisions are made proximate to the thoracic cavity to provide a surgical field of access. The total number and length of the incisions to be made depend on the number and types of the instruments to be used as well as the procedure(s) to be performed. The incision(s) should be made in such a manner to be minimally invasive. As referred to herein, the term minimally invasive means in a manner by which an interior organ or tissue may be accessed with as little as possible damage being done to the anatomical structure through which entry is sought. Typically, a minimally invasive procedure is one that involves accessing a body cavity by a small incision of, for example, approximately 5 cm or less made in the skin of the body. The incision may be vertical, horizontal, or slightly curved. If the incision is placed along one or more ribs, it should follow the outline of the rib. The opening should extend deep enough to allow access to the thoracic cavity between the ribs or under the sternum and is preferably set close to the rib cage and/or diaphragm, dependent on the entry point chosen.

In one example method, the heart may be accessed through one or more openings made by a small incision(s) in a portion of the body proximal to the thoracic cavity, for example, between one or more of the ribs of the rib cage of a patient, proximate to the xyphoid appendage, or via the abdomen and diaphragm. Access to the thoracic cavity may be sought to allow the insertion and use of one or more thorascopic instruments, while access to the abdomen may be sought to allow the insertion and use of one or more laparoscopic instruments. Insertion of one or more visualizing instruments may then be followed by transdiaphragmatic access to the heart. Additionally, access to the heart may be gained by direct puncture (e.g., via an appropriately sized needle, for instance an 18-gauge needle) of the heart from the xyphoid region. Accordingly, the one or more incisions should be made in such a manner as to provide an appropriate surgical field and access site to the heart in the least invasive manner possible. Access may also be achieved using percutaneous methods further reducing the invasiveness of the procedure. See, for instance, "Full-Spectrum Cardiac Surgery Through a Minimal Incision Mini-Sternotomy (Lower Half) Technique," Doty et al., *Annals of Thoracic Surgery* 1998; 65(2): 573-7 and "Transxiphoid Approach Without Median Sternotomy for the Repair of Atrial Septal Defects," Barbero-Marcial et al., *Annals of Thoracic Surgery* 1998; 65(3): 771-4, the entire disclosures of each of which are incorporated herein by reference.

Once a suitable entry point has been established, the surgeon can use one or more sutures to make a series of stiches in one or more concentric circles in the myocardium at the desired location to create a "pursestring" closure. The Seldinger technique can be used to access the left ventricle in the area surrounded by the pursestring suture by puncturing the myocardium with a small sharp hollow needle (a "trocar") with a guidewire in the lumen of the trocar. Once the ventricle has been accessed, the guidewire can be advanced, and the trocar removed. A valved-introducer with dilator extending through the lumen of the valved-introducer can be advanced over the guidewire to gain access to the left ventricle. The guidewire and dilator can be removed and the valved-introducer will maintain hemostasis, with or without a suitable delivery device inserted therein, throughout the procedure. Alternatively, the surgeon can make a small incision in the myocardium and insert the valved-introducer into the heart via the incision. Once the valved-introducer is properly placed the pursestring suture is tightened to reduce bleeding around the shaft of the valved-introducer.

A suitable device such as a delivery device described in the '761 PCT Application and/or the '170 PCT Application, may be advanced into the body and through the valved-introducer in a manner to access the left ventricle. The advancement of the device may be performed in conjunction with sonography or direct visualization (e.g., direct trans-blood visualization). For example, the delivery device may be advanced in conjunction with TEE guidance or ICE to facilitate and direct the movement and proper positioning of the device for contacting the appropriate apical region of the heart. Typical procedures for use of echo guidance are set forth in Suematsu.

Figure 6:
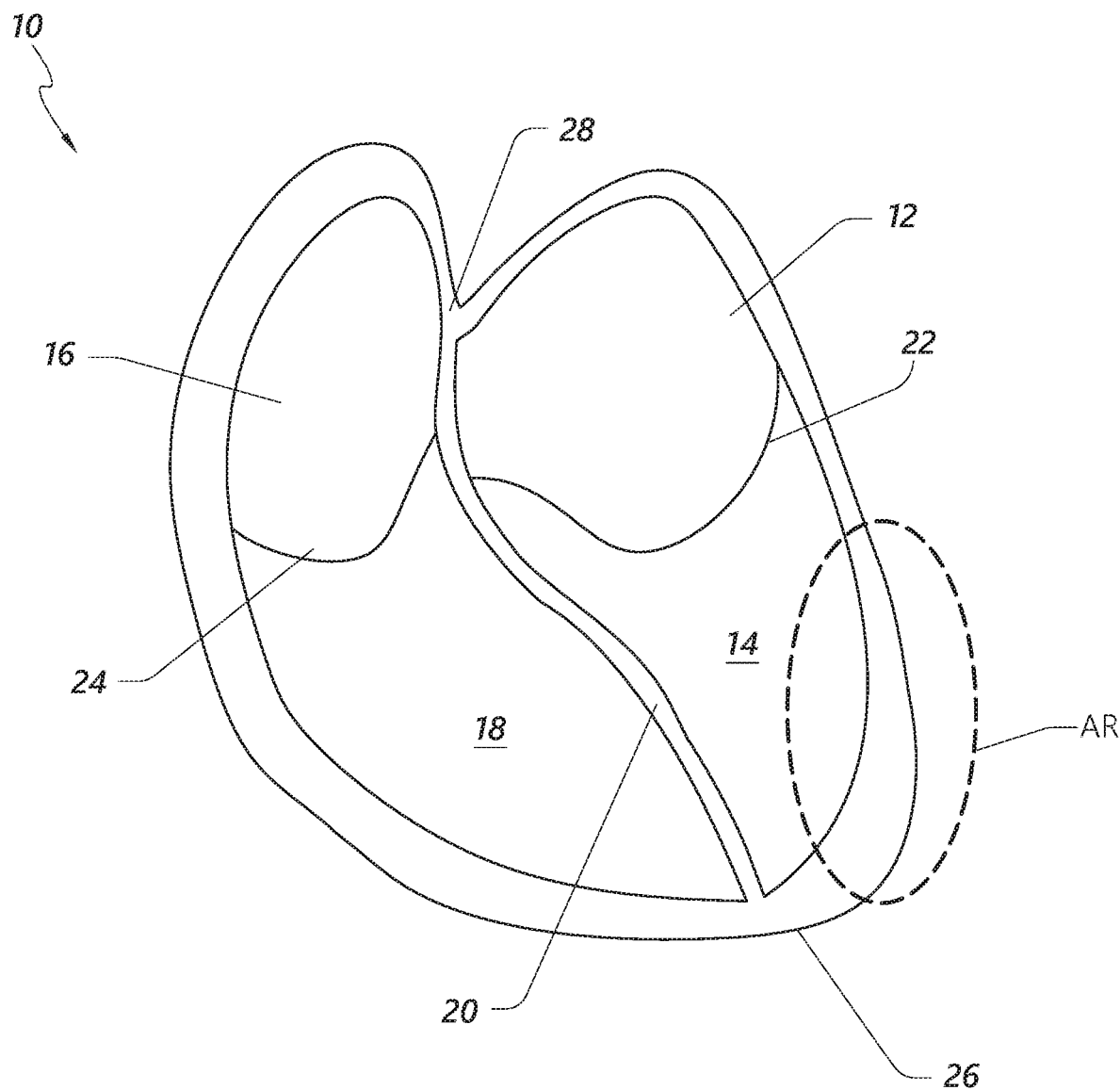
FIG. 6 illustrates a cross-sectional view of a heart showing the left atrium, right atrium, left ventricle, right ventricle and the apex region.

As shown in FIG. 6, one or more chambers, e.g., the left atrium 12, left ventricle 14, right atrium 16, or right ventricle 18 in the heart 10 may be accessed in accordance with the methods disclosed herein. Access into a chamber 12, 14, 16, 18 in the heart 10 may be made at any suitable site of entry but is preferably made in the apex region of the heart, for example, slightly above the apex 26 at the level of the papillary muscles 19 (see also FIG. 5C). Typically, access into the left ventricle 14, for instance, to perform a mitral valve repair, is gained through the process described above performed in the apical region, close to (or slightly skewed toward the left of) the median axis 28 of the heart 10. Typically, access into the right ventricle 18, for instance, to perform a tricuspid valve repair, is gained through the process described above performed in the apical region, close to or slightly skewed toward the right of the median axis 28 of the heart 10. Generally, an apex region of the heart is a bottom region of the heart that is within the left or right ventricular region and is below the mitral valve 22 and tricuspid valve 24 and toward the tip or apex 26 of the heart 10. More specifically, an apex region AR of the heart (see, e.g., FIG. 6) is within a few centimeters to the right or to the left of the septum 20 of the heart 10 at or near the level of the papillary muscles 19. Accordingly, the ventricle can be accessed directly via the apex 26, or via an off-apex location that is in the apical or apex region AR, but slightly removed from the apex 26, such as via a lateral ventricular wall, a region between the apex 26 and the base of a papillary muscle 19, or even directly at the base of a papillary muscle 19 or above. Typically, the incision made to access the appropriate ventricle of the heart is no longer than about, for example, about 0.5 cm. Alternatively, access can be obtained using the Seldinger technique described above.

The mitral valve 22 and tricuspid valve 24 can be divided into three parts: an annulus (see 53 in FIGS. 5A and FB), leaflets (see 52, 54 in FIGS. 5A and 5B), and a sub-valvular apparatus. The sub-valvular apparatus includes the papillary muscles 19 (see FIG. 4) and the chordae tendineae 17 (see FIG. 4), which can elongate and/or rupture. If the valve is functioning properly, when closed, the free margins or edges of the leaflets come together and form a tight junction, the arc of which, in the mitral valve, is known as the line, plane, or area of coaptation. Normal mitral and tricuspid valves open when the ventricles relax allowing blood from the atrium to fill the decompressed ventricle. When the ventricle contracts, chordae tendineae properly position the valve leaflets such that the increase in pressure within the ventricle causes the valve to close, thereby preventing blood from leaking into the atrium and assuring that all of the blood leaving the ventricle is ejected through the aortic valve (not shown) and pulmonic valve (not shown) into the arteries of the body. Accordingly, proper function of the valves depends on a complex interplay between the annulus, leaflets, and sub-valvular apparatus. Lesions in any of these components can cause the valve to dysfunction and thereby lead to valve regurgitation. As set forth herein, regurgitation occurs when the leaflets do not coapt properly at peak contraction pressures. As a result, an undesired back flow of blood from the ventricle into the atrium occurs.

Although the procedures described herein are with reference to repairing a cardiac mitral valve or tricuspid valve by the implantation of one or more artificial chordae, the methods presented are readily adaptable for various types of tissue, leaflet, and annular repair procedures. The methods described herein, for example, can be performed to selectively approximate two or more portions of tissue to limit a gap between the portions. In general, the methods herein are described with reference to a mitral valve 22 but should not be understood to be limited to procedures involving the mitral valve.

Example Devices for Approximating Tissues

Figure 7:
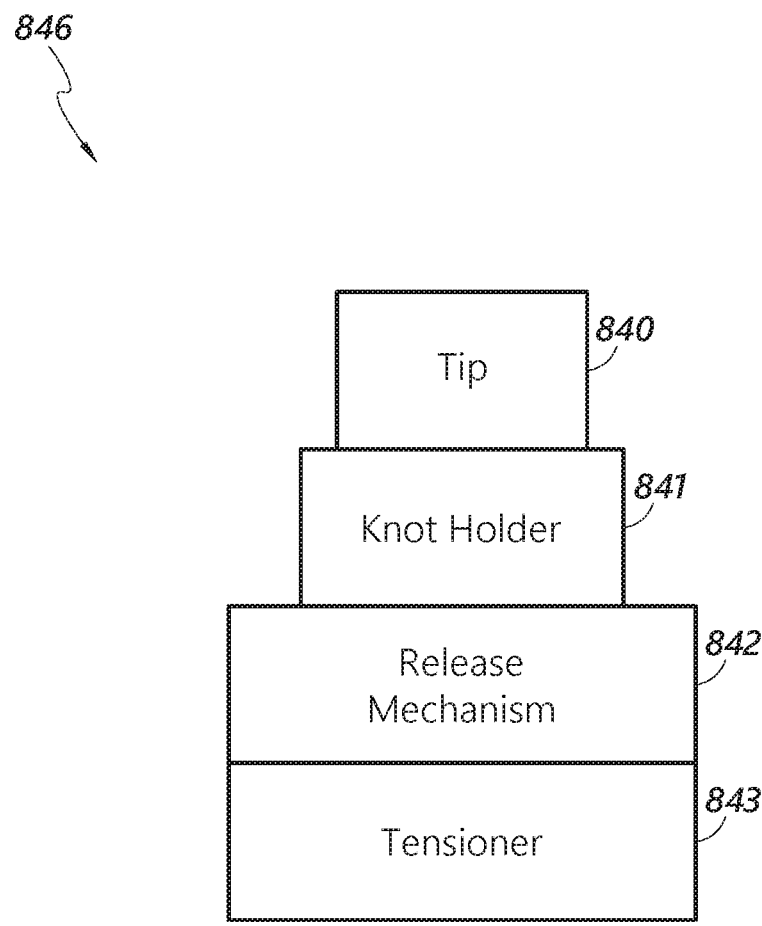
FIG. 7 illustrates a block diagram of an example LS delivery device having a knot holder and atraumatic tip with a tensioner and release mechanism.

FIG. 7 illustrates a block diagram of an example LS delivery device 846 having a knot holder 841 and atraumatic tip 840 with a tensioner 843 and release mechanism 842. The LS delivery device 846 is configured to secure a pre-formed locking suture to allow one or more suture ends to be passed through or interweaved with the locking suture, to maneuver the locking suture with suture ends to a targeted location, to allow the suture ends to be adjusted, to tension the locking suture to lock the suture ends (e.g., to inhibit relative motion between the suture tails and the locking suture), and to release the locking suture in its deployed or locked state.

The LS delivery device 846 includes the atraumatic tip 840 attached to the knot holder 841. The atraumatic tip 840 can be the most distal component of the LS delivery device 846 so that as the LS delivery device 846 advances the locking suture little or no damage is done to the tissue in the target region, such as a valve leaflet. The atraumatic tip 840 can be made of a tissue-friendly material that is pliable and/or relatively dull to prevent or reduce the likelihood of tissue damage when the LS delivery device 846 is in the process of delivering the locking suture to its targeted location.

The knot holder 841 is configured to secure the locking suture in its pre-deployment or delivery configuration. The knot holder 841 can be a needle holder and/or a knot holder, where the needle holder secures a needle that is used to hold or secure the locking suture in place during a portion of a procedure using the locking suture. For example, a needle can be used to hold a locking suture while suture tail ends are interweaved or inserted through the locking suture, after which the needle can be removed leaving the locking suture with the suture tail ends in a delivery configuration. An example of this configuration is described herein with reference to FIGS. 18A-18K.

The knot holder 841 can be configured to push off the locking suture as part of deployment or the transition from a delivery state to a deployed state. The knot holder 841 can be configured to pull back the holder so that the locking suture slides off the LS delivery device 846. For example, the knot holder 841 can include an outer tube with a flexible feature at a distal end (where the flexible feature functions as the atraumatic tip 840). In some embodiments, the LS delivery device 846 can secure a loose locking suture or a locking suture in a delivery configuration that allows suture tail ends to be threaded through the locking suture using the knot holder 841 wherein the knot holder includes a needle holder. Once the locking suture and suture tail ends are sufficiently intertwined, the needle holder can be removed leaving the locking suture secured to the flexible distal end of the outer tube for delivery.

In some embodiments, the knot holder 841 secures the knot in place without a tip 840 in such a way that the knot goes before the knot holder 841, the knot therefore providing protection against tissue damage. In some embodiments, the knot holder 841 also includes tissue-friendly characteristics so that the knot holder 841 and the atraumatic tip 840 are combined. An example of such a configuration is described herein with reference to FIGS. 18A-18K (see, e.g., FIG. 18J).

The LS delivery device 846 includes a tensioner 843 that is configured to apply tension to the ends of the locking suture to transition the locking suture from a delivery configuration to a deployed configuration. The transition from the delivery configuration to the deployed configuration includes tightening the locking suture to inhibit relative motion between the locking suture and the suture tail ends. Examples of components of the tensioner 843 include, but are not limited to, a pinion wheel, a loaded spring, gears, grips to allow manually pulling the locking suture tethers, and the like.

The tensioner 843 is configured so that, advantageously, application of tension to a knot portion of the locking suture does not alter or increase proximal tension on suture tail ends intertwined with the knot portion. For example, the knot holder 841 can be configured so that the tensioner 843 applies force to a tether portion of the locking suture and the knot holder 841 directs the applied force to cause the knot portion to tighten while not pulling proximally on the suture tail ends. This can be accomplished, at least in part, by fixing the knot portion in place with the knot holder 841 while it is being tightened. This can be accomplished, at least in part, by configuring the knot holder 841 so that it re-directs tension on the tether portion at an angle relative to the knot portion of the locking suture.

The tensioner 843 can be configured to provide mechanical advantages when tensioning the tethers of the locking suture. For example, the tensioner 843 can be configured to provide a targeted tension. As another example, the tensioner 843 can be configured to prevent or inhibit the application of too much force to prevent over-tensioning the locking suture. The tensioner 843 may include one or more sensors configured to determine or measure the amount of tension on the locking suture tethers. The tensioner 843 may also include feedback systems or user interface features to indicate when a targeted tension has been achieved (or exceeded). Examples include gauges, readouts, indicator lights (e.g., green, yellow, and red lights), and the like. The tensioner 843 may include a mechanism for allowing a user to dial, set, or enter a targeted tension. The tensioner 843 can then provide that targeted tension to improve repeatability and reliability of the LS delivery device 846.

The tensioner 843 can be a multi-stage device that provides forces at different times. For example, the tensioner 843 can be configured to sequentially tension or apply force to the ends of the locking suture. As another example, the tensioner 843 can be configured to apply a first force to a first locking suture end (e.g., a first tether) and at a later time to apply a second force to a second locking suture end (e.g., a second tether). In this way, the tensioner can be configured to apply a targeted force to each tether of the locking suture to achieve a targeted locking force on the suture tail ends. In some embodiments, the tensioner 843 is configured to apply at least about 5 N and/or less than or equal to about 40 N, at least about 7 N and/or less than or equal to about 35 N, or at least about 10 N and/or less than or equal to about 30 N on an individual tether of the locking suture. In some embodiments, prior to deployment, the locking suture can be configured to slide along the suture tails with the application of at least 3 N of force and/or less than or equal to about 13 N of force, at least 4 N of force and/or less than or equal to about 10 N of force, or at least 5 N of force and/or less than or equal to about 7.5 N of force.

The LS delivery device 846 also includes a release mechanism 842. The release mechanism 842 is configured to cause the knot holder 841 to release the locking suture after it has transitioned to a deployed state. The release mechanism 843 is configured to interface or interact with the tensioner 843 and/or the knot holder 841 to cause these components to release the locking suture. The release mechanism 842 can be manually activated by a user or it can be configured to automatically release the locking suture after the locking suture has been tightened by the tensioner. In some embodiments, the release mechanism 842 includes one or more user interface features to allow the user to control when the release mechanism 843 releases the locking suture and suture tail ends.

Example Methods of Approximating Tissues

Figure 8:
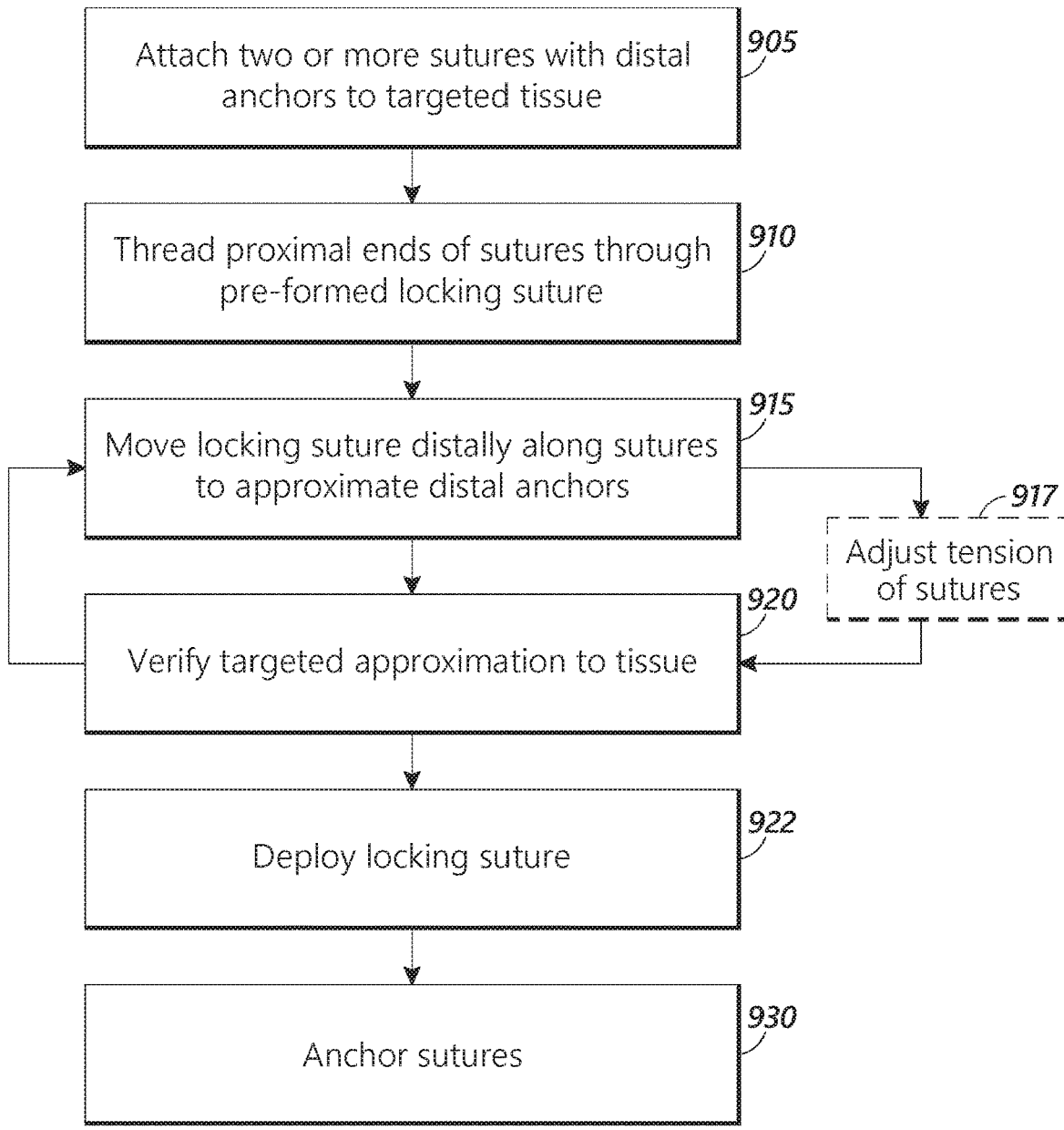
FIG. 8 illustrates a flow chart of an example method for securing a locking suture to approximate distal anchors attached to tissue

FIG. 8 illustrates a flow chart of an example method 900 for securing a locking suture to approximate distal anchors attached to tissue. The method 900 can be used with any of the LS delivery devices disclosed herein. The method 900 can be used to approximate any tissue that can receive an anchor implant (e.g., a bulky knot implant) with a suture attached thereto. Examples provided herein focus on implanting artificial tendineae, but other procedures may utilize the method 900. Where the term anchor is used herein, it is to be understood that an anchor refers to any suitable component or element that serves to anchor a suture to tissue such as, for example and without limitation, hooks, barbs, knots (e.g., bulky knots), and the like.

In some embodiments, the method 900 improves upon existing Alfieri procedures by sliding a locking suture to adjust the tension and direction of force vectors applied to tissues to be approximated. Advantageously, the method 900 allows an operator (e.g., a physician or surgeon) a way to change force vectors applied by anchor implants in tissue. For example, when implanting artificial chordae tendineae, the knot that coalesces a plurality of the sutures or cords can be adjusted to be at any location from the apex of the heart to the valve with the implanted cords. This can be used to adjust both the angle of the force vectors as well as the magnitude of the force vectors, providing increased control to the operator.

At step 905, two or more artificial cords are attached to targeted tissue. The artificial cords include anchor implants at a distal end that are anchored to the targeted tissue, e.g., a posterior or anterior leaflet. The cords also include sutures extending proximally from the anchor implants. These sutures extend proximally from the implants to a region away and/or outside of the targeted region. In some embodiments, the targeted region is within the heart or within a chamber of the heart (e.g., the left ventricle).

At step 910, the proximal ends or portions of the sutures are threaded through a pre-formed locking suture. The sutures can be threaded through various strands of the locking suture or the sutures can be threaded through a central lumen or corridor of the locking suture. The locking suture can be attached or secure to a LS delivery device, such as any of the LS delivery devices described herein. The LS delivery device can be configured to deploy and release the locking suture after approximation of the targeted tissue.

The pre-formed locking suture can be any of the locking sutures described herein. In some embodiments, the pre-formed locking suture includes a knot formed from a suture wherein the knot includes a plurality of cow hitches with ends of the knot suture being threaded through portions of the plurality of cow hitches so that, when the ends of the knot suture are tensioned, they axially and radially constrict to create a tortuous path for any suture tail ends threaded through the locking suture. In this way, the suture tail ends and the locking suture are inhibited or prevented from relative movement.

At step 915, the locking suture with the suture tail ends intertwined is moved along the sutures toward and/or away from the distal anchors and the targeted tissue. Moving, sliding, or otherwise translating the locking suture in its delivery configuration can be accomplished using an LS delivery device. The device can push and pull the locking suture to a targeted location. This can be monitored and confirmed using various imaging techniques.

Moving the locking suture towards the targeted tissue causes the implants (and the tissues) to approximate. By moving the locking suture distally (e.g., pushing), the targeted tissue can be approximated. Similarly, by moving the locking suture proximally (e.g., pulling), the approximation of the tissues can be decreased. Thus, the LS delivery device allows an operator to control approximation of the distal anchors and, consequently, the targeted tissue.

In addition, sliding the locking suture along the suture tails causes a point of intersection of the sutures to move closer to the targeted tissues. This adjusts the angles of the forces applied to the implants, and therefore to the tissue.

At optional step 917, the tension of the sutures can be adjusted. This can be done, for example, by pulling proximally on the suture tail ends. This can be done in conjunction with sliding the locking suture to tailor the force vectors on the implants to achieve targeted tissue approximation. For example, sliding the locking suture can be done simultaneously with pulling (or releasing tension) on the sutures to achieve targeted force vectors and/or targeted tissue approximation.

At step 920, imaging or other methods are used to verify that the targeted approximation of the tissues has been achieved. This feedback step allows the operator to iteratively adjust the position of the locking suture and/or the amount of tension on the sutures (e.g., as provided in optional step 517). The iterative nature of this portion of the method 900 is illustrated using an arrow that goes from step 920 back to step 915. Imaging methods include cardiac ultrasound and echo guidance, as described herein.

Once the targeted approximation of the targeted tissue has been achieved, the locking suture is deployed at step 922. Deployment of the locking suture includes applying tension to individual tethers of the locking suture. As described herein, the tension can be applied at different times (e.g., sequentially) and/or with different forces to achieve sufficient or targeted locking of the locking suture. The LS delivery device can be used to tension the locking suture and release it after tensioning. The LS delivery device can be configured so that tension applied to individual tethers of the locking suture does not alter or increase the tension on the distal anchors and the targeted tissue. For example, the knot portion can be secured in place by the LS delivery device while tension is applied to the tether portion to limit or prevent movement of the knot portion relative to the two or more sutures during deployment of the locking suture.

At step 930, the locked sutures are anchored. The anchoring step is done to prevent or to reduce the likelihood that the locked sutures will come loose. The sutures can be anchored to a tissue wall, such as an external wall of the heart. A pledget can be used as the anchor. For example, PTFE (Teflon®, DuPont, Wilmington, Del.) felt can be used as an anchor where the felt is attached to the tissue wall. In some embodiments, the anchor includes a plurality of holes through which the sutures extend. Knots and/or additional locking sutures can be used to anchor the sutures.

Advantageously, the locking suture is configured to be able to be moved or slid from outside of the target region. This can allow greater accessibility and flexibility to operators performing the procedure. Another advantage of the method 900 is that it is adjustable. The method 900 also allows for real-time adjustment of tissue approximation to achieve coaptation between leaflets because an operator can adjust the tension of the sutures, and by extension the approximation of the implants and targeted tissue, based on feedback from a visualization system (e.g., cardiac ultrasound).

The method 900 also provides other advantages over other approaches to addressing MR. For example, implanting a clip in the mitral valve to address MR does not provide adjustability. In contrast, the method 900 allows for real-time adjustability. Furthermore, the method 900 can be accomplished using real-time imaging or other feedback to reduce or eliminate MR. This allows an operator to see the effects of the procedure in real time allowing for the operator to make adjustments to achieve targeted results. In addition, if reoperation is required the valve is unaffected by the method 900 whereas a mitral valve clip may destroy or damage the tissue. Furthermore, a mitral valve clip is a relatively large amount of hardware to implant in the heart which may increase the risk of embolism and tissue rejection. With the method 900, the only materials implanted in the body are the sutures which present a significantly lower risk to the patient.

Additional Example Locking Suture Delivery Devices and Methods

Figure 9:
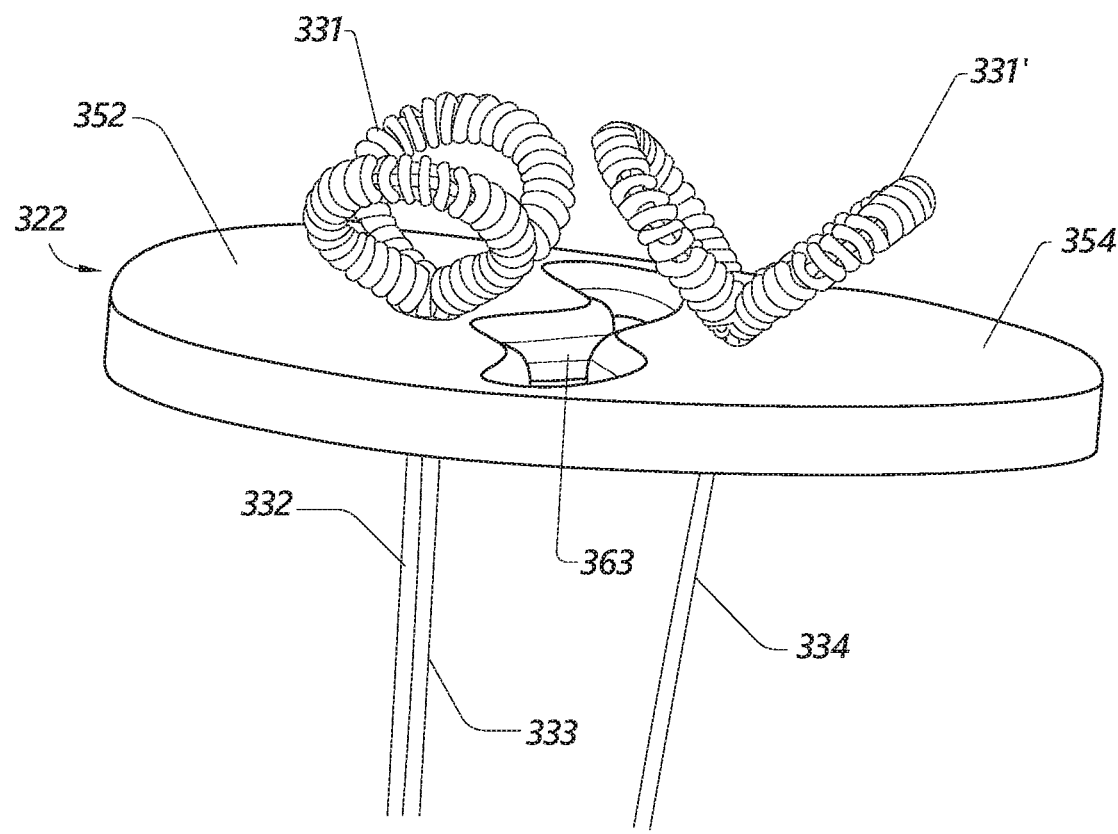
FIG. 9 is a schematic illustration of a mitral valve with leaflets that are separated by a gap.

FIGS. 9 and 10A-10D illustrate schematically a method and delivery device for delivering and deploying a locking suture 337 to secure artificial chordae tendineae that have been implanted as described in the '761 PCT Application and/or the '170 PCT Application. FIG. 9 is a schematic illustration of a mitral valve 322 with leaflets 352, 354 that are separated by a gap 363. As shown in FIG. 9, two bulky knot implants 331, 331' are disposed on an atrial, distal, or top side of the leaflets 352, 354, respectively. The implants 331, 331' can be formed with a suture material that forms one or more loops on the atrial side of the leaflets 352, 354 and extends through the leaflets 352, 354, with two loose suture end portions that extend on the ventricular, proximal, or bottom side of the leaflets 352, 354. The implant 331 has suture end portions 332 and 333, and the implant 331' has suture end portions 334 and 335 (not shown in FIG. 9).

After the implants 331, 331' are in a desired or targeted position (which can be confirmed with imaging, for example), a LS delivery device 346 as shown in FIGS. 10A-10D can be used during a procedure to secure the implants 331, 331' in the desired position and to secure the valve leaflets 352, 354 in an edge-to-edge relationship. Further, in addition to or instead of creating the edge-to-edge relationship, to promote a larger surface of coaptation, using the LS delivery device 346, the implants 331, 331' can be secured together to pull or otherwise move the posterior annulus towards the anterior leaflet and/or the anterior annulus towards the posterior leaflet, to reduce the distance between the anterior annulus and the posterior annulus, e.g., the septal-lateral distance by about 10%-40%. Approximating the anterior annulus and the posterior annulus in this manner can decrease the valve orifice, and thereby decrease, limit, or otherwise prevent undesirable regurgitation. This technique can be valuable in both degenerative MR with a prolapsed leaflet where the annulus is dilated and in functional MR where the leaflet function is normal but the annulus has dilated and there is a gap between the leaflets that can be closed by approximating the tissue.

For ease of illustration, the following example locking suture deployment sequence in connection with FIGS. 10A-10D is shown and described using only two suture portions 332, 334. Note, however, the locking suture can be deployed about and secured to any suitable number of suture portions. For example, as shown in or described with respect to FIG. 9, four suture portions (e.g., sutures portions 332, 333, 334, 335) extend from the implants 331, 331'. Further, in some embodiments, in which more than two implants and/or more than two tissues are to be approximated, the locking suture can be deployed about and/or secured to more than four suture portions (e.g., six or more suture portions).

Figure 10A:
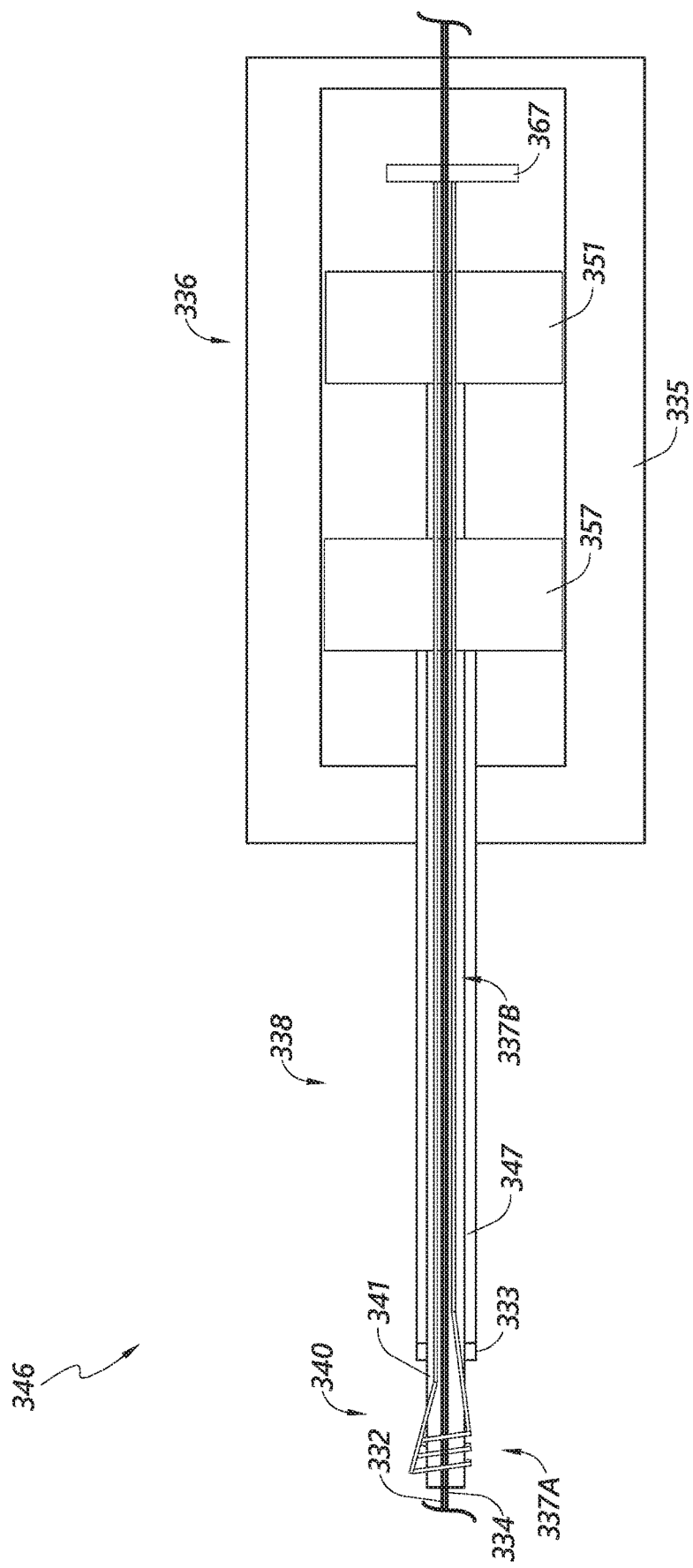
FIGS. 10A, 10B, 10C, and 10D illustrate a method using a LS delivery device to deliver and deploy a locking suture, according to an embodiment.

As shown in schematic cross-section in FIG. 10A, the LS delivery device 346 includes a distal end portion 340, a medial portion 338, and a proximal end portion 336. Disposed on the distal end portion 340 is a knot end effector 333 that extends from a distal end portion 340 of an elongated knot pusher tube 347 (also referred to herein as "knot pusher"). As described in further detail below, the knot end effector 333 provides a surface against which and/or a volume within which a knot portion 337A of the locking suture 337 can be deployed. A proximal end portion of the knot pusher 347 is coupled to a handle 335 at the proximal end portion 336 of the LS delivery device 346. Coupled to and included at least partially within the handle 335 is a proximal end portion of the knot pusher 347 coupled to a pusher hub 357, an inner elongate member 341 (also referred to herein as "pre-formed knot holder" or "knot holder") coupled to an inner elongate member hub 351 (also referred to herein as "knot holder hub"), and a locking suture catch 367 (also referred to herein as "LS catch"). As shown, the knot holder hub 351 is disposed proximal to the knot pusher hub 357 and distal to the LS catch 367. The knot holder 341 is movably disposed within a lumen of the knot pusher 347. As shown in FIG. 10A, the locking suture 337 is coupled to the LS catch 367 and extends through a lumen of the knot holder 341 and a lumen of the knot pusher 347 and is formed into a coiled configuration (e.g., the knot portion 337A) at the distal end portion 340 of the LS delivery device 346. More specifically, the knot portion 337A of the locking suture 337 is disposed about the distal end portion of the knot holder 341 and distal to the knot pusher 347, and the tether portion 337B of the locking suture 337 extends from the knot portion 337 through the lumen of the knot pusher 347 and coupled to the LS catch 367 within the handle 335.

The LS catch 367 can be configured to releasably hold or secure the tether portion 337B during delivery and deployment of the knot portion 337A as described in more detail below. In some embodiments, the LS catch 367 can hold the tether portion 337B with a friction fit or with a clamping force and can have a lock that can be released after the knot portion 337A has been deployed. As discussed above for locking suture 337, for example, the knot portion 337A can be in the form of one or more multi-turn coils, winds, and/or cow hitches of the locking suture 337 that can be changed from an elongated configuration during delivery (see, e.g., FIGS. 10A and 10B), to a deployed configuration (e.g., tightened, bulky, bunched, or looped knot; see, e.g., FIG. 10D) by tightening, constricting, and/or shrinking the multi-turn coils or winds, and/or approximating opposite ends of the winds or coils towards each other. Said another way, during deployment, the coils, wraps, loops, turns, or portions of the knot portion 337A disposed about the suture portions 332, 334 are tightened, shortened, and/or constricted, and/or looped resulting in a restrained or confined tortuous path for the suture portions 332, 334 sufficient to inhibit relative motion between the knot portion 337A and the regions of the suture portions 332, 334 intertwined therewith.

To deliver and deploy the locking suture 346 to suitably approximate the suture portions 332, 334 and implants 331, 331', and the heart tissues T1, T2 (the implants and heart tissues are not shown in FIGS. 10A-10D) attached thereto, for example, the free ends of the suture portions 332, 334 extending from the implants 331, 331' inside the heart and through an incision in the apex region of the heart, for example, can be threaded, woven, and/or routed through the turns or winds of the knot portion 337A, e.g., in FIG. 8B. As shown and described in further embodiments below, the LS delivery device 346 in some instances may be pre-loaded with one or more wire threaders (not shown in this embodiment) to assist an operator (e.g., a surgeon) with threading the suture portions 332, 334 through various regions of the knot portion 337A in a desired and/or predefined configuration to maximize post-deployment securement between the suture portions 332, 334 and the locking suture 337.

Figure 10B:
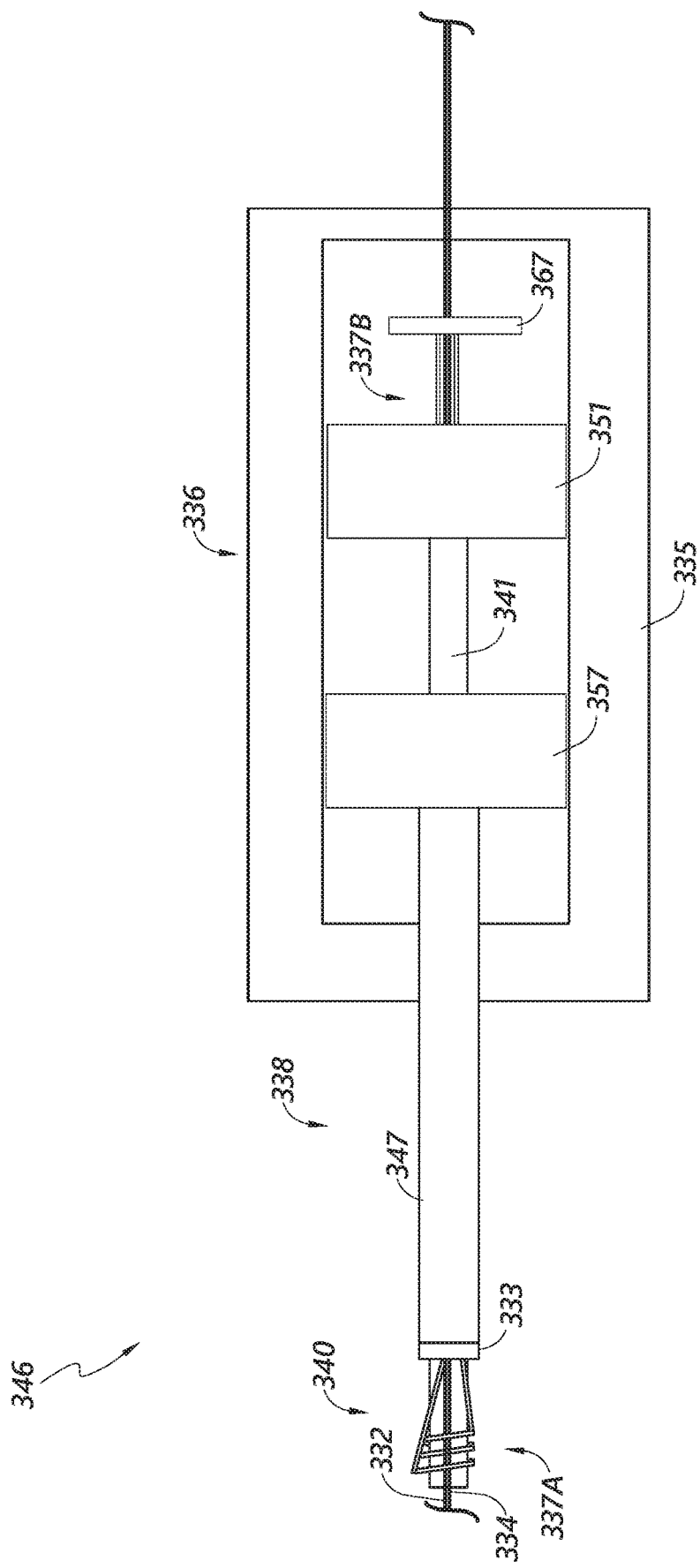

With the suture portions 332, 334 suitably threaded through and/or coupled to the knot portion 337 (in its delivery configuration), as shown in FIG. 10B, the free ends of the suture portions 332, 334 can be releasably held by the operator and/or releasably fixed or secured to a suitable component (e.g., to a portion of the knot pusher 347). With the free ends of the suture portions 332, 334 releasably fixed in this manner, the LS delivery device 346 can be advanced distally relative to the fixed free ends of the suture portions 332, 334 and towards the heart tissues and to a suitable deployment location, similar to as shown and described with respect to FIG. 2B. For example, the distal end portion 340, and in some instances the medial portion 338, of the LS delivery device 346 can be moved distally through the incision (through which the suture portions 332, 334 extend from the heart) and into the left ventricle of the heart. In this manner, the knot portion 337A can be advanced along or about the suture portions 332, 334 and towards the tissues until the knot portion 337A reaches a desirable location and/or the tissues are desirably approximated.

Figure 10C:
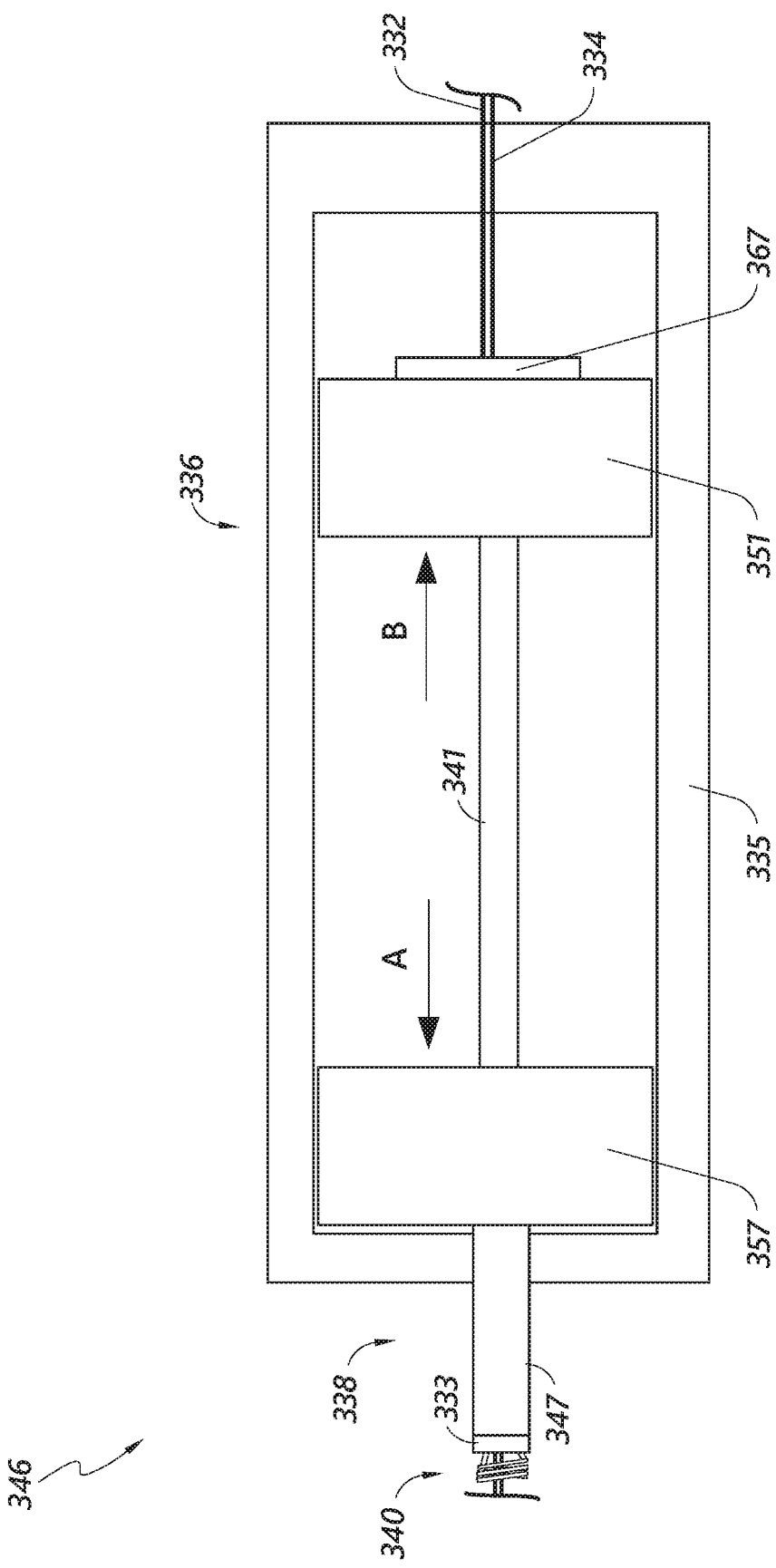
Figure 10D:
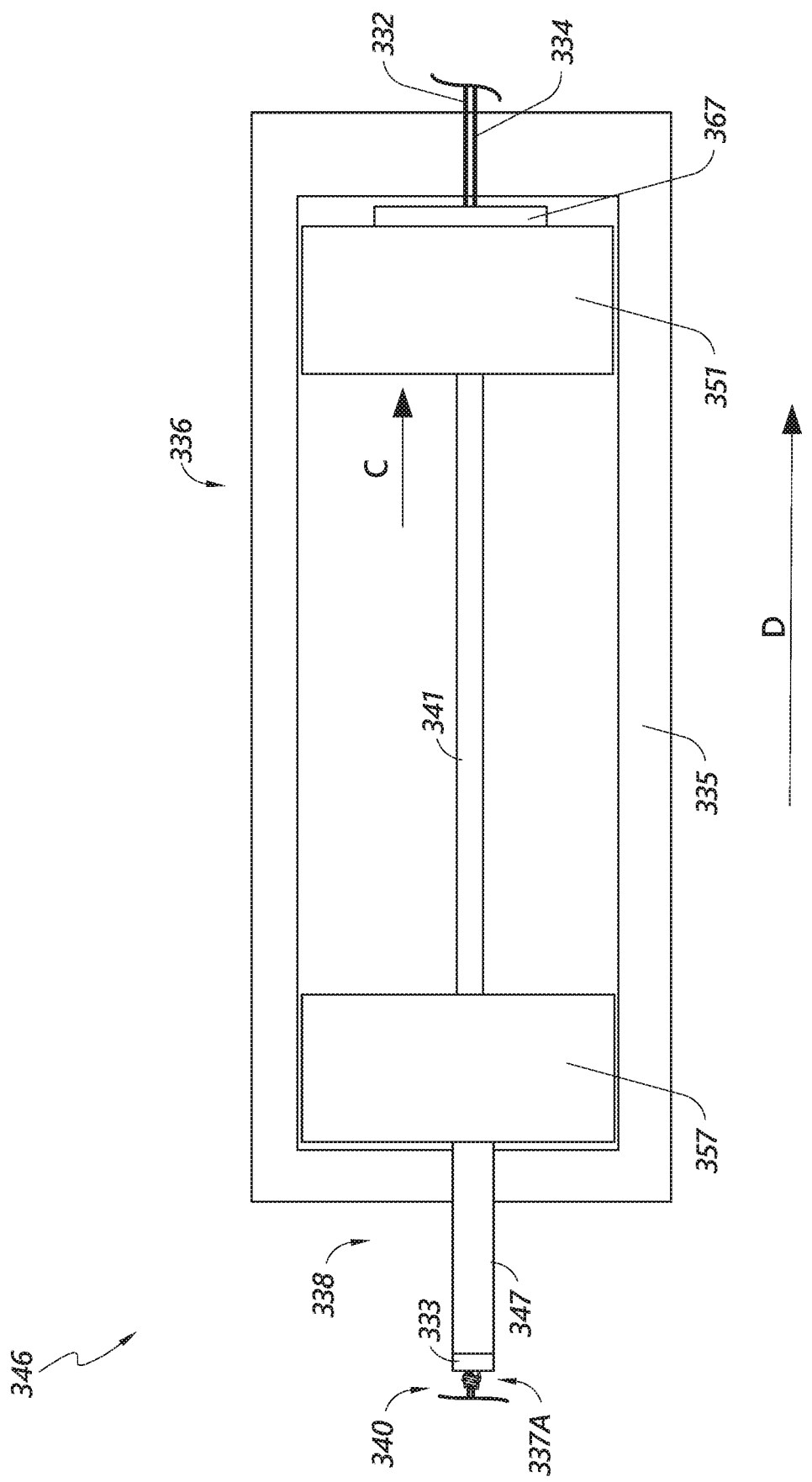

With the knot portion 337A delivered to a suitable location and/or with the tissues desirably approximated, the knot holder hub 351 can be withdrawn within and relative to the handle 335 (in the direction of arrow B) and/or the knot pusher hub 357 can be pushed or moved distally within and relative to the handle 335 (in the direction of arrow A) to displace the knot portion 337A off and/or from the knot holder 341, leaving the knot portion 337A separate from the knot holder 341 and on the distal side of the knot pusher 351, as shown in FIG. 10C. In some instances, there can be some slack in the length of tether portion 337B to allow the knot portion 337A to slide off the knot holder 341 before deploying. With the knot portion 337A displaced from the knot holder 341, the knot portion 337 is ready to be deployed about the suture portions 332, 334 threaded therethrough. To deploy, the knot holder hub 351 and the LS catch 367, and thereby the tether portion 337B of the locking suture 337 (which is releasably fixed to the LS catch 367), can be withdrawn proximally within and relative to the handle 335 (in the direction of arrow C), causing the knot portion 337A to transition from its delivery configuration to its deployed configuration, as shown in FIG. 10D. Although in this embodiment at this stage the LS catch 367 and the knot holder hub 351 are shown and described as being withdrawn within the handle 335 together, in other embodiments, the LS catch 367 can be withdrawn proximally relative to the knot holder hub 351 to deploy the knot portion 337A of the locking suture 337. More specifically, with the tether portion 337B releasably secured to the LS catch 367, proximal movement of the LS catch 367 relative to the knot pusher pulls the tether portion 337B proximally, causing the knot portion 337A to deploy on the distal end of the knot pusher 347.

After the knot portion 337A has been deployed (FIG. 10D), the suture portions 332, 334 can be released by the operator, and the tether portion 337B can be released from the LS catch 367, and the LS delivery device 346 can be withdrawn proximally in the direction of arrow D, leaving the deployed knot portion 337A within the heart, and free ends of the suture portions 332, 334 and the free ends of the tether portion 337B extending out of the heart. In other words, with the tether portion 337B released from the LS catch 367 and the two lengths of the suture portions 332, 334 extending proximally from the deployed knot portion 337A similarly released, the LS delivery device 346 can be slid over the two lengths of the suture portions 332, 334 for removal.

The locking suture, and particularly the knot portions described herein (e.g., knot portion 137A, 237A, 337A) can be formed in any suitable formation such that the locking suture can be suitably delivered and deployed in various expected environments, and that when deployed with portions of one or more sutures (e.g., suture portions 332, 333, 334, 335) threaded therethrough, the deployed knot portion will secure and/or inhibit relative movement between the deployed knot portion and the sutures disposed or captured therein. In this manner, similar to as described with respect to FIG. 2D and locking suture 237, securing or inhibiting relative movement can promote a desirable approximation of the tissues attached to the deployed knot portion via the suture portions.

There are several design considerations for the knot portion. When disposed about the knot holder, unraveling of the knot portion can be inhibited or prevented during delivery to a target region. The knot portion can be assembled about the knot holder without fastening or retaining means (e.g., retaining clips or bands) to hold the knot portion in place without unraveling, thus promoting more efficient assembly. When disposed about the knot holder, suture portions extending from the tissues can glide or be threaded through the winds or coils of the knot portion with minimal resistance to promote efficient assembly. When deployed about the suture portions, the knot portion inhibits relative movement therebetween, and the knot portion retains this deployed state in part in response to tensile loading applied to its tether portion (e.g., the tether portion is pulled and anchored to an outer surface of the heart at a desirable tension). Slack or loose coils or winds in the knot portion from assembly to delivery and deployment can be inhibited or prevented. The knot portion is suitably slidable along or about the suture portions during delivery, including outside the target region or patient (e.g., in a relatively dry environment) and inside the target region or patient (e.g., in a relatively wet environment, such as, for example, within a beating heart). The knot portion is deliverable through an introducer or delivery catheter without being compromised (e.g., unraveling; damaged, or any other undesirable consequences). The knot portion is capable of being guided along or about the sutures without undesirable tension on the tissues attached to the sutures, by for example, pulling or tensioning the sutures while the knot portion is guided along or about the suture. The knot portion is capable of maintaining its deployed state under expected pressures or tension, such as, for example, about 2.2 pounds per square inch (psi).

FIGS. 11A-11G illustrate an example method of forming a knot portion 437A of a locking suture 437 in an elongated coiled configuration (e.g., delivery configuration) about an exterior of a knot holder 441. The locking suture 437 and the knot holder 441 can be constructed similarly to or the same as, and function similarly to or the same as, any of the locking sutures and knot holders described herein. Thus, some details regarding the locking suture 437 and the knot holder 441 are not described below. It should be understood that for features and functions not specifically discussed, those features and functions can be the same as or similar to any of the locking sutures and knot holders described herein.

Figure 11A:
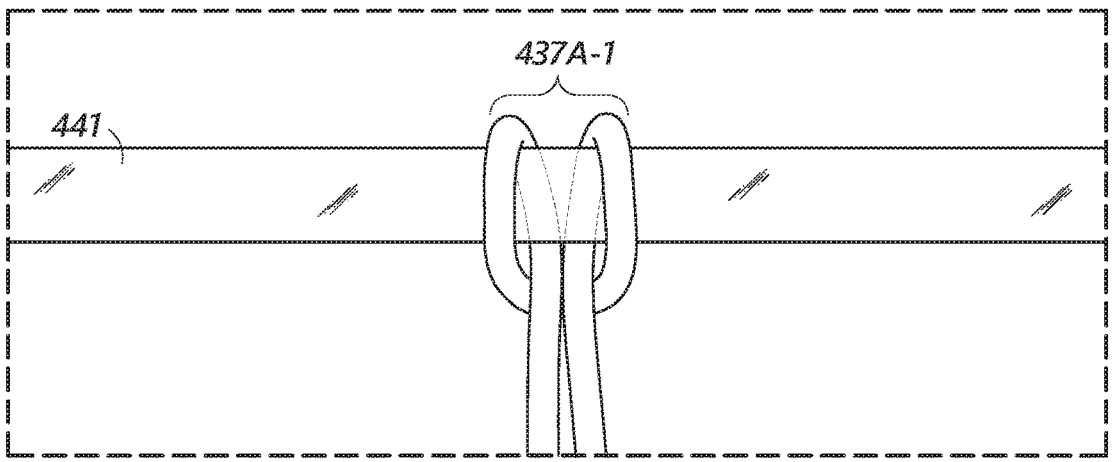
FIGS. 11A, 11B, 11C, 11D, 11E, 11F, and 11G illustrate a method of forming a knot portion of a locking suture about a knot holder, according to an embodiment.
Figure 11B:
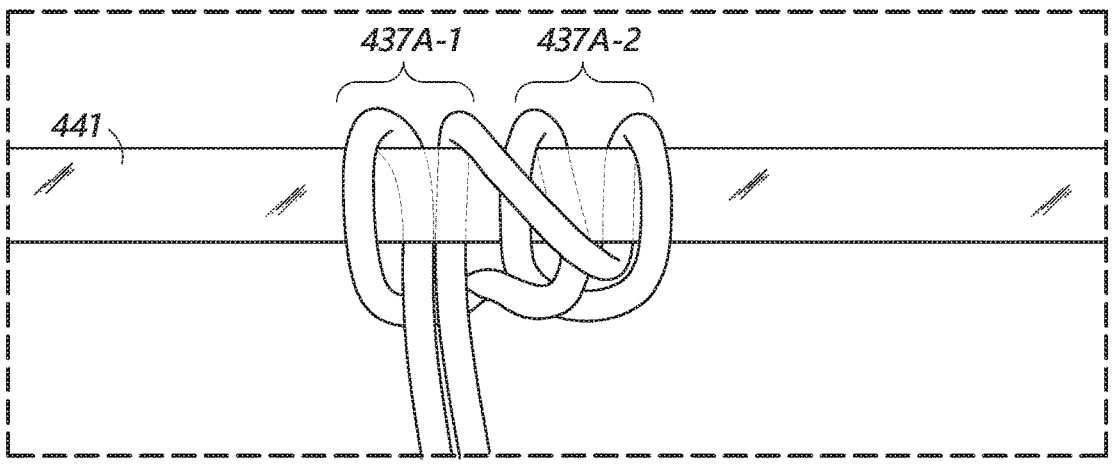
Figure 11C:
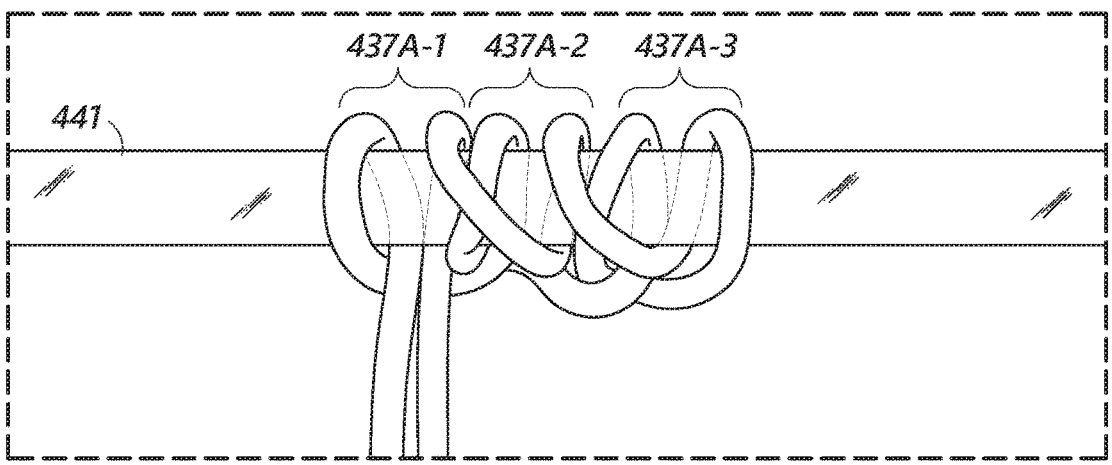
Figure 11D:
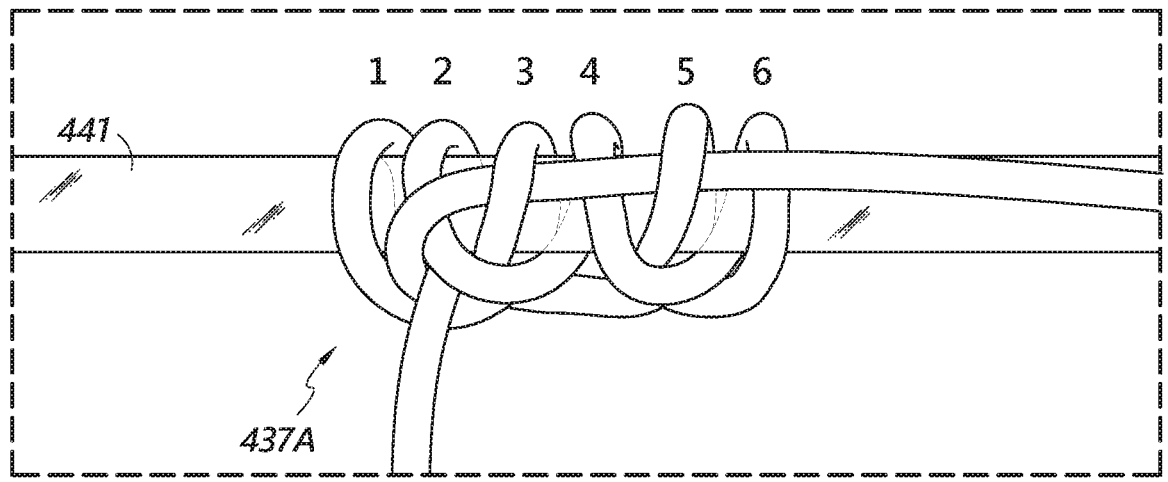

To begin formation of the knot portion 437A, in this embodiment, as shown in FIGS. 11A-11C, three cow hitches 437A-1, 437A-2, 437A-3 are formed about the knot holder 441. Although in this embodiment three cow hitches are used, in alternative embodiments, any suitable number of cow hitches may be used (e.g., 1, 2, 4, 5, or more cow hitches). The number of cow hitches may be selected based on the particular medical operation and/or the forces that the deployed locking suture 437 is expected to experience. For approximating two tissues within a ventricle of a human heart, for example, it has been found that, in some instances, three cow hitches is sufficient. For ease of illustration, the locking suture 437 is illustrated with each loop formed about the knot holder 441 being labeled from loop 1 through loop 6 (from left to right, or distal to proximal). Each cow hitch defines two loops. Specifically, first cow hitch 437A-1 defines loop 1 and loop 2, second cow hitch 437A-2 defines loop 3 and loop 4, and third cow hitch 437A-3 defines loop 5 and loop 6, as illustrated and labeled in FIGS. 11D-11G. After the three cow hitches are formed, the first free end extending from the first cow hitch 437A-1 (see, e.g., FIG. 11C in which the first free end is hatched in green, which is an extension of the white portion extending from loop 1 of the first cow hitch 437A-1) is routed proximally and threaded through loop 3 and loop 5, as shown in FIG. 11D. More specifically, as shown in FIG. 11D, the first free end is routed around (or over, or radially outwardly from) loop 2, then through (or within, or radially inwardly from) loop 3, then around loop 4, then through loop 5, and then around loop 6. After exiting loop 6, the first free end is wrapped or turned around loop 6, as shown in FIG. 11F. Similarly stated, after exiting loop 6, the first free end is routed distally through loop 6 for a second time and then proximally around loop 6 for a second time.

Figure 11E:
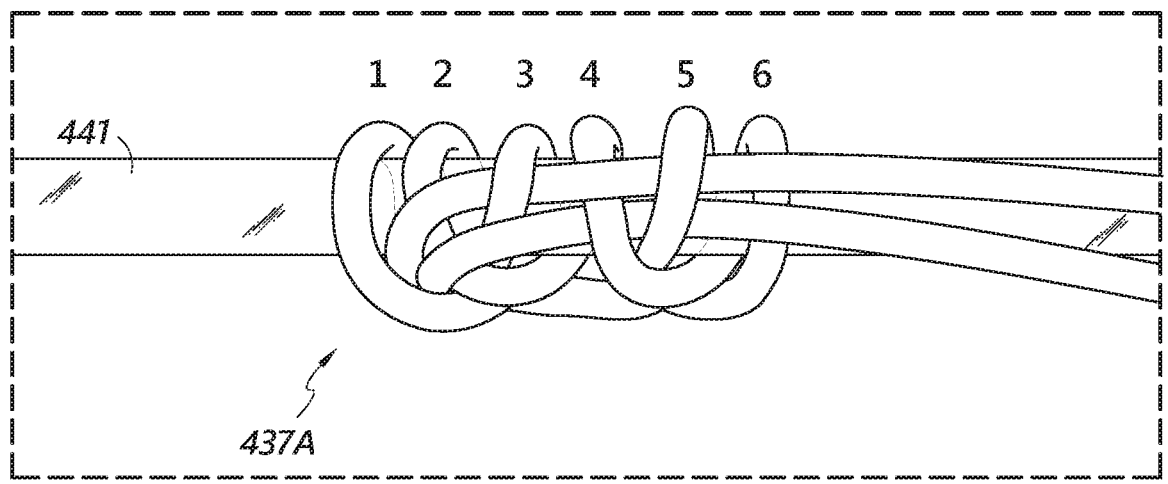
Figure 11F:
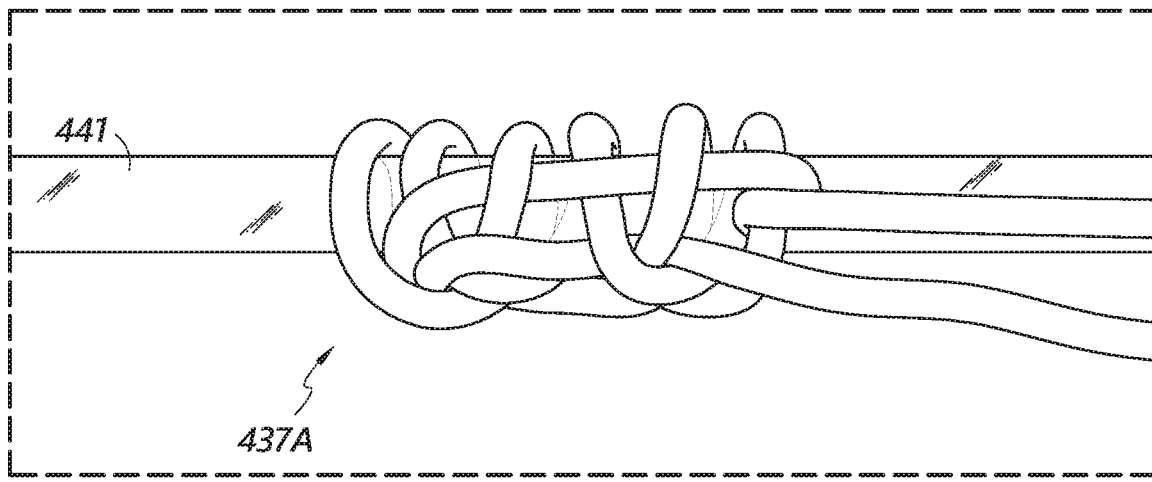
Figure 11G:
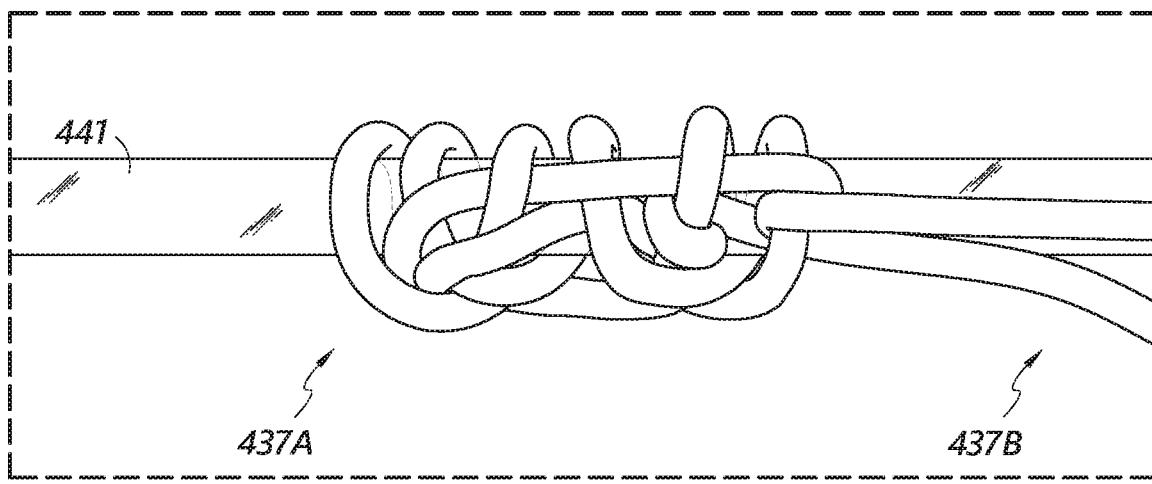

Additionally, after the three cow hitches are formed, the second free end (e.g., the other free end of the locking suture 437) extending from the first cow hitch 437A-1 is routed proximally and threaded through loop 4 and loop 5, as shown in FIG. 11E. More specifically, as shown in FIG. 11E, the second free end is routed around loop 3, then through loop 4 and loop 5, and then around loop 6. After extending through loop 4 and 5 and around loop 6, the second free end is wrapped or turned around loop 5 (e.g., through and around loop 5), and then through loop 6, as shown in FIG. 11G.

Figure 12A:
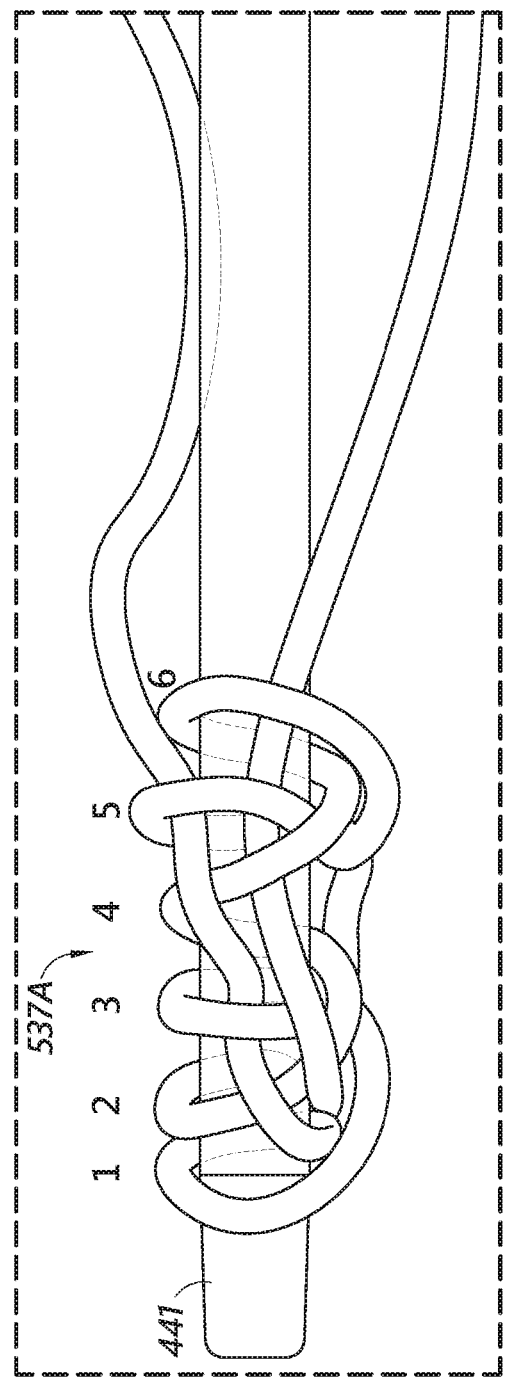
Figure 12B:
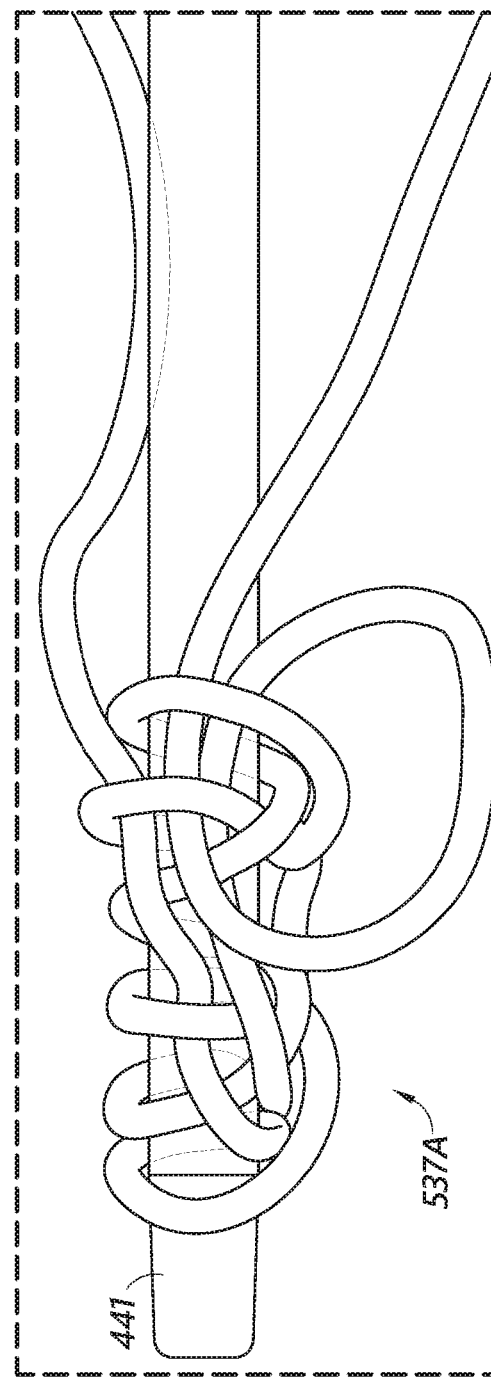
Figure 12E:
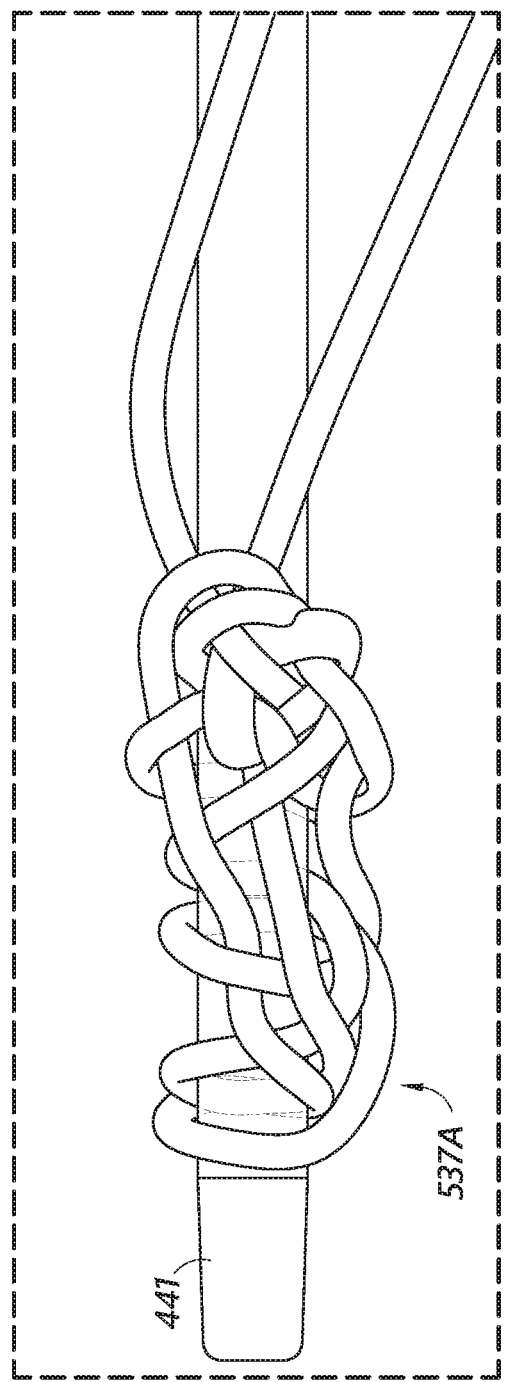
Figure 14:
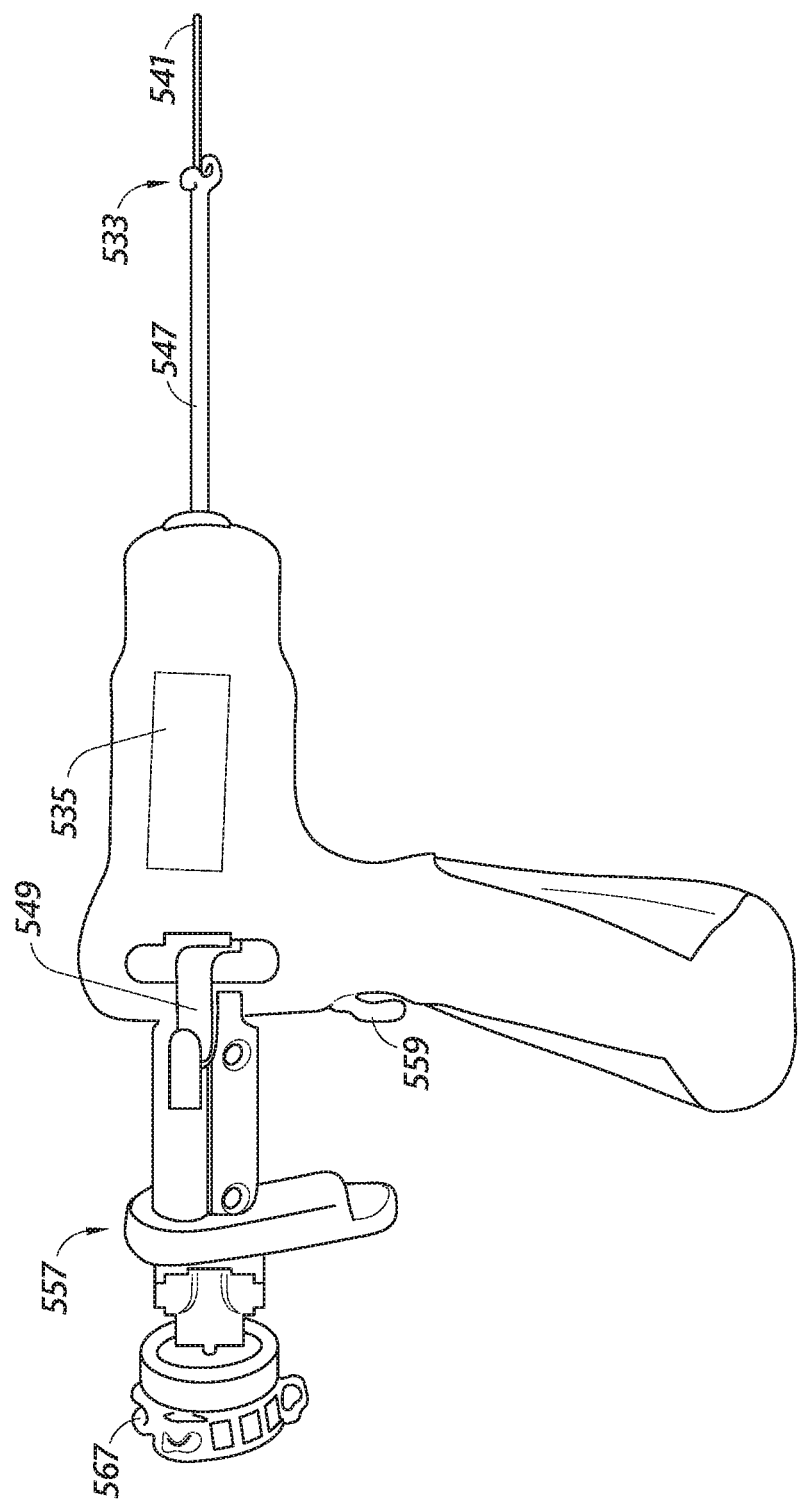
FIG. 14 illustrates in left side view the LS delivery device of FIG. 13.

FIGS. 12A-12E illustrate another example approach for forming the locking suture knot 437. FIG. 12A illustrates an alternate procedural step after performing the step illustrated in FIG. 11D. Thus, in FIG. 12A the second free end is routed around loop 3, then through loops 4, 5, and 6. After extending through loops 4, 5, and 6, the second free end is brought back through loops 5 and 6, as illustrated in FIG. 12B. The first free end is then looped under loop 6 so that it goes through the loop formed by the second free end in the previous step, as illustrated in FIG. 12C. The first free end is then looped back around to go over the loop formed by the second free end and through loop 6, as illustrated in FIG. 12D. The resulting locking suture is tensioned to remove the slack while still allowing the locking suture to slide to allow it to be positioned along suture tails, as illustrated in FIG. 12E.

FIGS. 13, 14, 15A-15I, 16A-16AL, and 17A-17W illustrate another embodiment of a LS delivery device 546 that can be used to deliver and deploy a locking suture 537. The LS delivery device 546 and the locking suture 537 can be constructed similar to or the same as and function similar to or the same as any of the LS delivery devices and locking sutures described herein. Thus, some details regarding the LS delivery device 546 and the locking suture 537 are not described below. It should be understood that for features and functions not specifically discussed, those features and functions can be the same as or similar to any of the LS delivery devices and locking sutures described herein.

As shown in FIG. 13 (right side view) and 14 (left side view), the LS delivery device 546 includes a distal end portion 540, a medial portion 538, and a proximal end portion 536. Disposed on the distal end portion 540 is a knot end effector 533 that extends from a distal end portion 540 of an elongated knot pusher tube 547 (also referred to herein as "knot pusher"). As described in further detail below, the knot end effector 533 provides a surface against which, and a volume within which, a knot portion 537A of the locking suture 537 can be deployed. A proximal end portion of the knot pusher 547 is coupled to a handle 535 at the proximal end portion 536 of the LS delivery device 546. Extending from within the handle 535, through a lumen of the knot pusher 547, and out a distal end of the knot end effector 533 is an inner elongate member 541 (also referred to herein as "pre-formed knot holder" or "knot holder"). The knot holder 541 is slidably disposed within the knot pusher 547 and the handle 535, and is retractable (relative to the knot pusher 547 and handle 535) from the position shown in FIGS. 13 and 14 in which the distal end of the knot holder 541 is distal to the knot end effector 533 to a position (not shown) in which the distal end of the knot holder 541 is proximal to the knot end effector 533. In this manner, as described in previous embodiments, in use, the knot portion 537A can be formed about the distal end of the knot holder 541 in a position distal to the knot end effector 533, and then delivered to a suitable location within a target region (e.g., within the left ventricle of a heart). The LS delivery device 546 can then be actuated to deploy the knot portion 537A, which can include displacing the knot portion 537A from the knot holder 541 by retracting or withdrawing proximally the knot holder 541 relative to the knot pusher 547.

Although in this embodiment the knot holder 541 is described as being slidable within and relative to the knot pusher 547 and the handle 533, in other embodiments, an LS delivery device can be constructed in any suitable manner to displace a knot portion from a knot holder. In such alternative embodiments, for example, an LS delivery device may include a knot holder fixed relative to and extending from its handle, and a knot pusher slidable or extendable from the handle sufficient to push or displace the knot portion from and distal to the fixed knot holder.

The LS delivery device 546 further includes an actuator 557 (also referred to herein as "plunger") configured to be actuated to push or advance the knot pusher 547 distally relative to the handle 533. To prevent premature advancement of the plunger 557, the LS delivery device 546 further includes a plunger lock 559 configured to be manipulated between a locked position, in which movement of the plunger 557 relative to the handle 533 is inhibited or prevented, and an unlocked position, in which the plunger 557 can be moved (e.g., actuated) relative to the handle 533. Similarly the stated, the plunger 557 cannot be actuated when the plunger lock 559 is in its locked position, and can be actuated when the plunger lock 559 is in its unlocked position.

Further, to prevent undesirable retraction or proximal movement of the plunger 557 (which could undesirably expose the distal end of the knot holder 541 from the distal end of the knot pusher 547), for example, after displacement of the knot portion 537A from the knot holder and distal advancement or actuation of the plunger 557, the LS delivery device 546 further includes a plunger retainer 549 configured to be engaged or transitioned to its retaining position to prevent undesirable proximal movement of the plunger 557 relative to the handle 533.

Figure 15A:
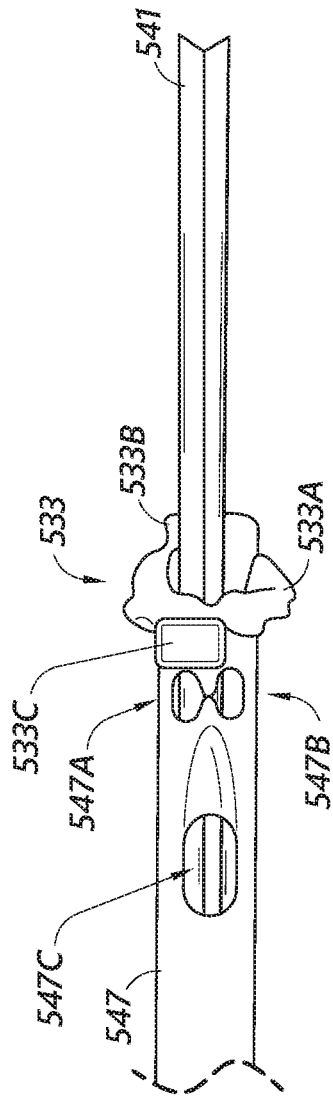
FIGS. 15A and 15B illustrate detailed top views of the knot pusher of the LS delivery device of FIG. 13 with a knot holder in an extended position and a retracted position, respectively.
Figure 15B:
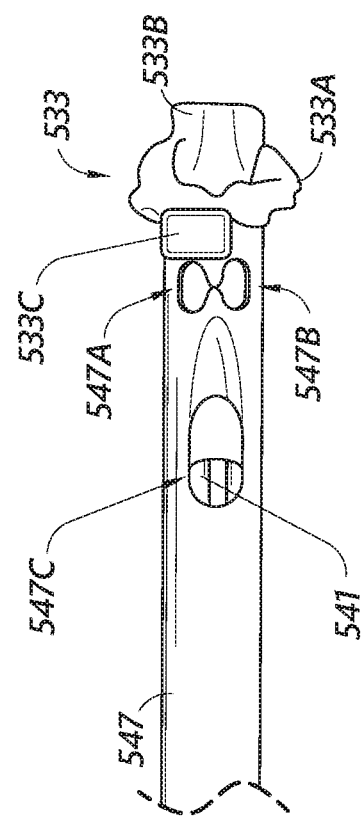
Figure 15C:
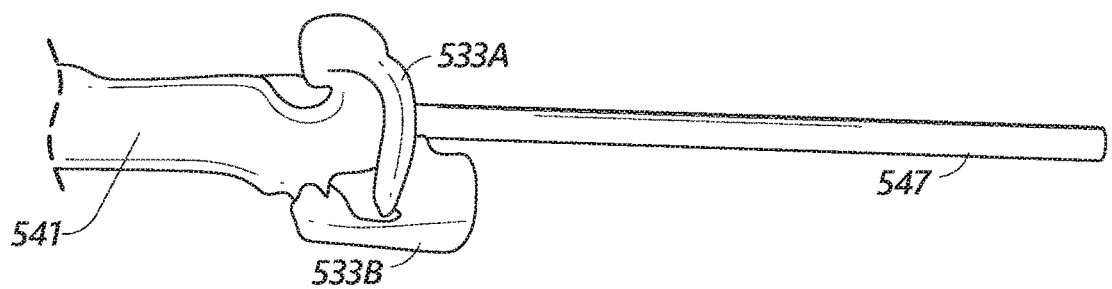
FIG. 15C illustrates a detailed side view of the knot pusher of the LS delivery device of FIG. 13 with a knot holder in an extended position.
Figure 15D:
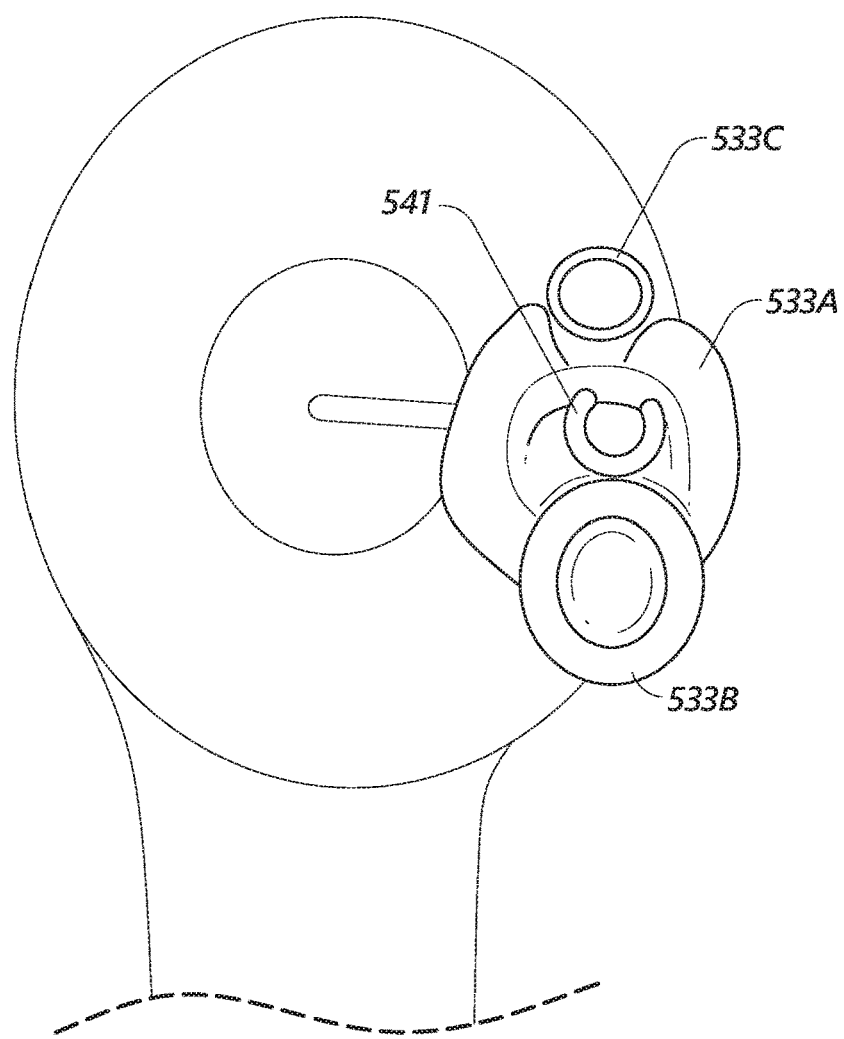
FIG. 15D illustrates a detailed front view of the knot pusher of the LS delivery device of FIG. 13 with a knot holder in disposed within the lumen of the knot pusher.
Figure 15E:
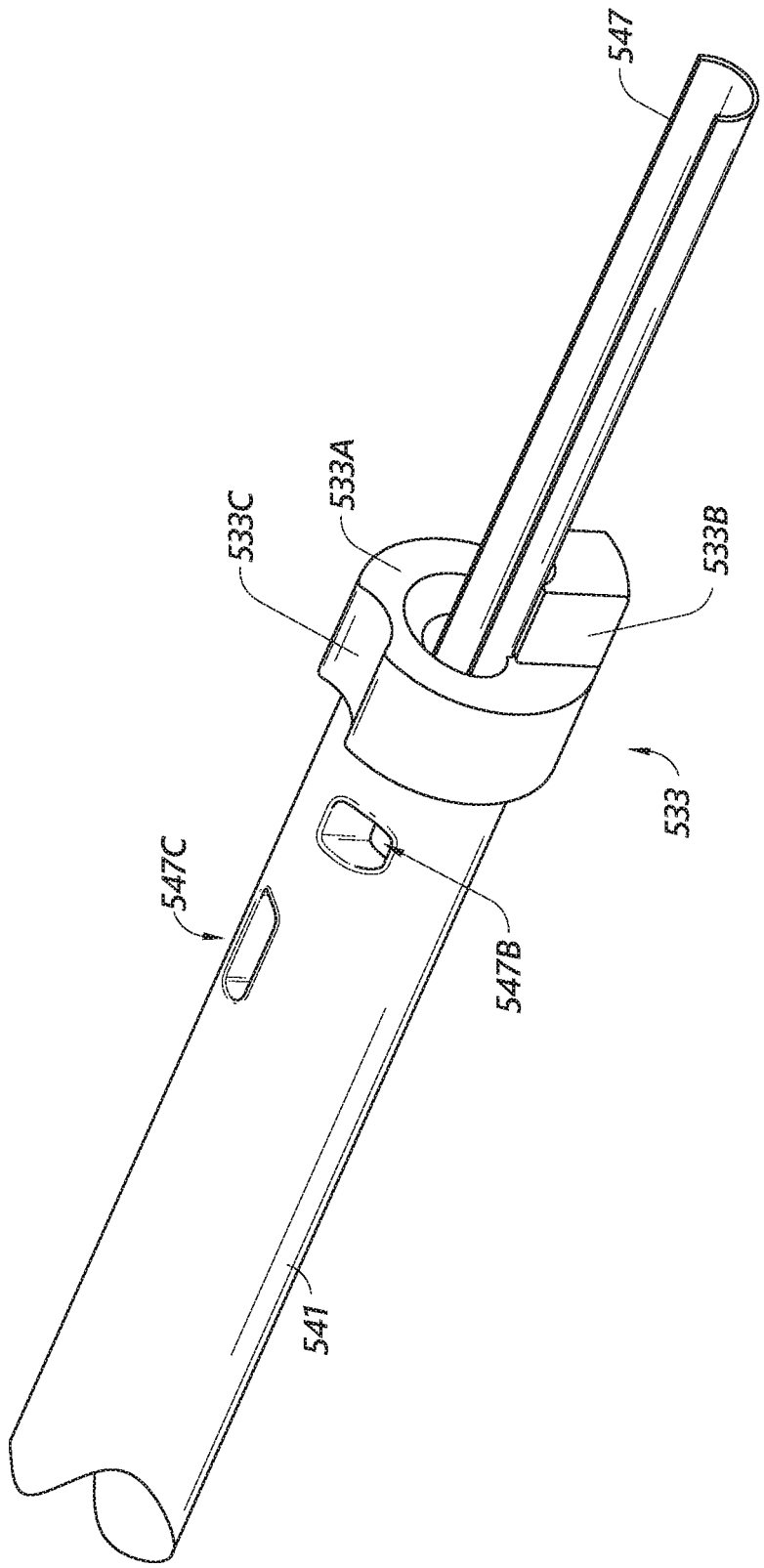
FIG. 15E illustrates a detailed perspective view of the knot pusher, the knot end effector, and the knot holder extending distally therefrom.
Figure 15G:
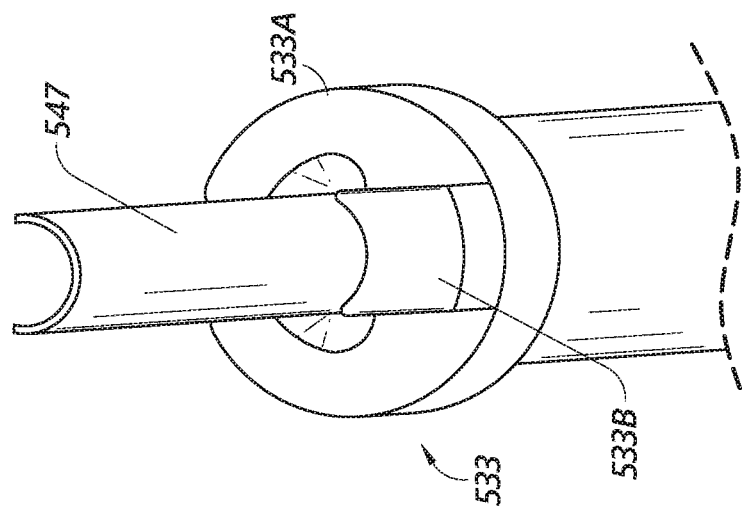
FIG. 15G illustrates a detailed bottom perspective view version of FIG. 15E.
Figure 15F:
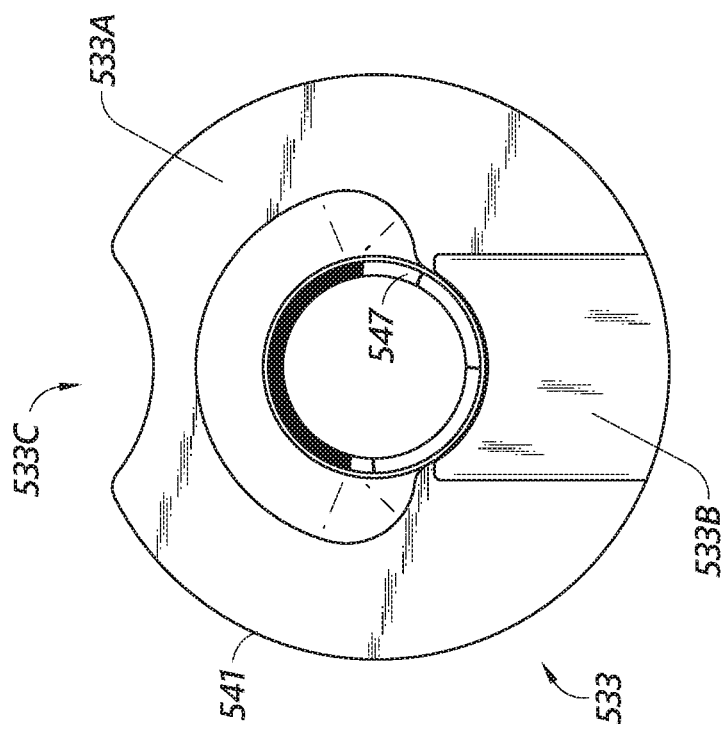
FIG. 15F illustrates a detailed front view version of FIG. 15E.

FIGS. 15A and 15C illustrate detailed top and side views, respectively, of the knot pusher 547, the knot end effector 533, and the knot holder 541 extending distally therefrom. FIG. 15B illustrates a detailed top view of the knot pusher 547 and the knot end effector 533, but with the distal end of the knot holder 541 disposed within the lumen of the knot pusher 547 and proximal to the knot end effector 533. FIG. 15D illustrates a detailed front view of the knot pusher 547, the knot end effector 533, and the knot holder 541 disposed within the lumen of the knot pusher 547. FIG. 15E illustrates a detailed perspective view of the knot pusher 547, the knot end effector 533, and the knot holder 541 extending distally therefrom. FIG. 15F illustrates a detailed front view version of FIG. 15E; FIG. 15G illustrates a detailed bottom perspective view version of FIG. 15E; FIG. 15H illustrates a detailed top view version of FIG. 15E; and FIG. 15I illustrates a detailed front perspective view version of FIG. 15E.

The knot end effector 533 includes a knot receiving portion 533A (also referred to herein as "end effector cup") configured to provide a volume or partial enclosure within which the knot portion 537A can be deployed, and/or a surface or backstop against which the knot portion 537A can be deployed. Similarly stated, the end effector cup 533A can serve as a place holder for the knot portion 537A to form during deployment. In this manner, the end effector cup 533A can contain the knot portion 537A and inhibit undesirable movement, for example, as the free ends or tether portion 537A is tensioned, pulled, and/or withdrawn. In use, for example, when the tether portion 537B is withdrawn to cause the knot portion 537A to deploy, the knot portion 537A in response to withdrawal of the tether portion 537B will be pulled or urged proximally into and against the knot receiving portion 533A. With the knot portion 537A within the knot receiving portion 533A and abutting a surface of the knot receiving portion 533A, further withdrawal of the tether portion 537B will result in the coils and turns of the knot portion 537A tightening and constricting and the ends of the coils approximating, as described in previous embodiments. Causing the knot portion 537A to deploy in such a restricted space (e.g., the partial enclosure of the knot receiving portion 533A) promotes formation of a sufficiently tight and secured deployed knot.

Figure 16A:
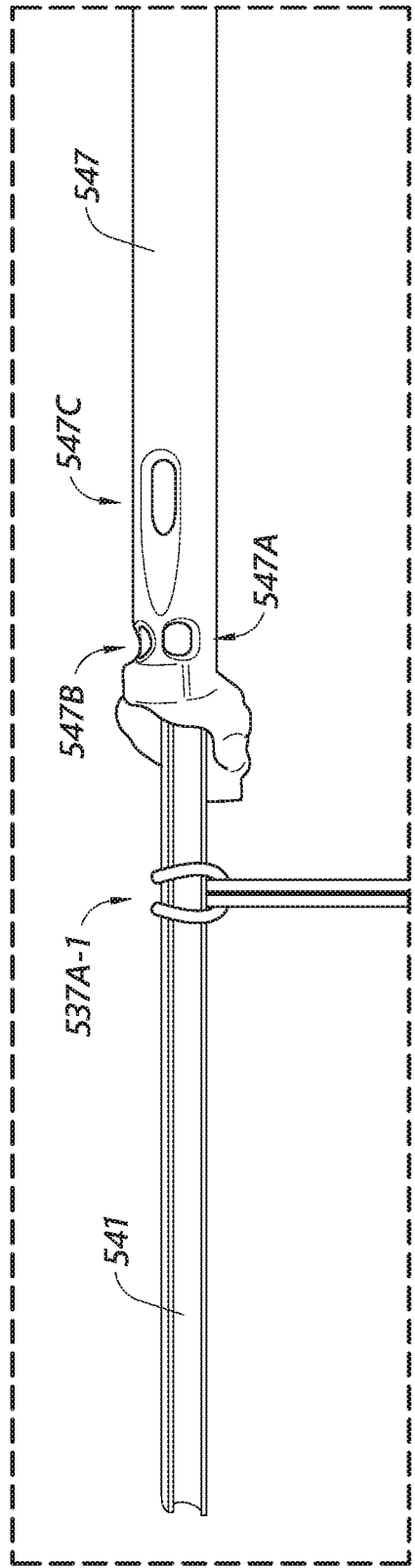

The knot end effector 533 further includes a protrusion 533B extending distally from the knot receiving portion 533A and configured to prevent the knot portion 537A from bunching and/or being drawn too far into the lumen of the knot pusher 547, for example, when the suture portions extending from the tissues and implants (as described with respect to previous embodiments) are threaded through the knot portion 537A and then into the knot pusher 547, and to provide ample space through which the tether portion 537B can extend from the knot portion 537A into the lumen of the knot pusher 547 (see, e.g., FIG. 16AH). In some instances, the protrusion 533B is configured to partially displace the knot portion 537A from the lumen of the knot pusher 547 to inhibit undesirable resistance for the suture portions when threaded and/or pulled through portions of the knot portion 537A when in its delivery configuration.

The knot end effector 533 further includes an alignment loop, slot or guide 533C configured to slidably receive and at least partially align, guide, or retain the suture portions extending from the knot portion 533A (see, e.g., FIG. 16AJ or FIGS. 15E, 15F, and 15I), as described in further detail below. Further, the knot pusher 547 defines three side apertures or orifices (e.g., a first aperture 547A, a second aperture 547B circumferentially adjacent to the first aperture, and a third aperture 547C proximal to the first and second apertures 547A, 547B) proximal to the knot end effector 533, as shown in FIGS. 15A and 15B to provide knot pushing functionality, as described in further detail below.

Figure 16B:
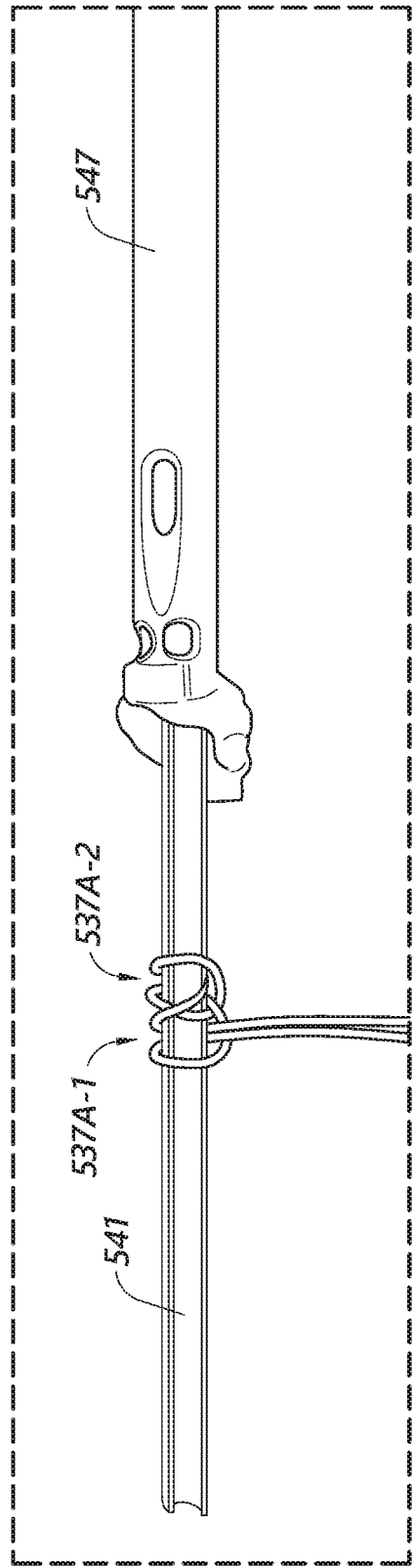
Figure 16C:
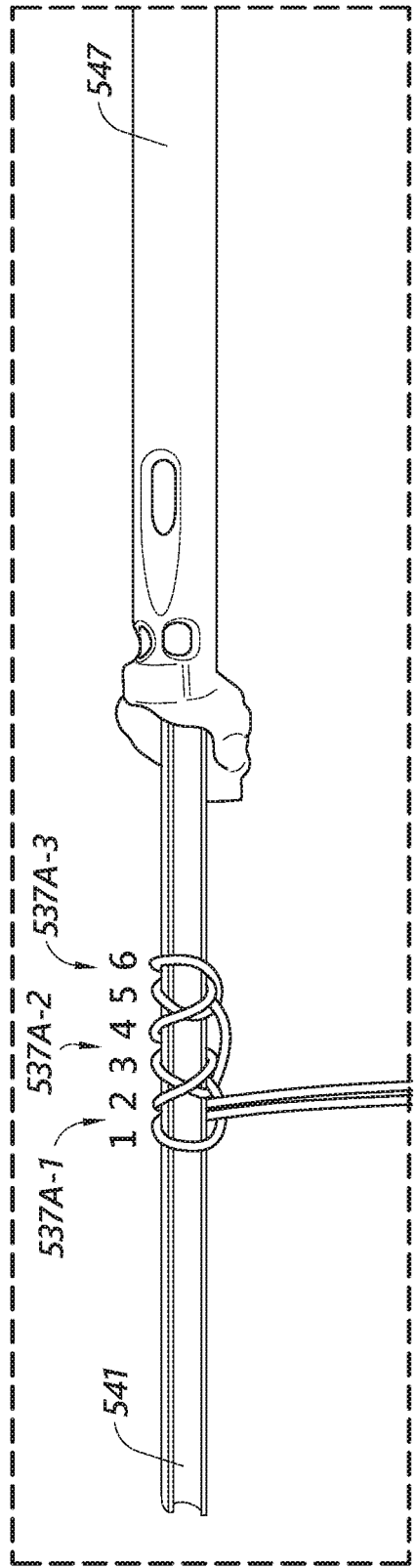

FIGS. 16A-16AK illustrate an example method of forming the knot portion 537A in its delivery configuration (or "ready-state") about the exterior of the knot holder 541 and preparing the locking suture 537 and suture portions for deployment. To begin formation of the knot portion 537A, in this embodiment, as shown in FIGS. 16A-16C, three cow hitches 537A-1, 537A-2, 537A-3 are formed about the knot holder 541 extending distally from the knot end effector 533.

Figure 16D:
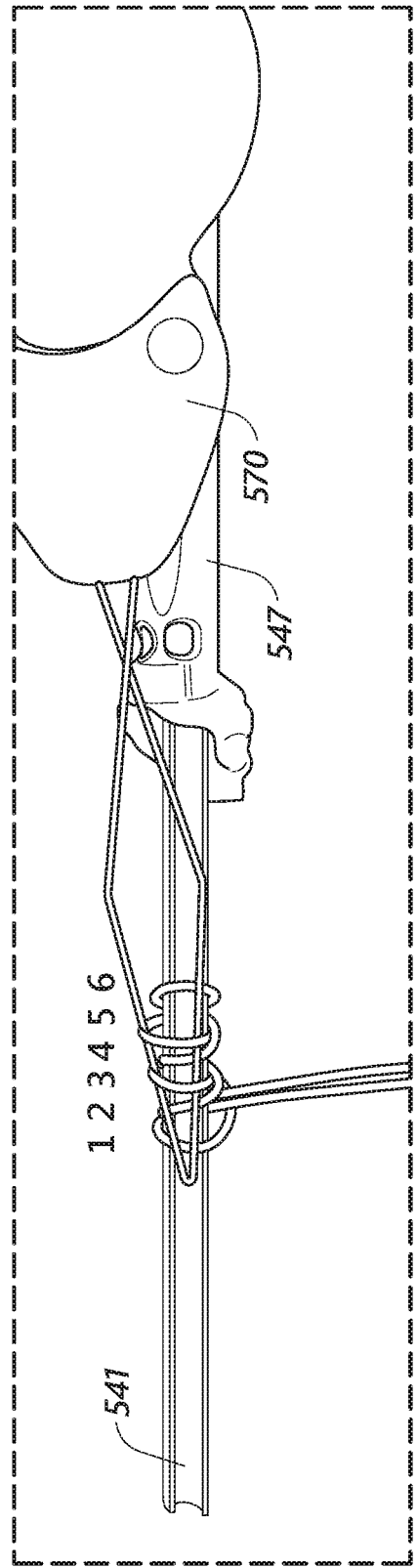
Figure 16E:
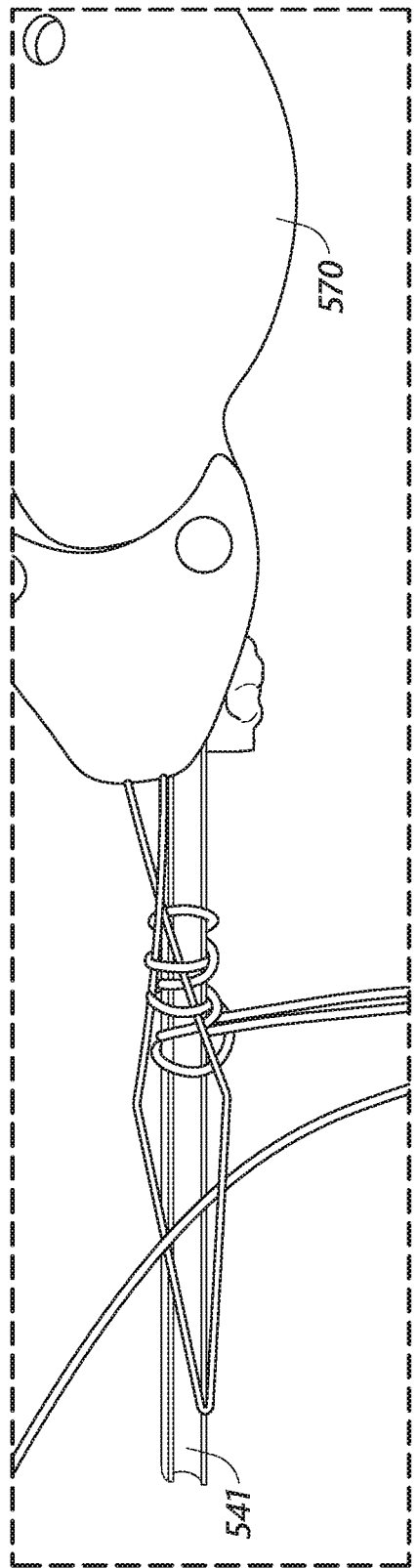
Figure 16F:
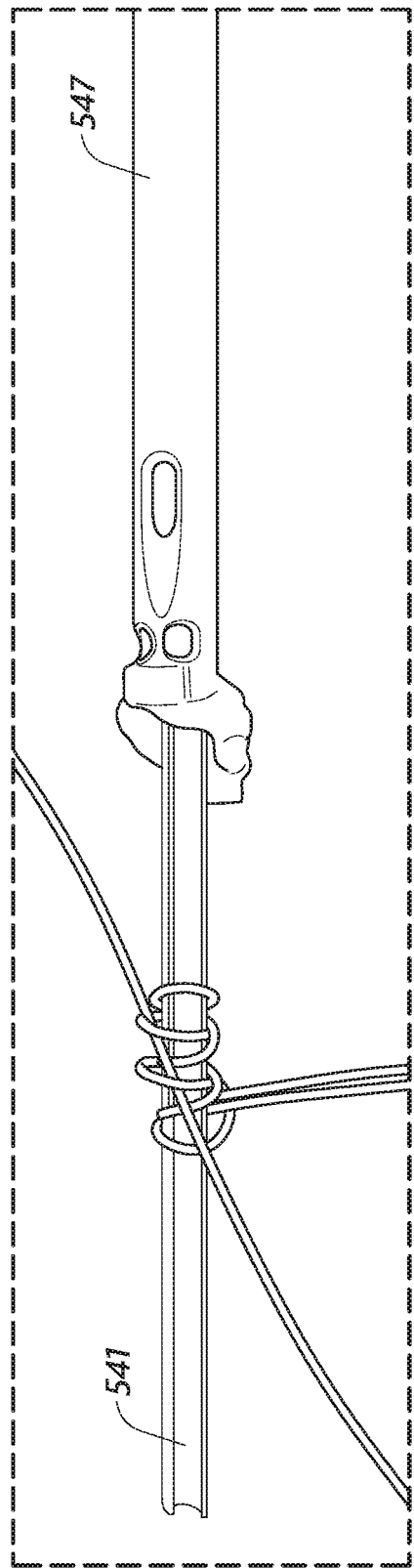

Although in this embodiment three cow hitches are used, in alternative embodiments, any suitable number of cow hitches may be used (e.g., 1, 2, 4, 5, or more cow hitches). The number of cow hitches may be selected based on the particular medical operation and/or the forces that the deployed locking suture 537 is expected to experience. For approximating two tissues within a ventricle of a human heart, for example, it has been found that, in some instances, three cow hitches is sufficient. For ease of illustration, each loop formed about the knot holder 541 is labeled and/or referred to as loop 1 through loop 6 (from left to right, or distal to proximal). Each cow hitch defines two loops. Specifically, the first cow hitch 537A-1 defines loop 1 and loop 2, the second cow hitch 537A-2 defines loop 3 and loop 4, and the third cow hitch 537A-3 defines loop 5 and loop 6, as illustrated and labeled in FIGS. 16C and 16D. After the three cow hitches are formed, a wire threader 570 is used to thread the free ends of the locking suture 537 to further form the knot portion 537. Specifically, as shown in FIG. 16D, the wire threader 570 is inserted through loop 3 and loop 5, and then, as shown in FIG. 16E, the first free end extending from loop 1 of the first cow hitch 537A-1 is threaded through a loop of the wire threader 570. Next, the wire threader 570 is withdrawn from loops 3 and 5, thereby threading or pulling the first free end through loops 3 and 5, as shown in FIG. 16F.

Figure 16G:
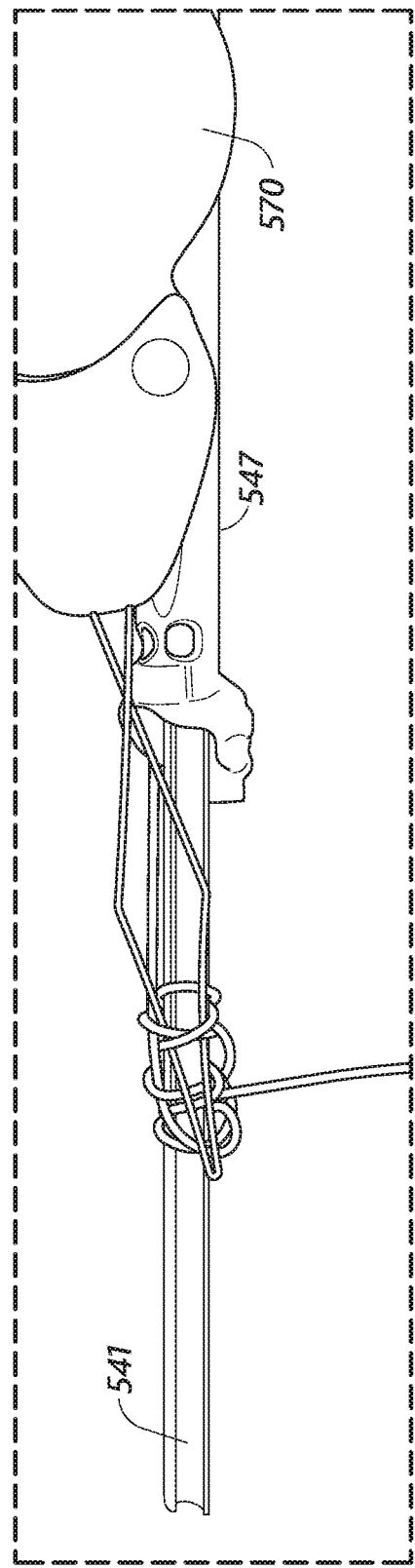
Figure 16H:
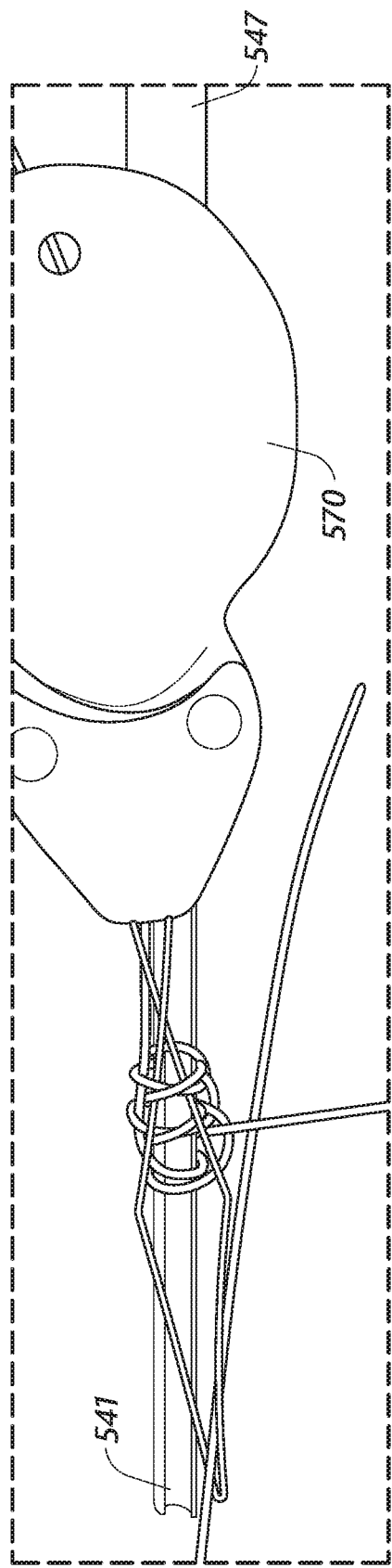
Figure 16I:
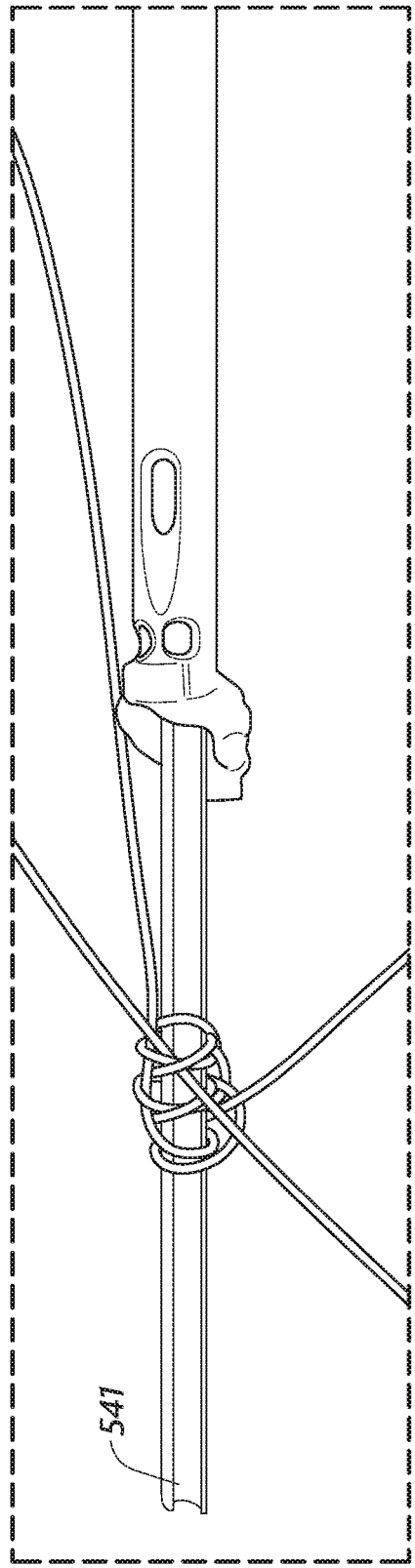
Figure 16J:
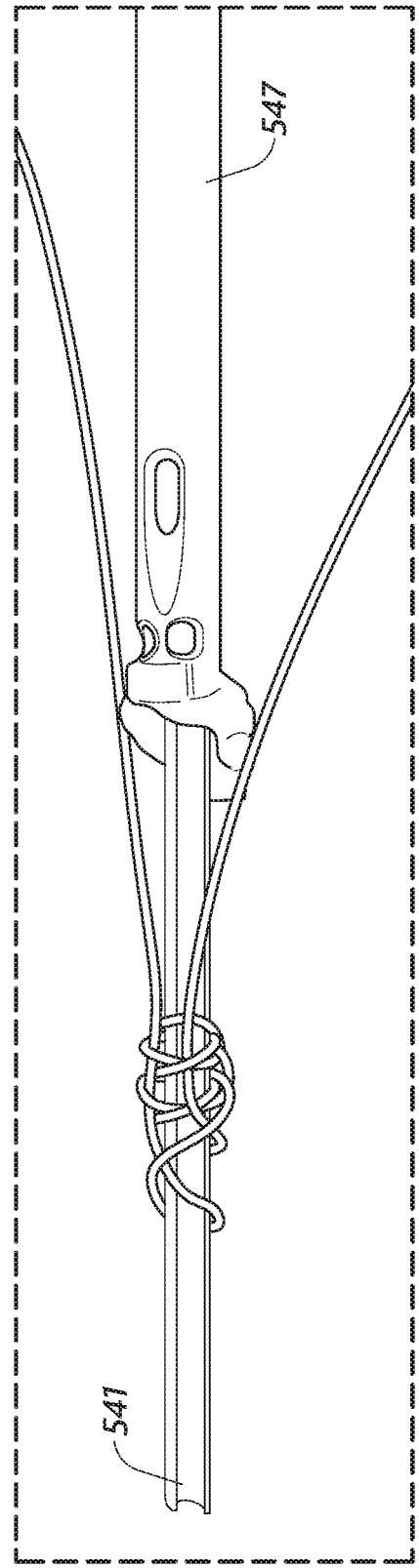

Further, as shown in FIG. 16G, the wire threader 570 is inserted through loop 4 and loop 5, and then, as shown in FIG. 16H, the second free end of the locking suture 537 extending from loop 2 of the first cow hitch 537A-1 is threaded through the loop of the wire threader 570. Next, the wire threader 570 is withdrawn from loops 4 and 5, thereby threading or pulling the second free end through loops 4 and 5, as shown in FIG. 16I. FIG. 16J illustrates the knot portion 537A after the first free end is threaded through loops 3 and 5 and the second free end is threaded through loops 4 and 5, as described above.

Next, the wire threader 570 is inserted through loop 5 and loop 6, as shown in FIG. 16K, and then, as shown in FIG. 16L, the first free end of the locking suture 537 is threaded through the loop of the wire threader 570. Next, the wire threader 570 is withdrawn from loops 5 and 6, thereby threading or pulling the first free end through loops 5 and 6, as shown in FIGS. 16M and 16N.

Figure 16O:
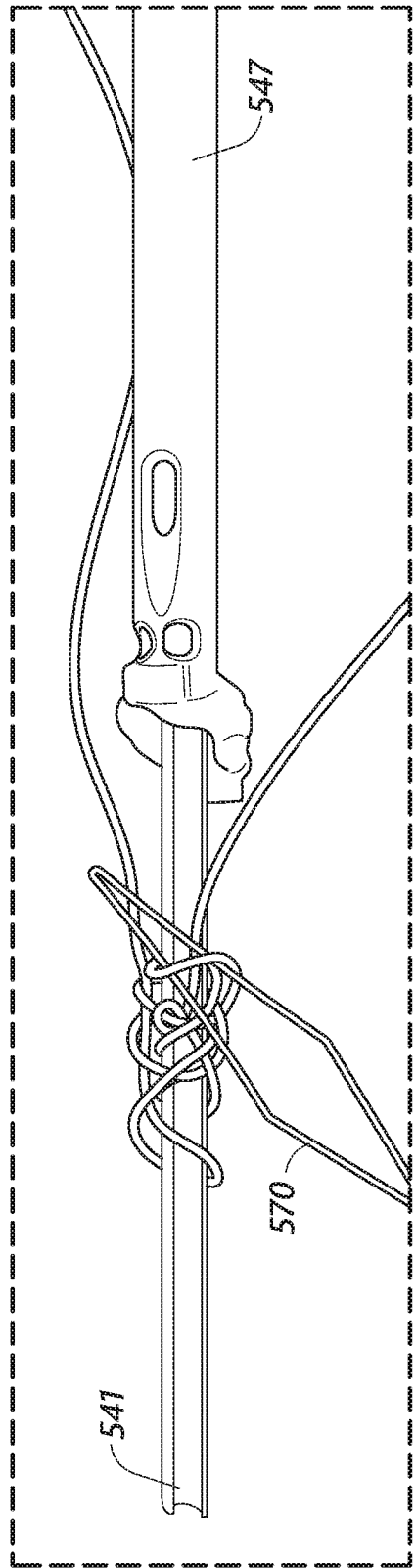
Figure 16P:
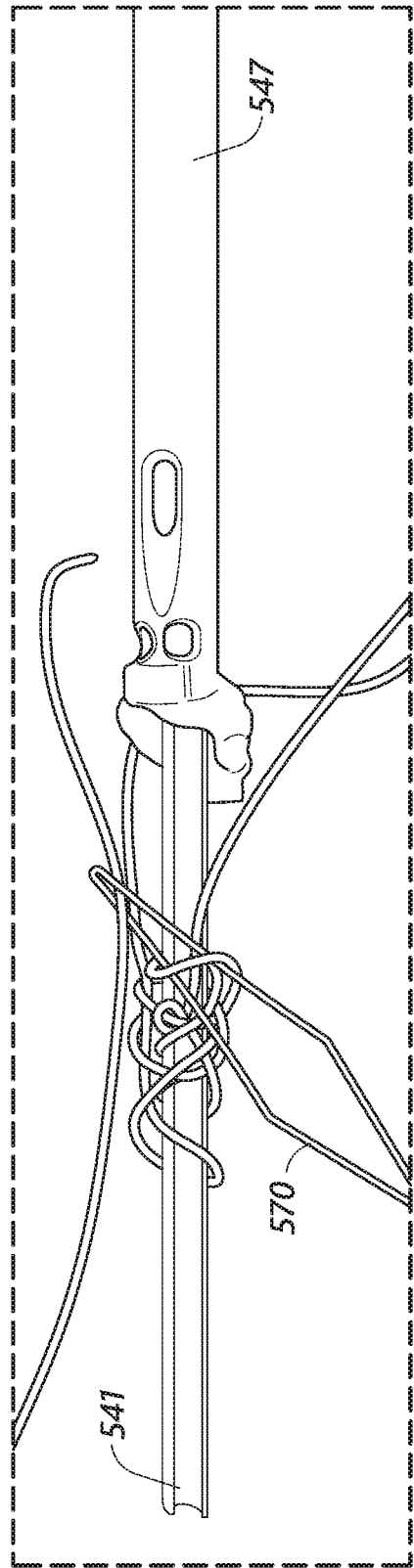
Figure 16Q:
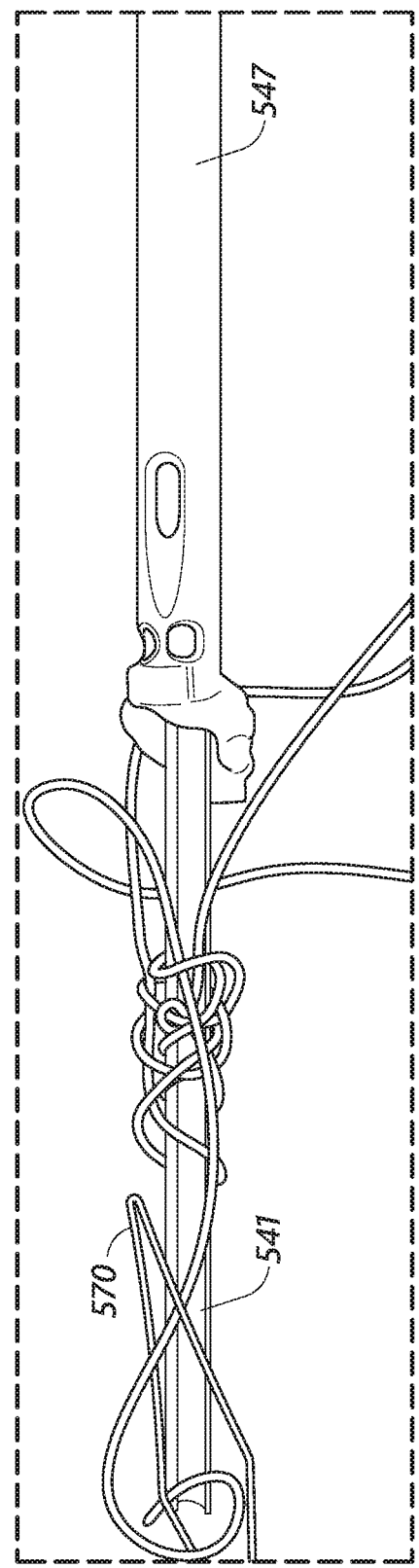

Further, as shown in FIG. 16O, the wire threader 570 is inserted through loop 6 proximally, and then, as shown in FIG. 16P, the second free end of the locking suture 537 is threaded through the loop of the wire threader 570. Next, the wire threader 570 is withdrawn distally from loop 6, thereby threading or pulling the second free end through loop 6 distally, as shown in FIGS. 16Q and 16R.

Figure 16R:
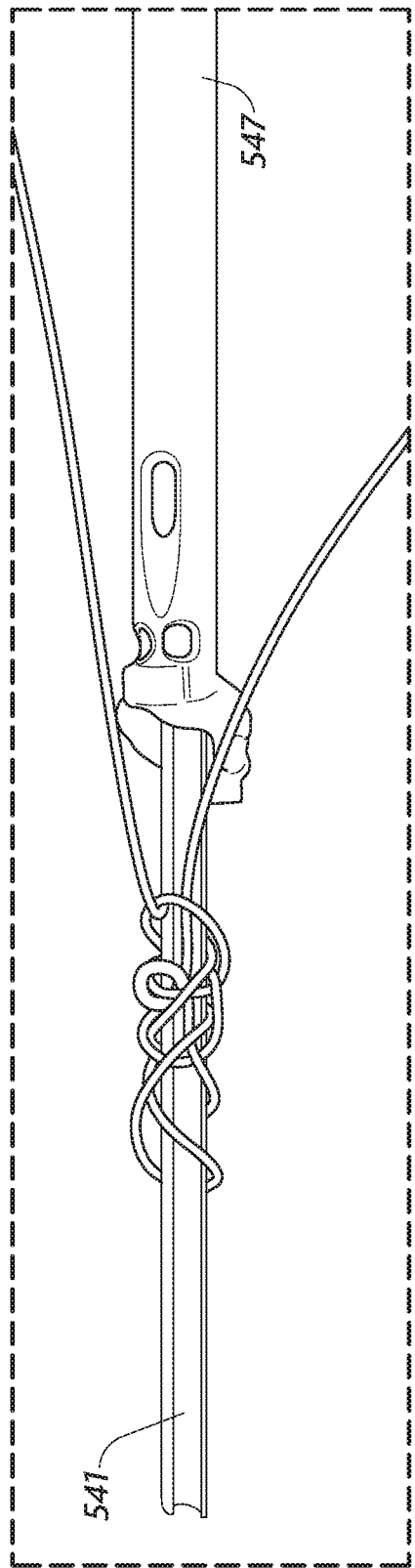
Figure 16S:
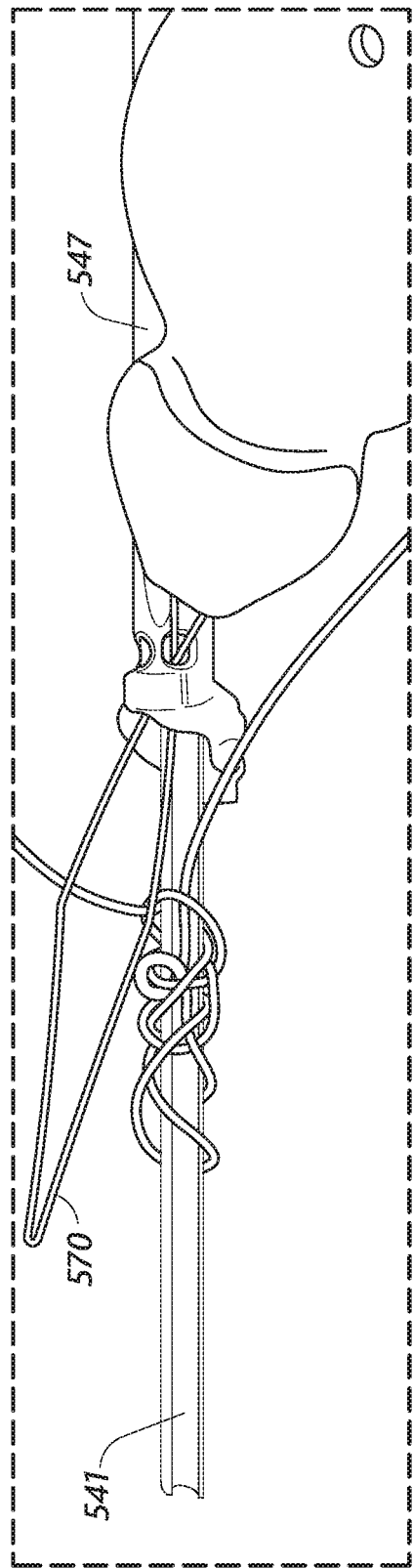
Figure 16T:
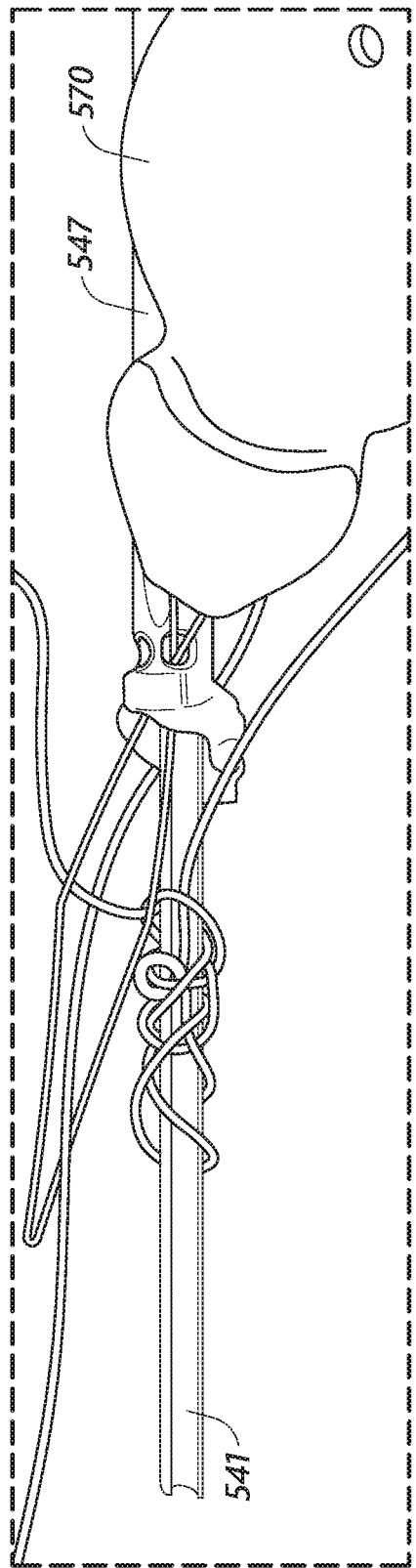
Figure 16U:
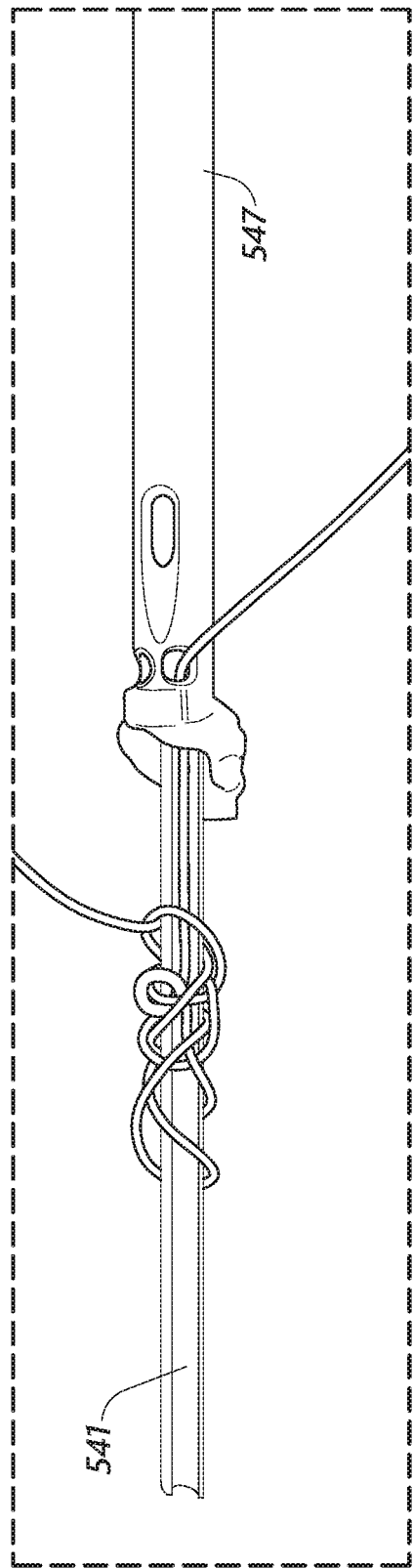
Figure 16V:
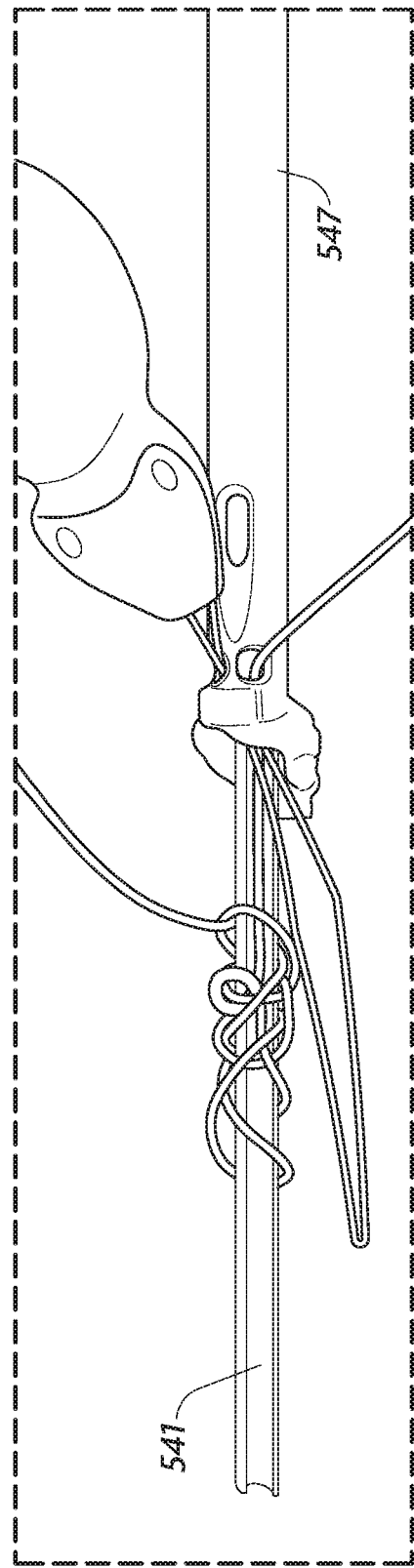
Figure 16W:
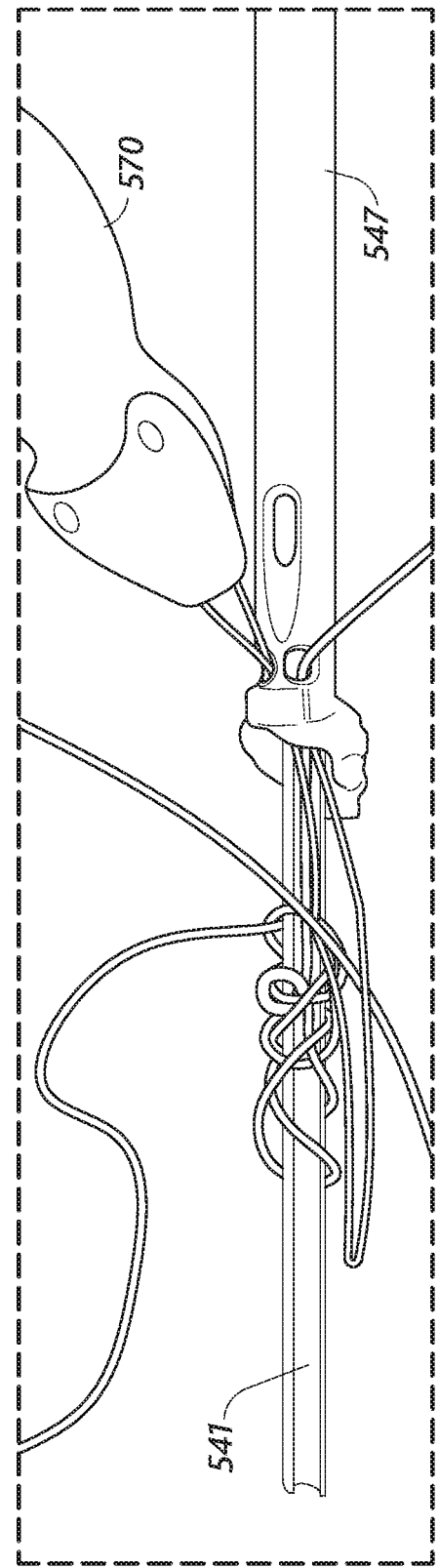
Figure 16X:
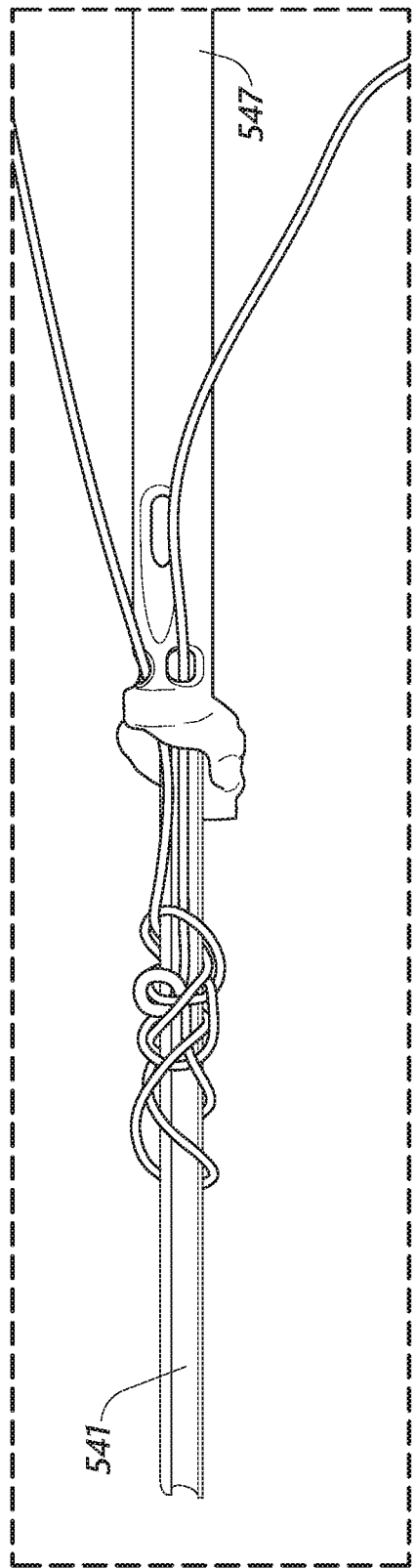

With the knot portion 537A formed about the knot holder 541, as shown in FIG. 16R, the free ends can be threaded through the knot pusher 547. Specifically, as shown in FIG. 16S, the wire threader 570 is inserted distally through the first aperture 547A, and then, as shown in FIG. 16T, the first free end of the locking suture 537 is threaded through the loop of the wire threader 570. Next, the wire threader 570 is withdrawn proximally from the first aperture 547A, thereby threading or pulling the first free end of the locking suture 537 through the first aperture 547A, as shown in FIG. 16U. Similarly, as shown in FIG. 16V, the wire threader 570 can be inserted distally through the second aperture 547B, and then, as shown in FIG. 16W, the second free end of the locking suture 537 is threaded through the loop of the wire threader 570. Next, the wire threader 570 is withdrawn proximally from the second aperture 547B, thereby threading or pulling the second free end of the locking suture 537 through the second aperture 547B, as shown in FIG. 16X.

Figure 16Y:
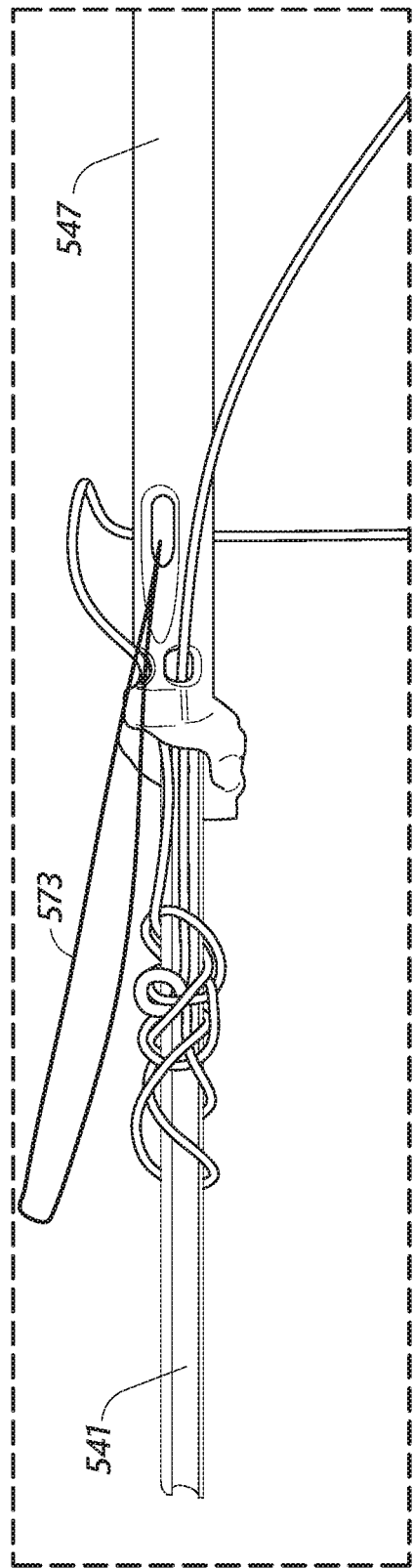
Figure 16Z:
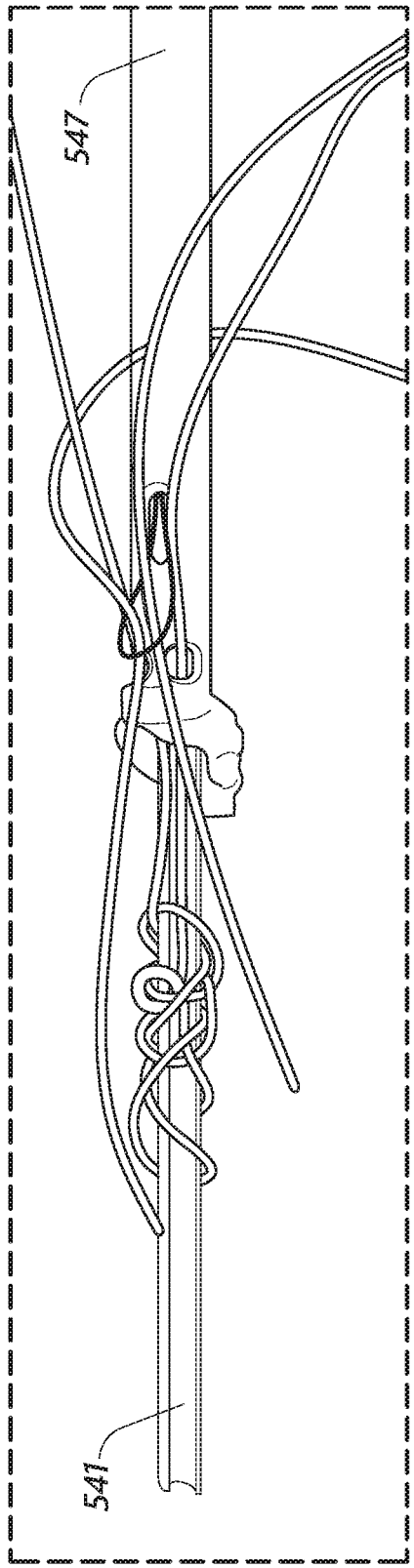
Figure 16A:
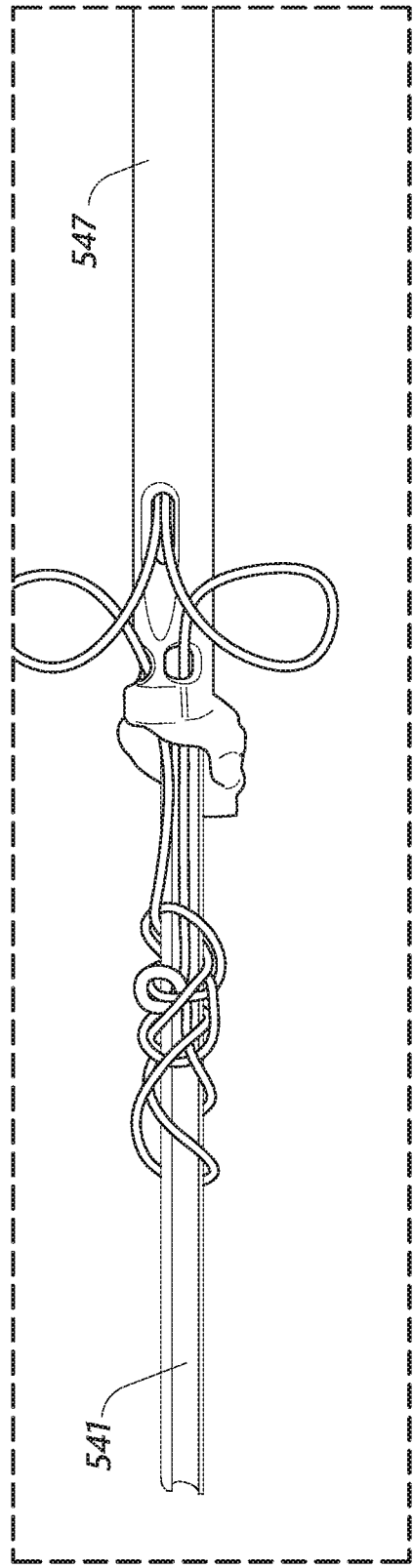
Figure 16A:
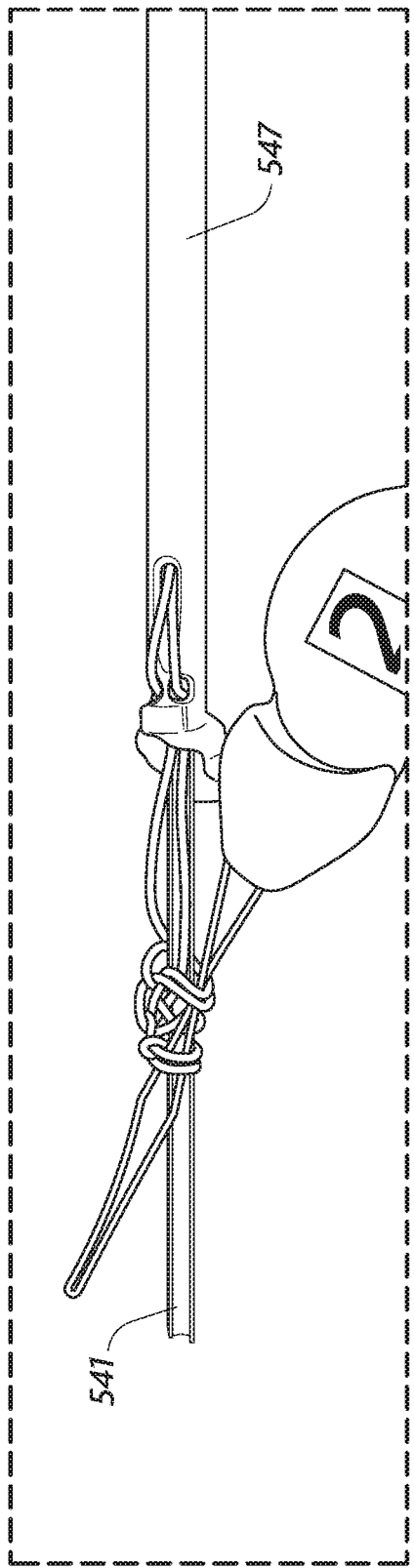
Figure 16A:
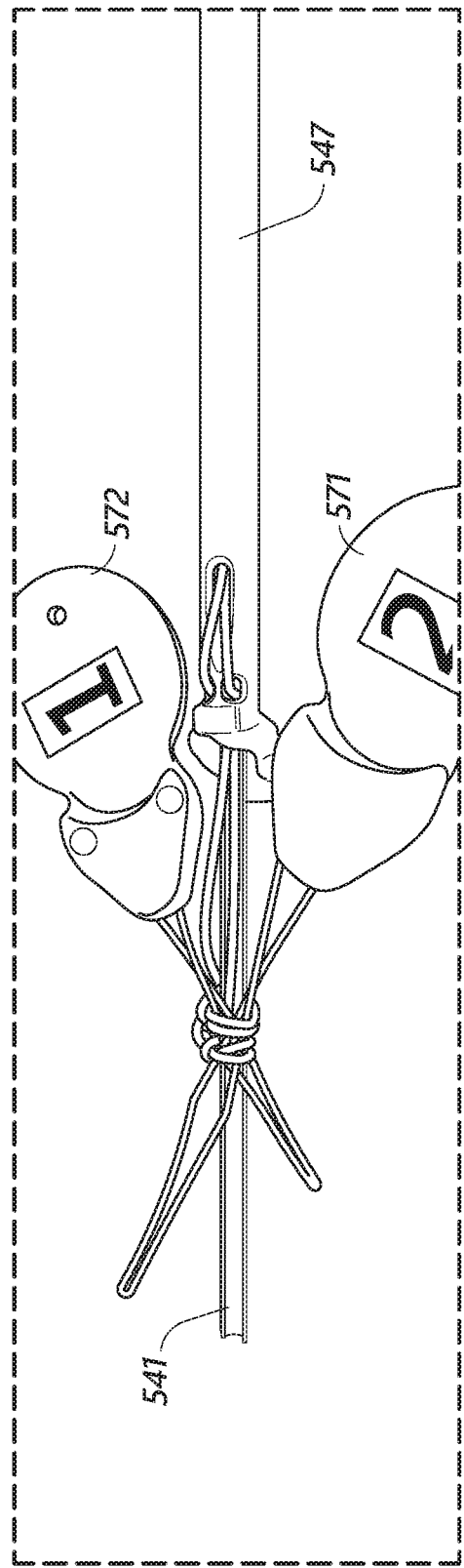
Figure 16A:
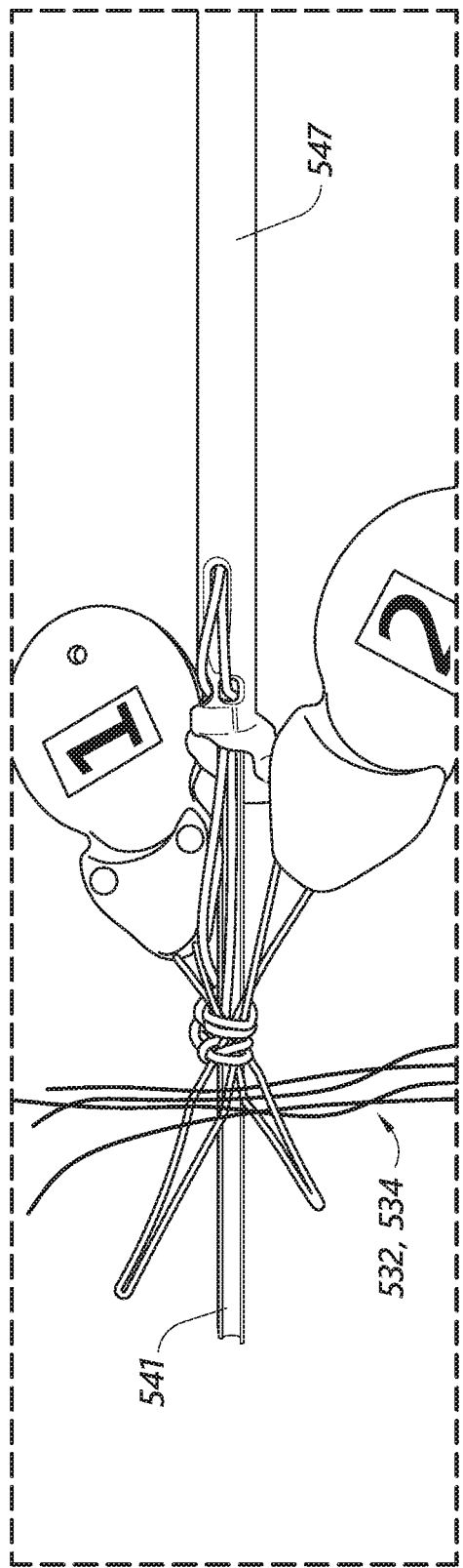
Figure 16A:
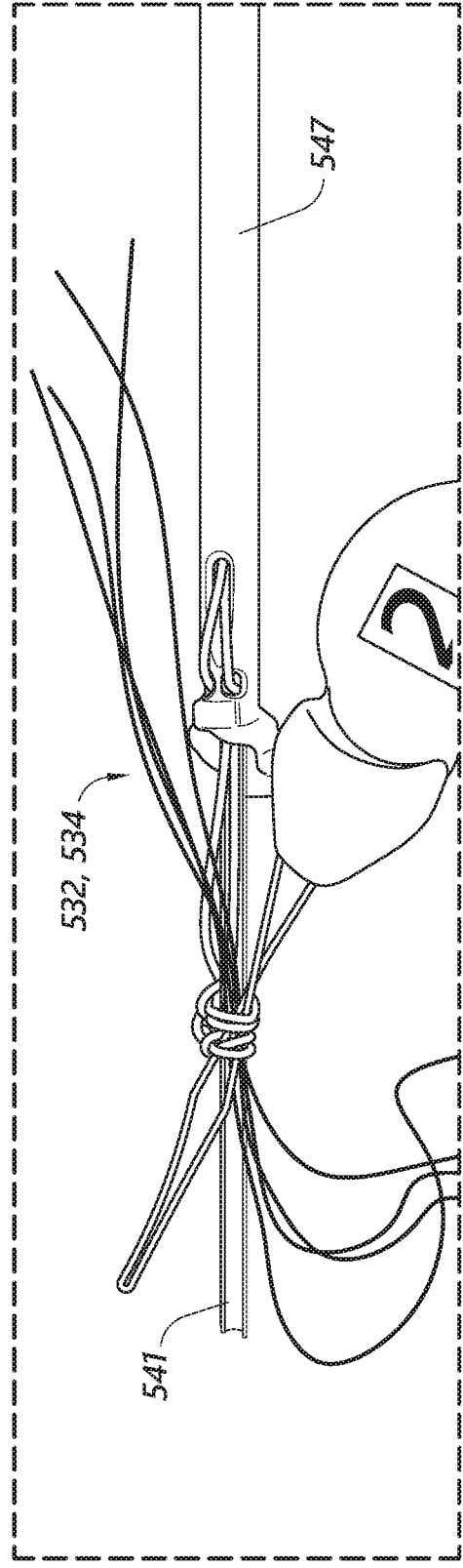
Figure 16A:
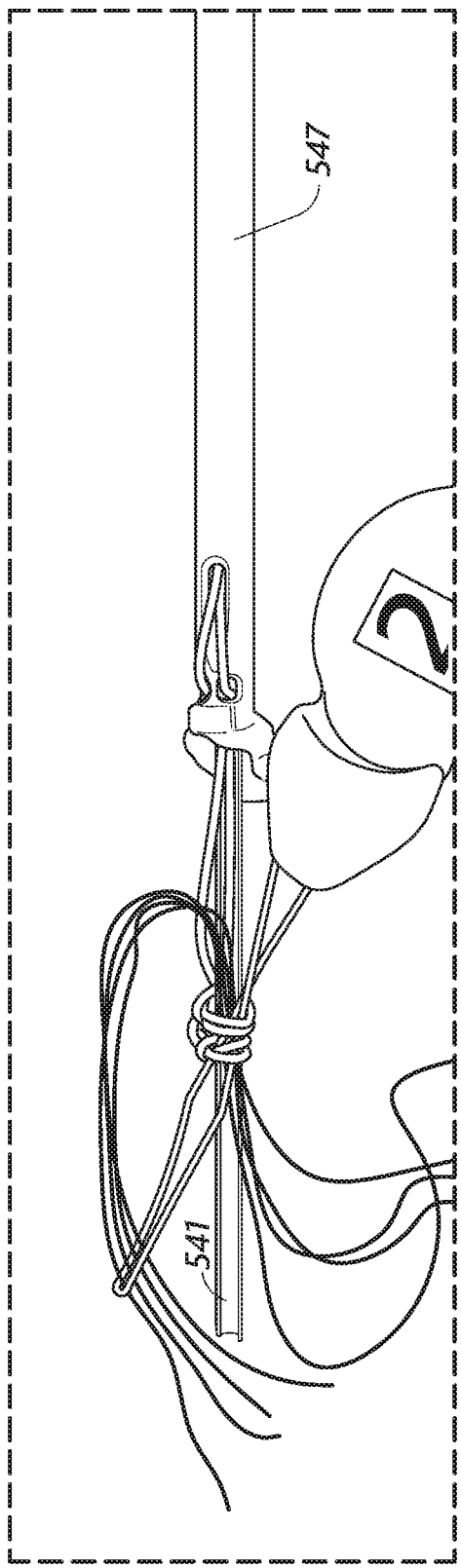
Figure 16A:
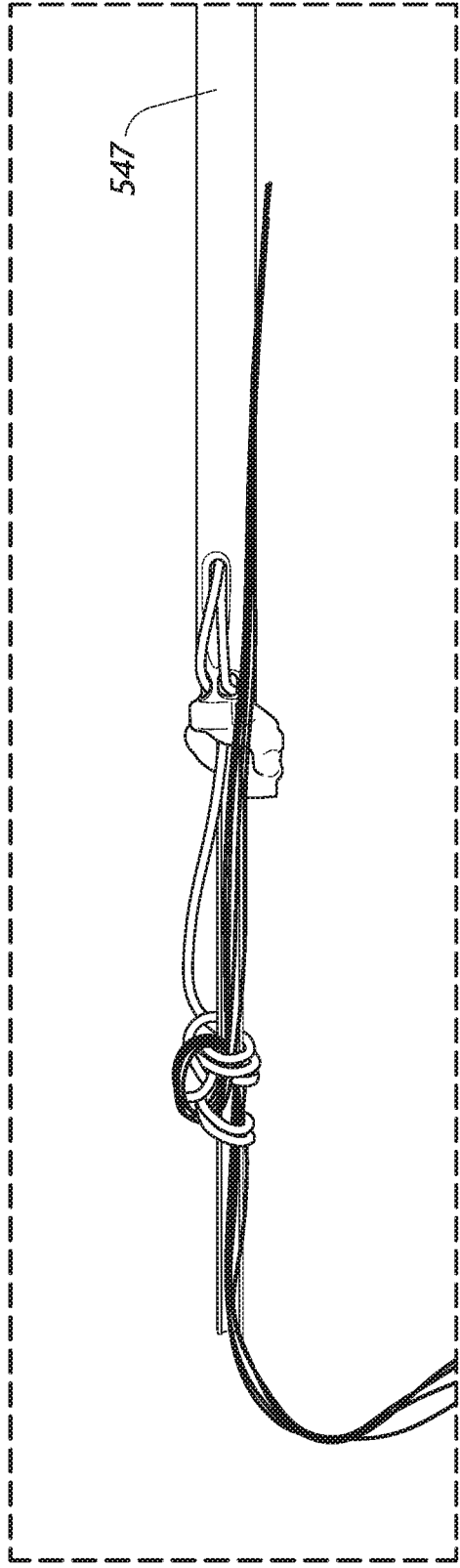
Figure 16A:
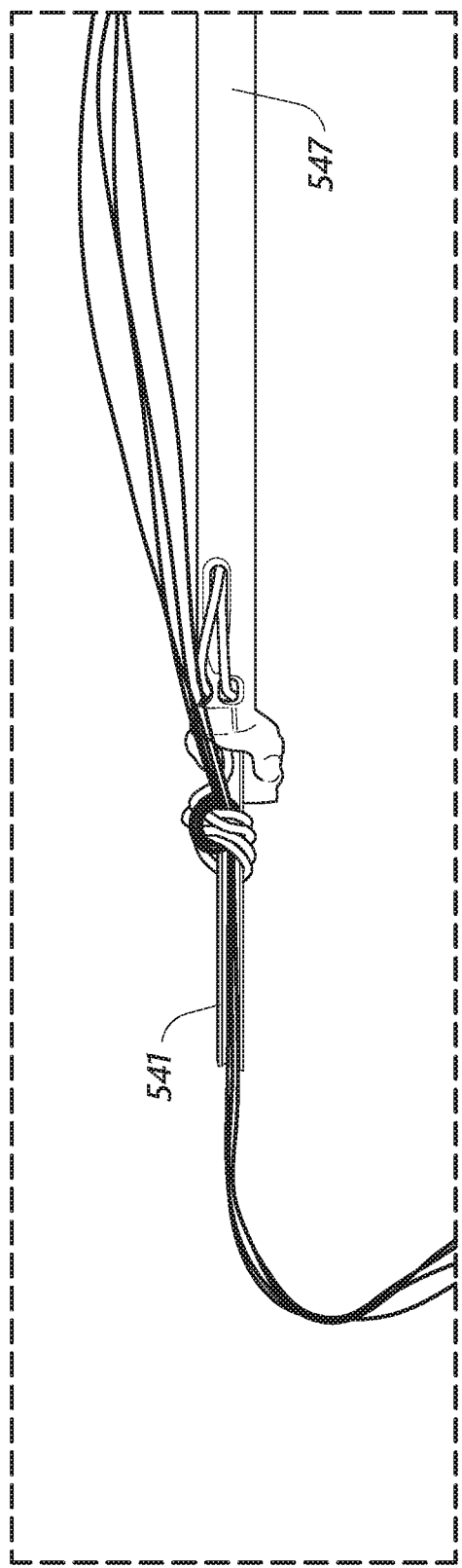
Figure 16A:
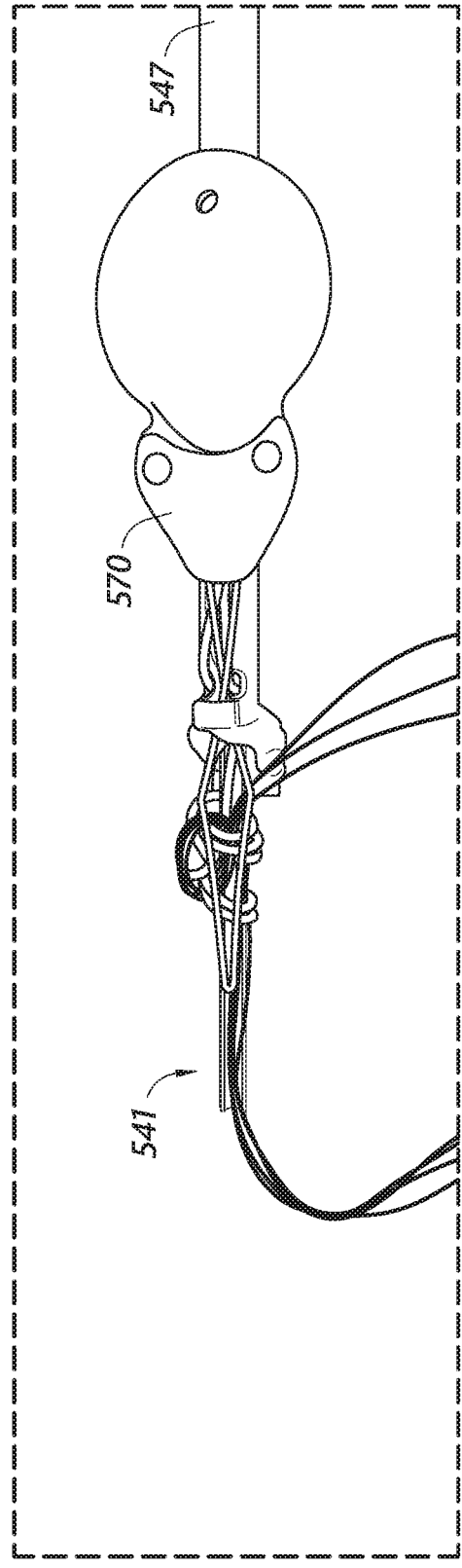
Figure 16A:
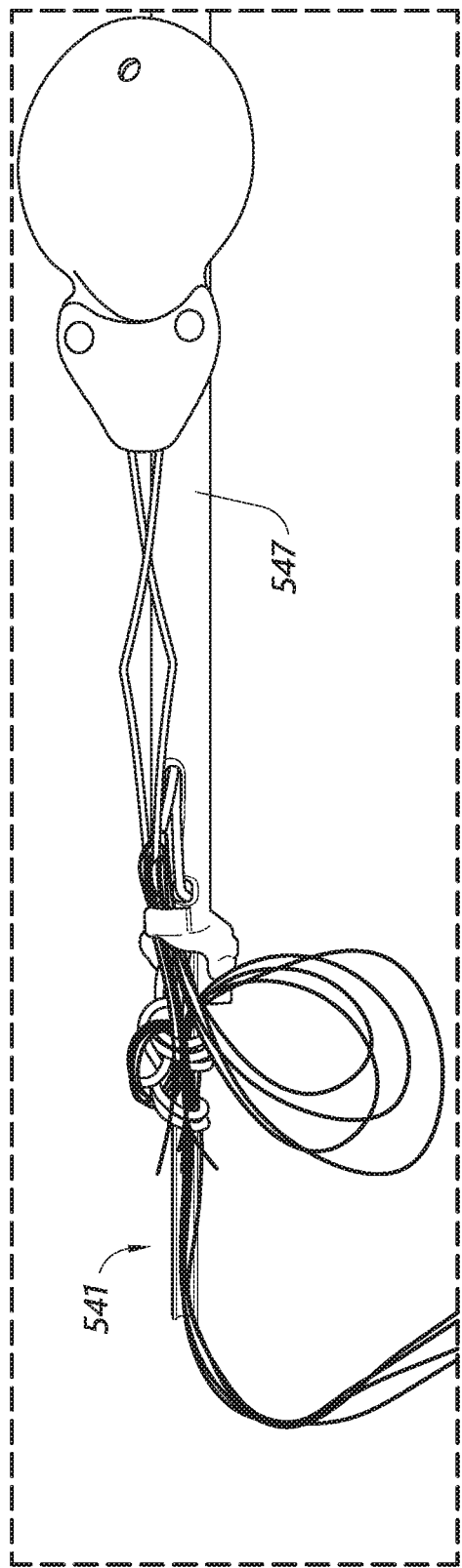
Figure 16A:
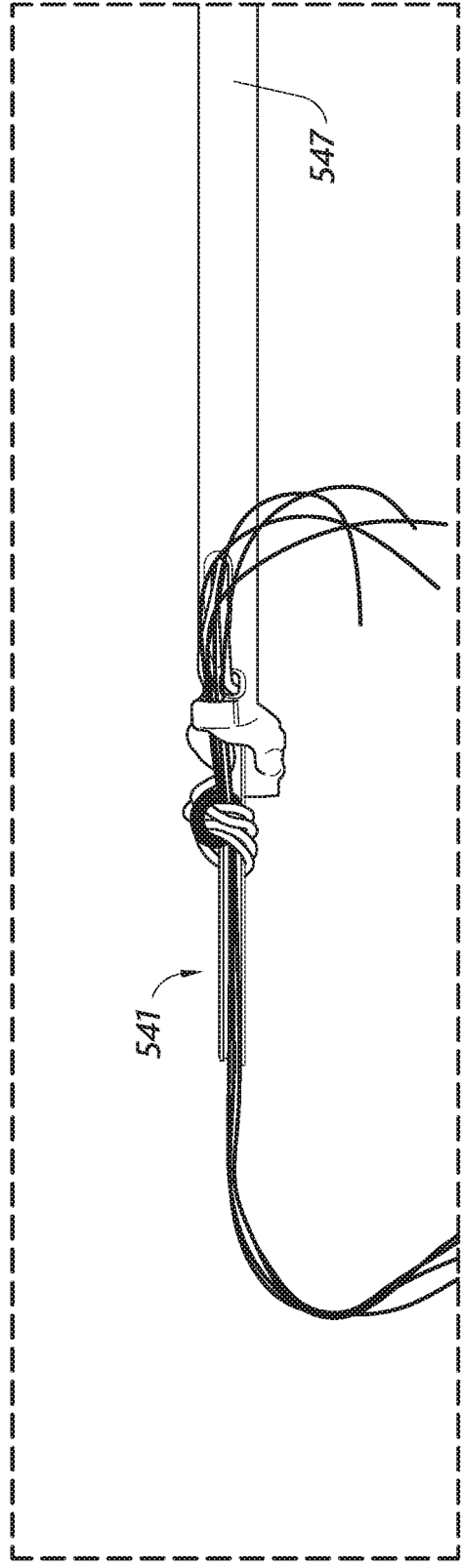
Figure 16A:
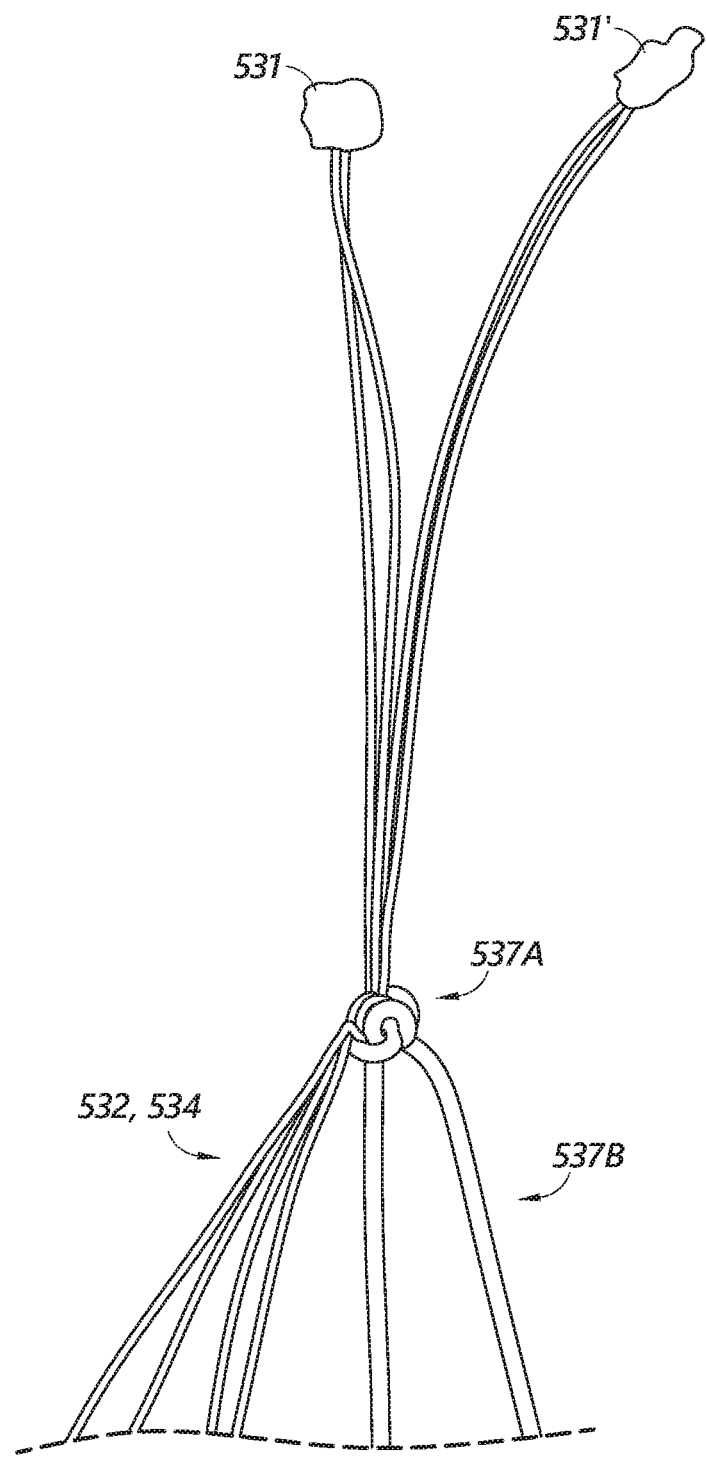

Next, a wire threader 573 is inserted distally into and through the proximal end portion (not shown) of the knot pusher 547, through the lumen of the knot pusher 547, and exiting the third aperture 547C, as shown in FIG. 16Y. Note that as shown the wire threader 573 is longer than the wire threader 570 because the wire threader 573 needs to be long enough to extend through the length of the knot pusher from its proximal end to the third aperture 547C (in some instances, a single wire threader can be configured to be used to perform the functions described herein with respect to both the wire threader 570 and 573). With the loop of the wire threader 573 extending from within the lumen of the knot pusher 547 and through the third aperture 547C, both the first free end and the second free end of the locking suture 537 are threaded through the loop of the wire threader 573, as shown in FIG. 16Z, and then the wire threader 573 is withdrawn or pulled proximally through the lumen of the knot pusher 547, thereby threading both the first free end and the second free end of the locking suture 537 (e.g., the tether portion 537B) proximally from the knot portion 537A into and through the lumen of the knot pusher 547, as shown in FIG. 16AA. With the tether portion 537B threaded into the third aperture 547C and proximally through the lumen of the knot pusher 547, the tether portion 537B can be secured or fixed to the LS catch 567 (not shown in FIG. 16AA).

Next, the knot portion 537A can be prepared to receive the suture portions extending from the implants and tissues, as described in previous embodiments, to assist the operator (e.g., surgeon) in threading the free ends of the suture portions through particular portions of the knot portion 537A in a repeatable and efficient manner without compromising the formation of the knot portion 537A. For example, as shown in FIG. 16AB, a first suture portion wire threader 571 is inserted distally through loop 5, around loop 4 and loop 3, and then through loop 2 and loop 1. Further, as shown in FIG. 16AC, a second suture portion wire threader 572 is inserted distally through loops 1-6, e.g., through loop 6, then loop 5, then loop 4, then loop 3, then loop 2, and then loop 1.

At this stage, as shown in FIG. 16AC, the locking suture 537 is prepared to receive the suture portion, and then be delivered along or about the suture portions to a suitable location within the target region for deployment. In some embodiments, a kit can be provided to the operator including any of the components described herein. For example, a kit may include a knot holder and a locking suture 537 coupled thereto, with first suture portion wire threader 571 and second suture portion wire threader 572 disposed through locking suture 537, as shown in FIG. 16AC. In some instances, the kit may include a LS delivery device assembled with the locking suture, knot holder, and knot pusher, as illustrated in various embodiments herein, while in on other instances, the kit may include only portions of the LS delivery device, and/or multiple or duplicate components of the LS delivery device. For example, in some instances, a kit may include a single handle and a single knot pusher, and multiple knot holders each having a locking suture coupled thereto in a delivery configuration, similar to as shown and described with respect to FIG. 16AC. In this manner, an operator can deliver and deploy multiple locking sutures.

For example, as shown in FIG. 16AD, the operator (e.g., surgeon) can thread the free ends of the suture portions 532, 534 through the loop of the first suture portion wire threader 571, and then pull or withdraw proximally the first suture portion wire threader 571, thereby threading the free ends of the suture portions 532, 534 proximally through loops 1-6, as shown in FIG. 16AE. Next, as shown in FIG. 16AF, the operator can thread the free ends of the suture portions 532, 534 through the loop of the second suture portion wire threader 572, and then pull or withdrawn proximally the second suture portion wire threader 572, thereby threading the free ends of the suture portions 532, 534 proximally through loops 1 and 2, around loops 3 and 4, and then through loops 5 and 6, as shown in FIG. 16AG.

Next, while leaving some slack or length (e.g., about 1 to about 2 inches) of the suture portions exposed at the distal end 540 of the LS delivery device 546 (see, e.g., FIG. 16AH) the free ends of the suture portions 532, 534 can be threaded proximally through the alignment loop, slot or guide 533C, and then into the third aperture 547C of the knot pusher 547, e.g., by using a wire threader, as shown in FIGS. 16AI-16AK. The slack or length of suture portions helps keep the knot portion 537A away from the distal tip of the LS delivery device 546 to inhibit and/or prevent the knot portion 537A from falling off (or being displaced distally off of) the knot holder 541 during the threading process. With the free ends of the suture portions 532, 534 threaded proximally through the third aperture 547C in this manner, the LS delivery device 546 is ready to be inserted into the target region (e.g., through an introducer at an apical region of a heart) to deliver and deploy the locking suture 537. Note that the alignment loop, slot, or guide 533C can be a loop configured to completely circumferentially surround the tether portions 532, 534, as shown in FIGS. 15D and 16AJ, or in other instances, the alignment loop, slot, or guide 533C can be a groove as shown, for example, in FIGS. 15E, 15F, and 15I.

As described in previous embodiments, the knot portion 537A can be displaced distally from the knot holder 541, and the knot portion 537 can be slid or delivered along or about the suture portions 532, 534 to a suitable location within the target region, and then the LS delivery device 546 can be actuated to deploy the locking suture 537 such that the knot portion 537A secures, locks, or otherwise inhibits relative movement between the portions of the suture portions 532, 534 physically engaged with the knot portion 537A. The deployed knot portion 537A is illustrated in FIG. 16AL. As shown, the suture portions 532, 534 extending from the implants 531, 531' are secured within the knot portion 537A of the suture lock 537, and the free ends of the suture portion 532, 534, and the free ends of the locking suture 537 (e.g., the tether portion 537B) extend proximally from the knot portion 537B. The free ends of the suture portions 532, 534 and the tether portion 537B of the locking suture 537 can then be suitably tensioned and secured in a suitable location (e.g., via a proximal anchor outside of the target region, as described in connection with previous embodiments).

Either during deployment of the knot portion 537A and/or after deployment and when anchoring and tensioning the tether portion 537B of the locking suture 537, pulling proximally or tensioning the second free end of the tether portion 537B will cause the knot portion 537A to radially compress or constrict, and pulling proximally or tensioning the first free end of the tether portion 537B will cause the proximal end and the distal end of the knot portion 537A to approximate, e.g., laterally and/or angularly relatively deflect, as described, for example, with respect to the knot portion 537A. As such, during tensioning of the tether portion 537B, it is preferable to pull or tension the second free end of the tether portion 537B before pulling or tensioning the first free end of the tether portion 537B to limit or prevent loose loops or coils in the knot portion 537A when approximating the proximal and distal ends of the knot portion 537A.

In instances in which the implants 531, 531' are secured within a heart and to heart valve leaflets, for example, deploying and anchoring the locking suture 537 in the manner described above can put the valve leaflets in a desirable edge-to-edge relationship. Further, in addition to or instead of creating the edge-to-edge relationship, to promote a larger surface of coaptation, the implants 531, 531' can be secured together to pull or otherwise move the posterior annulus towards the anterior leaflet and/or the anterior annulus towards to posterior leaflet, thereby reducing the distance between the anterior annulus and the posterior annulus, e.g., the septal-lateral distance by about 10%-40%. Approximating the anterior annulus and the posterior annulus in this manner can decrease the valve orifice, and thereby decrease, limit, or otherwise prevent undesirable regurgitation.

In some implementations, the tether portion 537B and/or the free ends of the suture portions 532, 534 can be selectively tensioned (e.g., pulled proximally while monitoring the valve leaflets and any associated regurgitation). After confirming the desirable tension and heart function (e.g., reduced or a suitable amount of regurgitation), the tether portion 537B and the suture portions 532, 534 can be anchored (e.g., outside the apex of the ventricle) using knots, a pledget, a pad, or any other suitable anchoring mechanism.

Figure 17E:
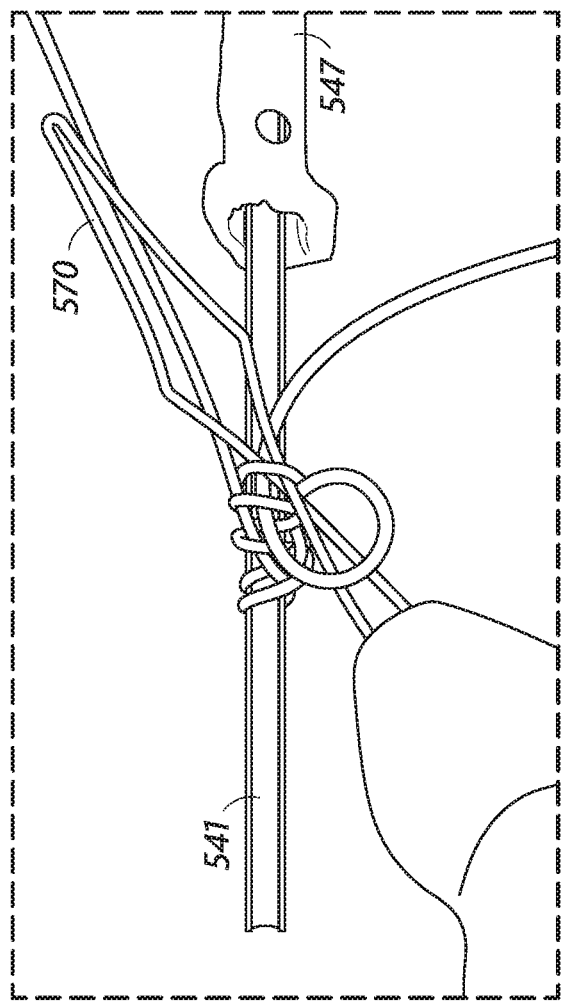
Figure 17F:
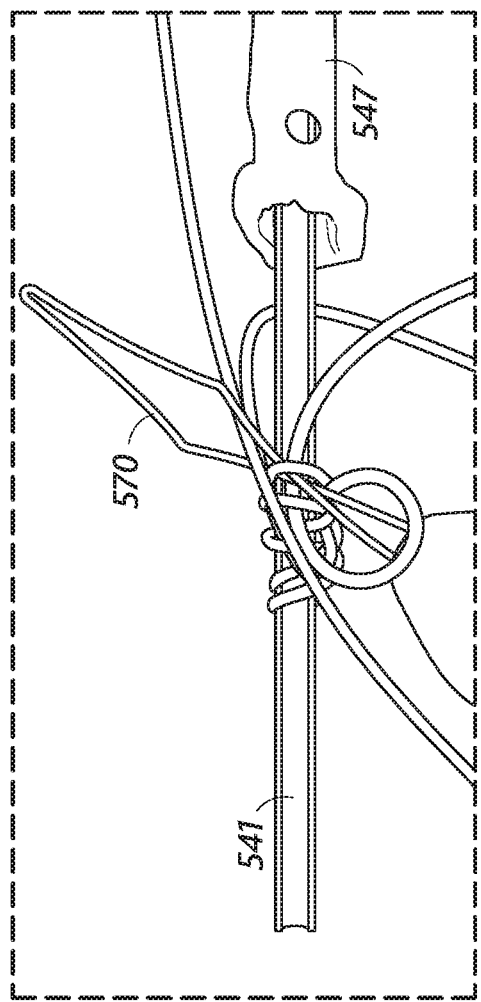
Figure 17G:
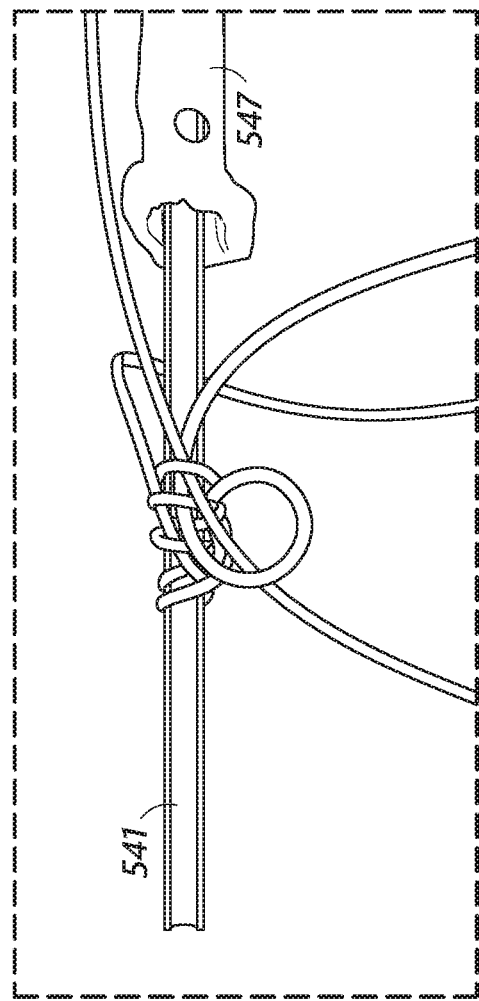
Figure 17H:
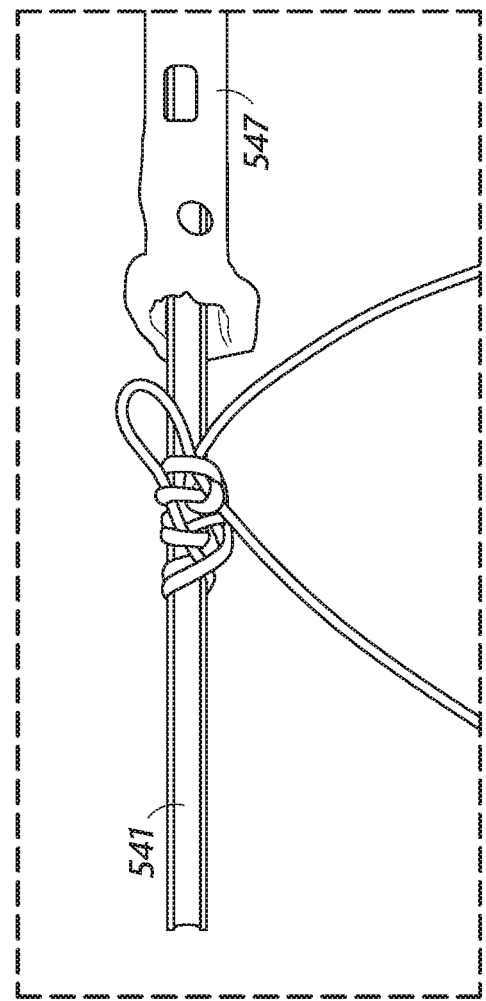
Figure 17I:
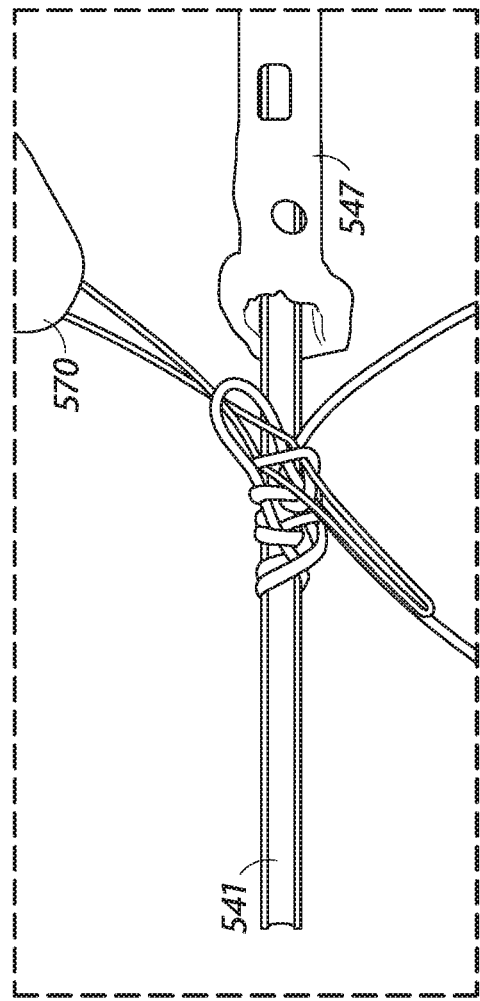
Figure 17J:
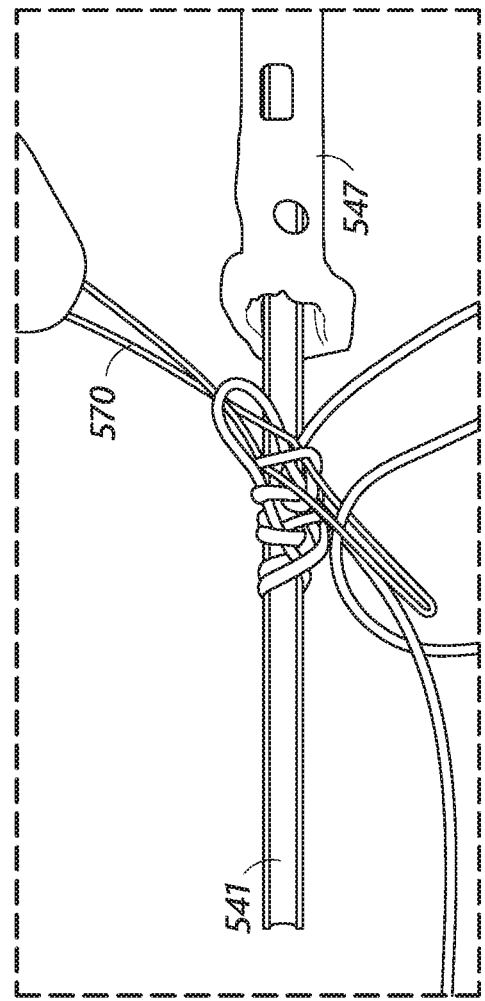
Figure 17K:
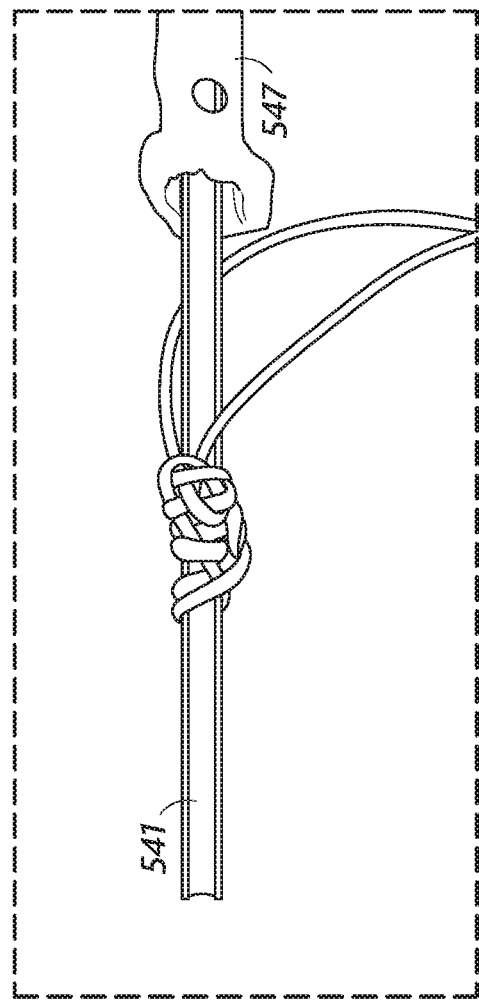
Figure 17L:
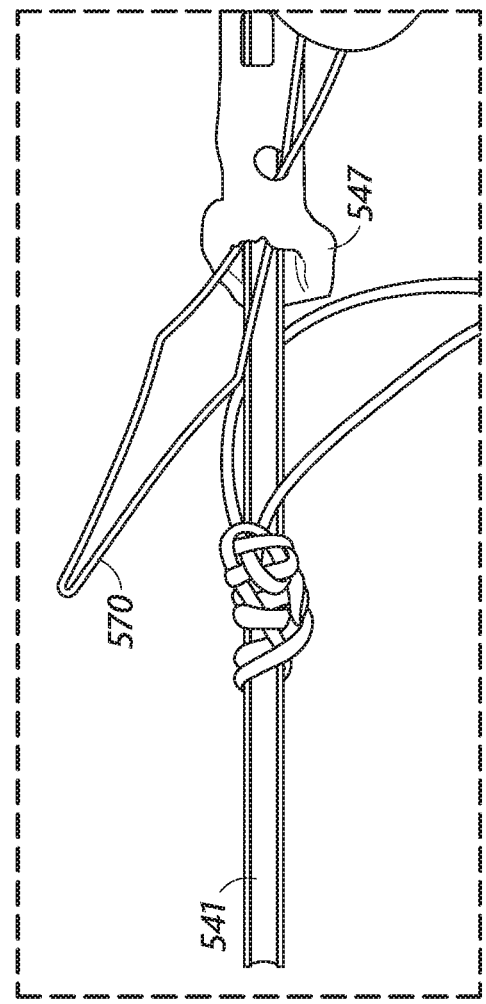
Figure 17M:
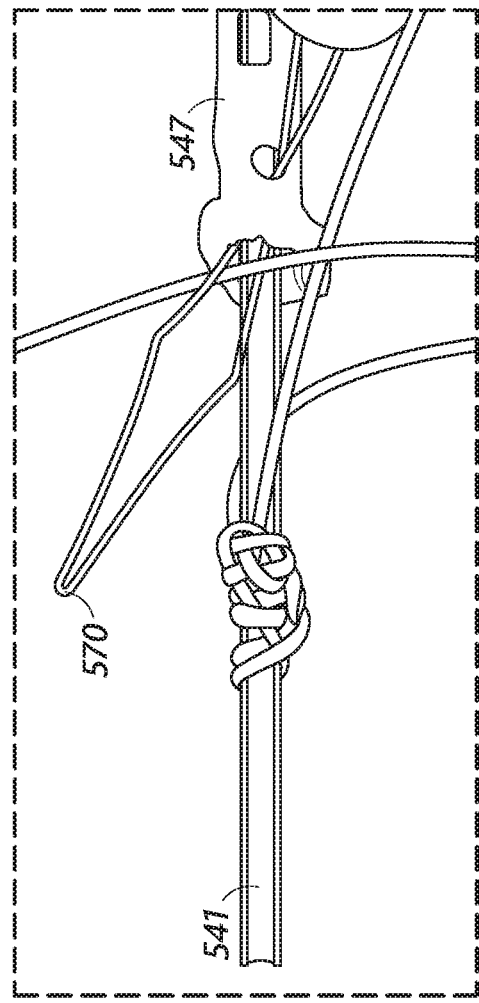
Figure 17N:
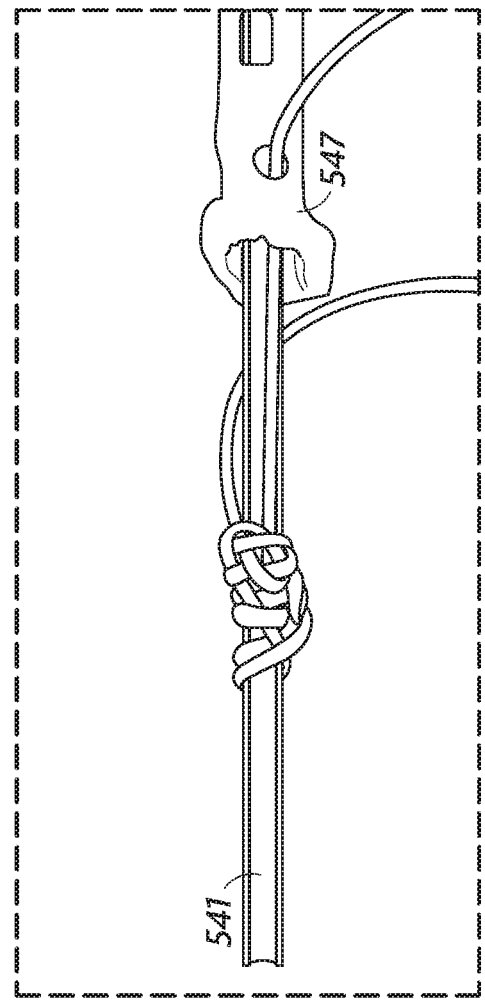
Figure 17O:
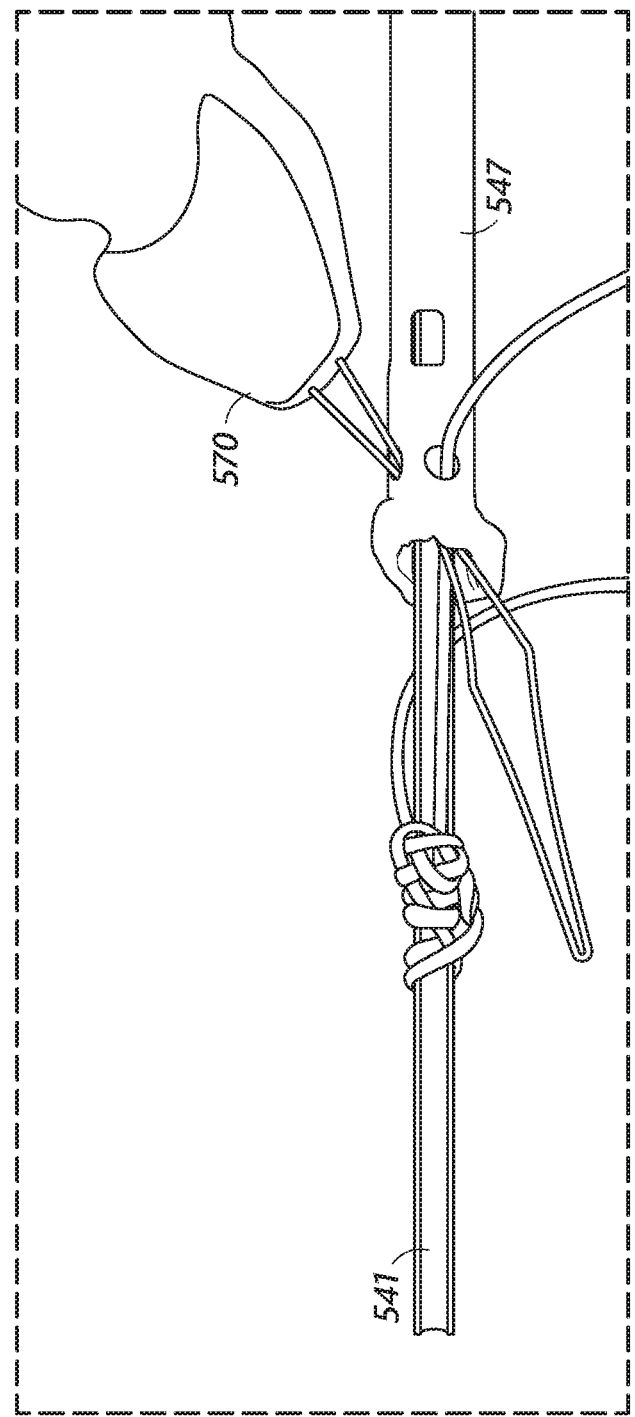
Figure 17R:
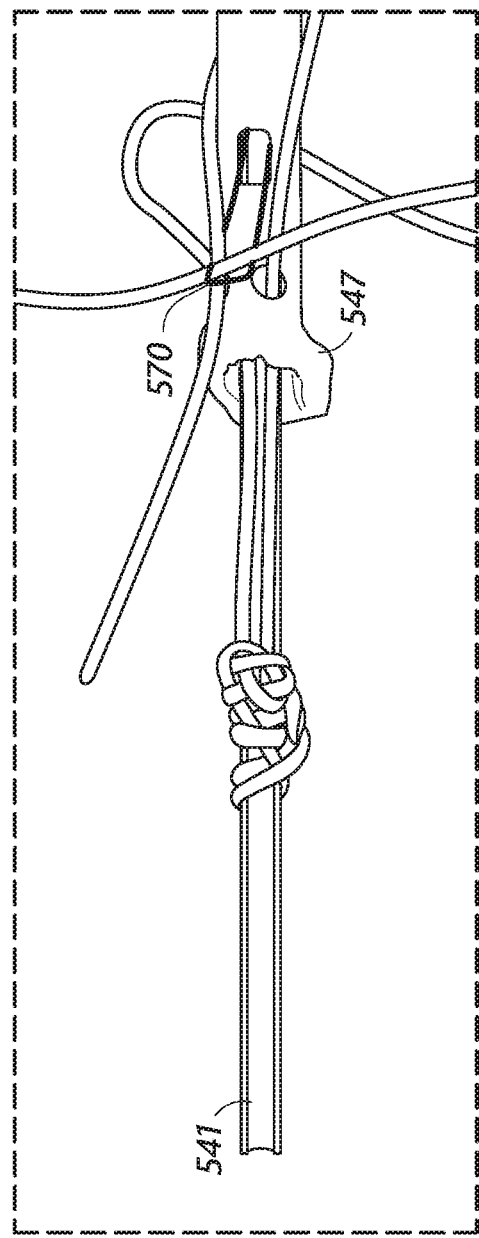
Figure 17S:
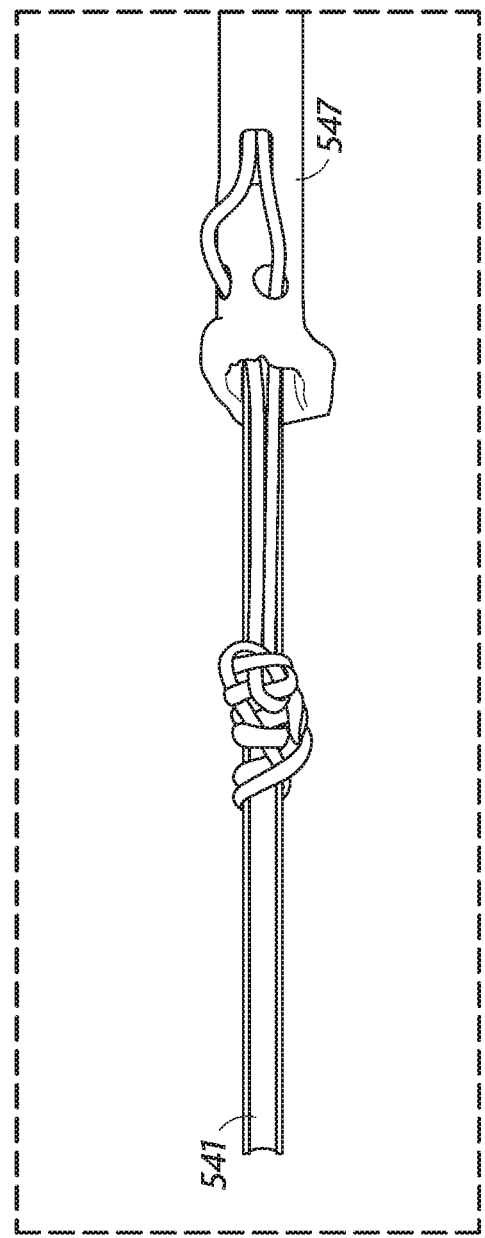
Figure 17T:
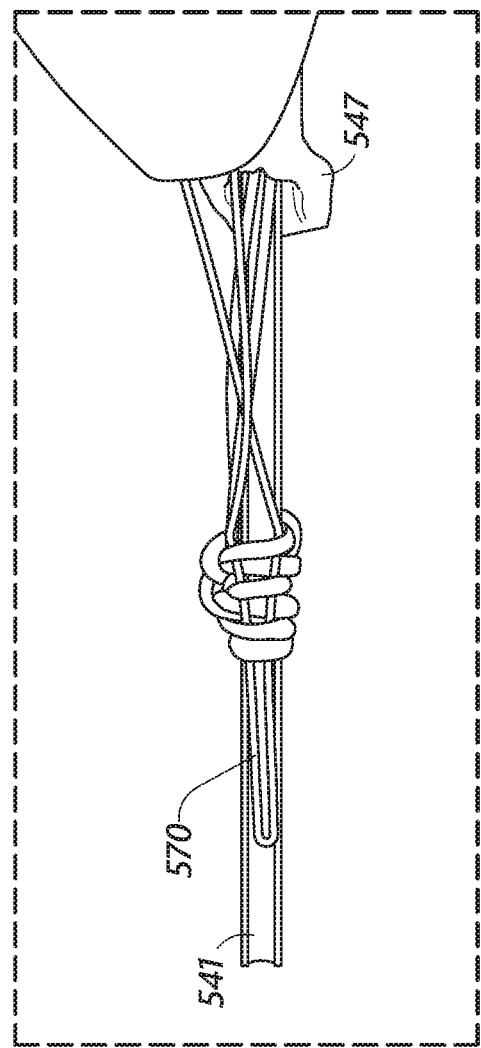
Figure 17W:
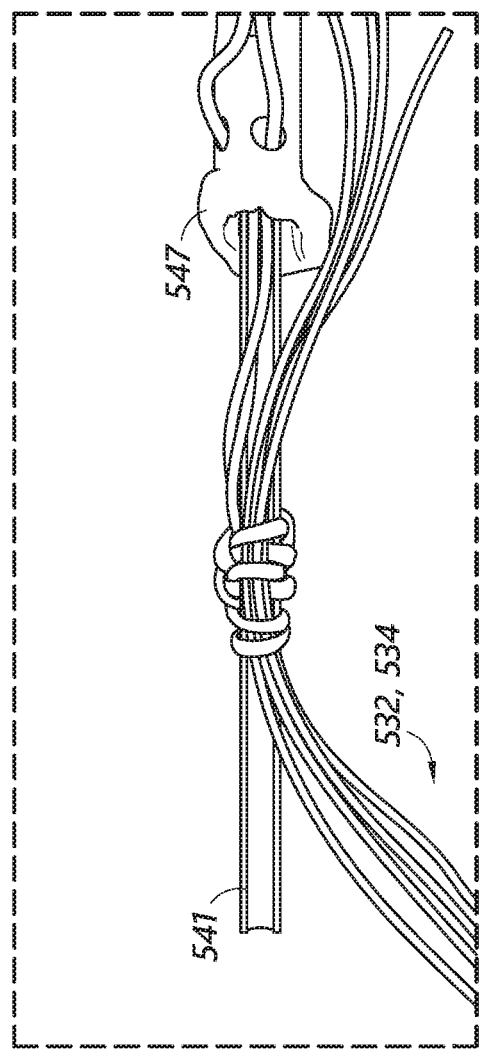

FIGS. 17A-17W illustrate an alternate method of forming the locking suture described with reference to FIGS. 16A-16AK. Beginning after the step illustrated in FIG. 16J (which corresponds to the step illustrated in FIG. 17A), the threader 570 is threaded under loops 5 and 6, as illustrated in FIG. 17B. The second free end is looped through the threader 570 which pulls the second free end under loops 5 and 6, forming a loop, as illustrated in FIGS. 17C and 17D. The threader 570 is then inserted through the newly formed loop of the second free end and under loop 6, as illustrated in FIG. 17E. The first free end is then looped around and fed through the threader 570 and pulled under loop 6 and through the loop formed by the second free end and tightened, as illustrated in FIGS. 17F-17H. The threader 570 is then placed through the newly formed loop of the first free end and under loop 6, as illustrated in FIG. 17I. The second free end is inserted through the threader which pulls it under loop 6 and through the loop formed by the first free end, as illustrated in FIGS. 17J and 17K. The threader 570 is used to pull the first free end and the second free end through respective apertures of the pusher tube 547, as illustrated in FIGS. 17L-17Q. The threader is then used to pull the first and second free ends through the central aperture of the pusher tube 547, as illustrated in FIGS. 17R and 17S.

FIG. 17T illustrates a single threader 570 being threaded through the pre-formed locking suture by going under loop 6, over loop 5, under loop 4, over loop 3 and under loops 2 and 1. In this configuration, the locking suture 537 and the LS delivery device 546 are ready to receive suture ends 532, 534. The suture ends 532, 534 are fed through the end of the threader in FIG. 17U and pulled through the locking suture in FIGS. 17V and 17W, thereby threading the suture ends 532, 534 through the locking suture.

In the configuration illustrated in FIG. 17W, the locking suture is ready to be delivered to a targeted location. Once at the target location, the target suture can be deployed by applying forces on the first and second free ends, forming the knot tethers 537B.

An advantageous aspect of the LS delivery device 546, and other delivery devices described herein, is the configuration of the apertures 547A, 547B of the pusher tube 547. The placement of these apertures causes a targeted or tailored force vector when tightening the locking suture. Rather than applying a purely proximal longitudinal force, the apertures 547A, 547B cause the suture free ends to pull radially out as well as longitudinally. This advantageously causes the locking suture to tighten on the free suture ends while preventing or limiting proximal or distal movement of the locking suture during the tightening procedure.

A benefit of the method of forming the locking suture illustrated in FIGS. 17A-17W is that it provides a way to use a single threader to interweave suture tails through the pre-formed deployable locking suture. Thus, this method may be easier and less complicated to implement than the method illustrated in FIGS. 16K-16AK.

FIGS. 18A-18K illustrate another example LS delivery device 1046 with a tensioning mechanism that includes a rack and pinion configuration. The LS delivery device includes a proximal portion 1036, a medial portion 1038, and a distal portion 1040. The proximal portion 1036 forms a handle 1035 to allow easy operation by a user. The proximal portion 1036 also includes a rack 1042 that operably couples to a pinion gear 1044 and a spring block 1048. The proximal portion 1036 also includes spring plungers 1045 that are in contact with the spring block 1048, applying a downward force on the spring block 1048 causing it to apply a downward force on the rack 1042. A lever 1043 is coupled to the pinion gear 1044 so that rotation of the lever 1043 causes the pinion gear 1044 to rotate which in turn causes the rack 1042 to move backward or forward along a longitudinal axis of the LS delivery device 1046.

Figure 18A:
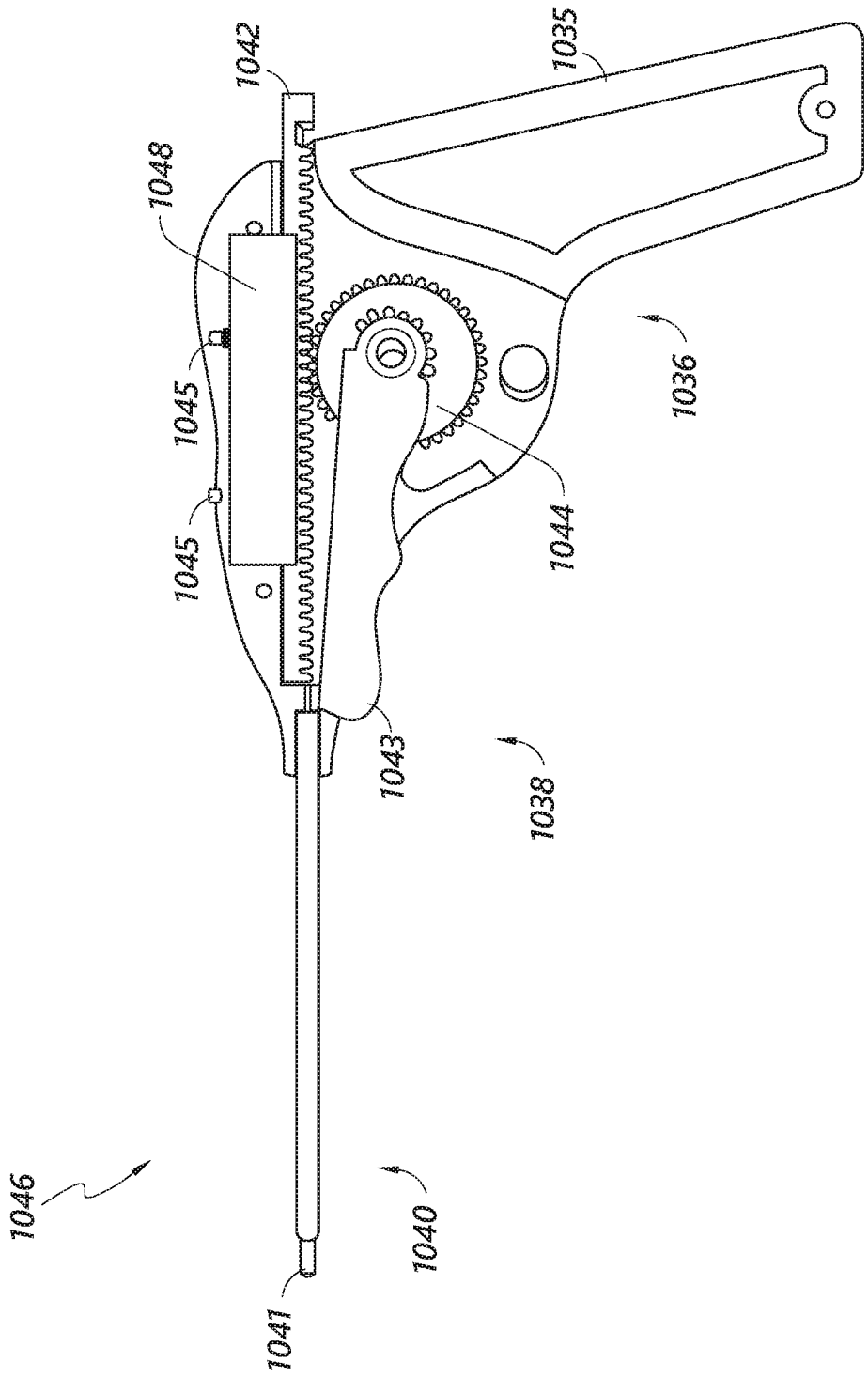
Figure 18B:
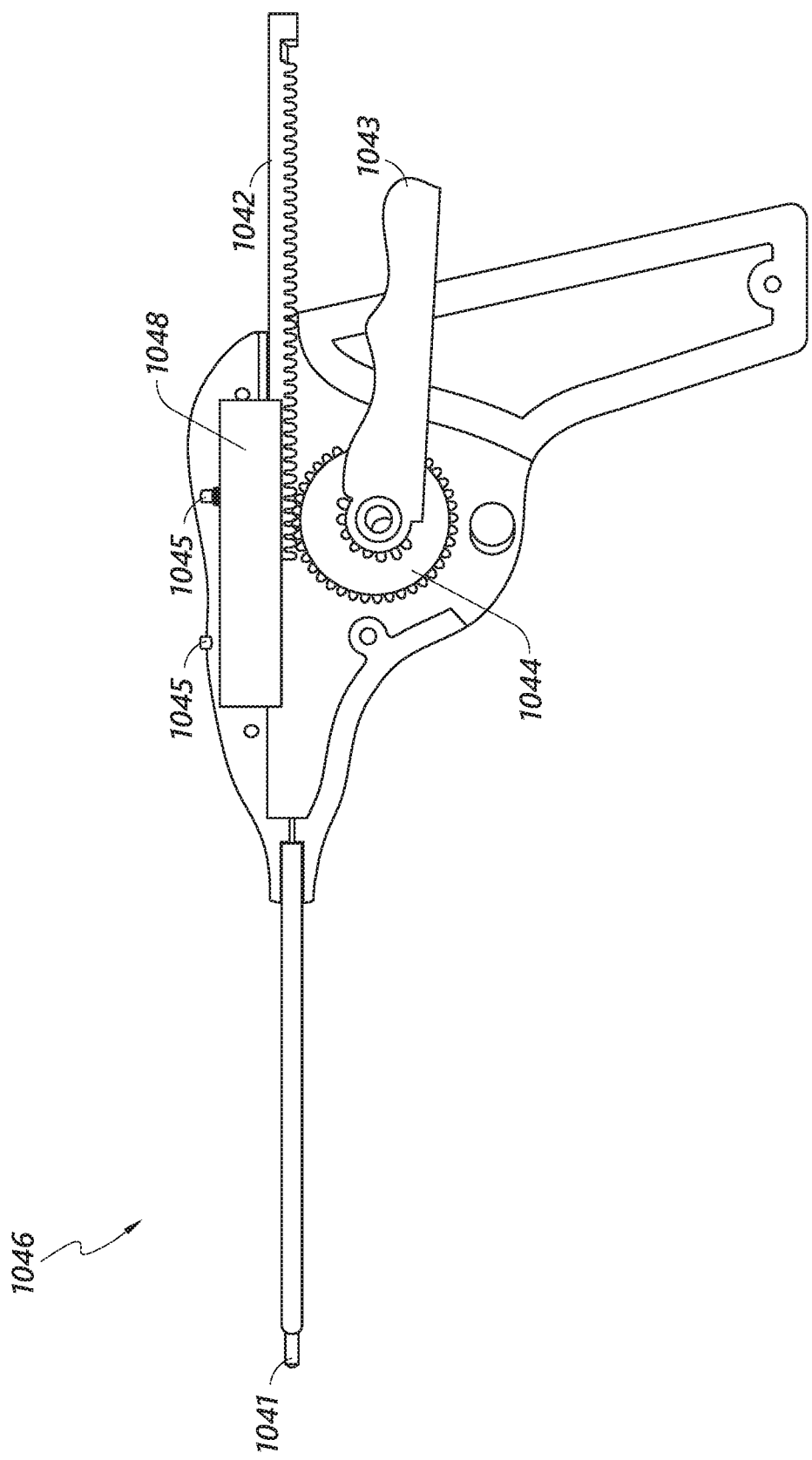
Figure 18C:
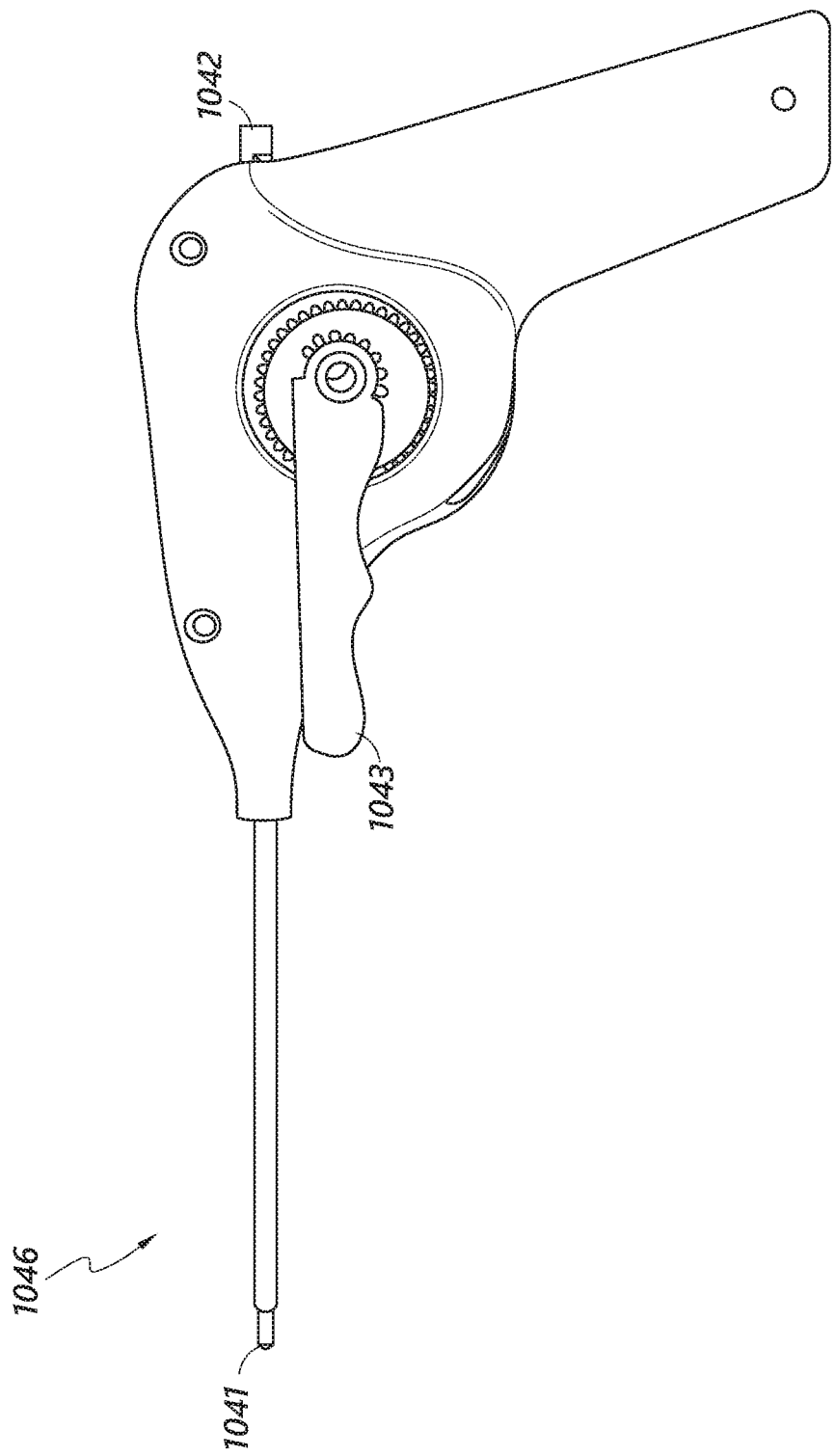
Figure 18D:
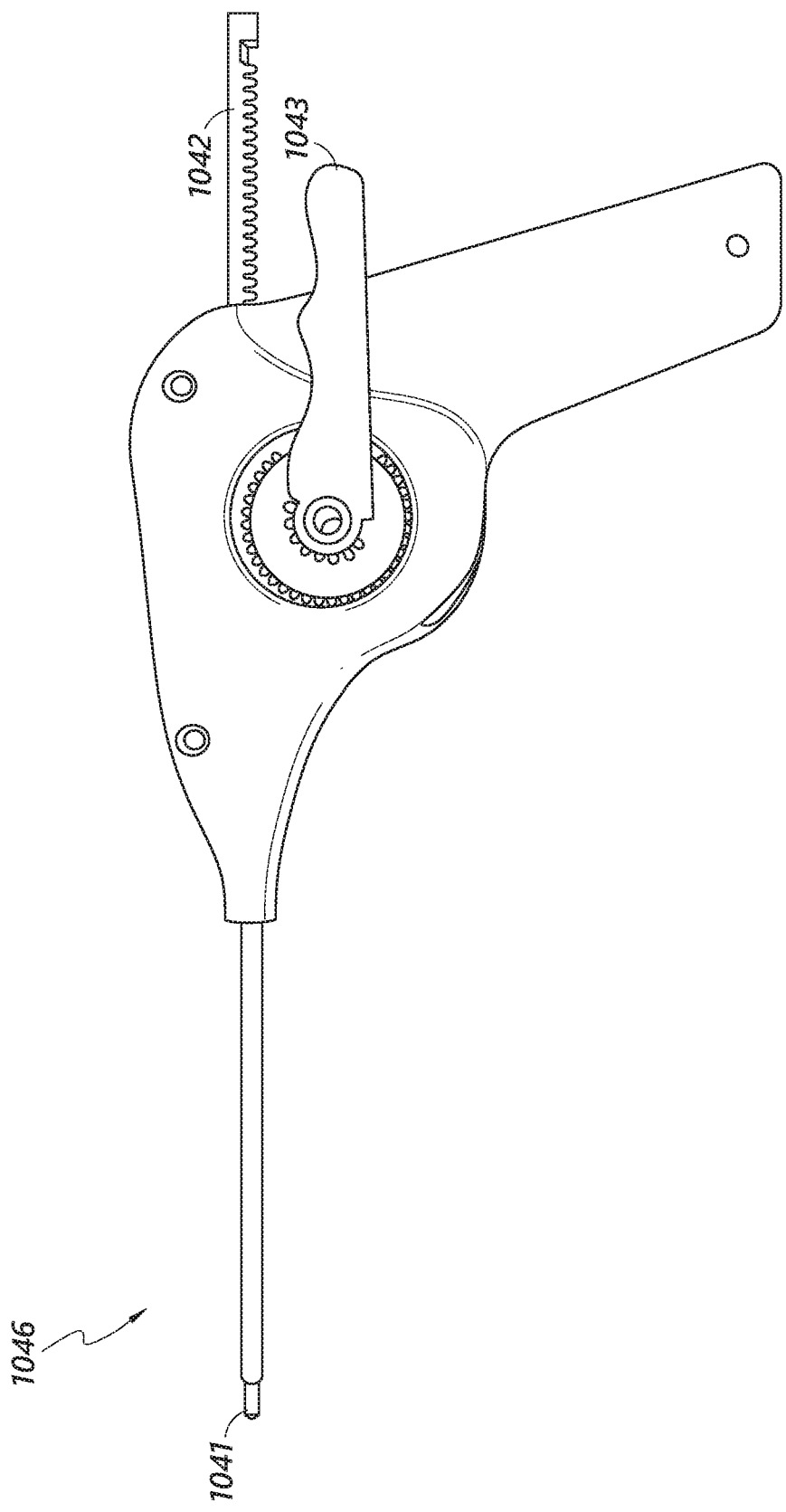

The LS delivery device 1046 includes a pre-formed knot holder 1041 (an elongate member) coupled to the housing at the medial portion 1038 of the LS delivery device 1046. Similar to the other delivery devices disclosed herein, the knot holder 1041 is configured to secure a pre-formed locking suture for delivery and to aid in transitioning the locking suture from a delivery configuration to a deployed configuration. FIGS. 18A and 18C illustrate the LS delivery device in a delivery or pre-deployment configuration and FIGS. 18B and 18D illustrate the LS delivery device in a deployed or post-deployment configuration. As can be seen in the illustrations, to transition from a pre-deployment configuration to a post-deployment configuration, the lever 1043 is rotated from the front to the back, or from pointing distally to pointing proximally. FIGS. 18A and 18B illustrate the LS delivery device 1846 with a portion of the housing removed to reveal the interactions between the lever 1043, the pinion gear 1044, the rack 1042, the spring block 1048, and the spring plungers 1045, while FIGS. 18C and 18D illustrate the same configurations but the complete, enclosed housing.

In some embodiments, the spring block 1048 and the spring plungers 1045 cooperate to limit the amount of tension applied by the rack 1042 on a tether of a locking suture. When a sufficient tension is reached on the locking suture tethers, the rack 1042 experiences an upward force caused by the interaction of the rack 1042 with the pinion gear 1044. Once this force surpasses a threshold, the spring block 1048 moves up so that the teeth of the rack 1042 disengage from the teeth of the pinion gear 1044. This can advantageously reduce the likelihood of over-tensioning the locking suture which may cause the sutures to fray or otherwise become damaged.

Figure 18E:
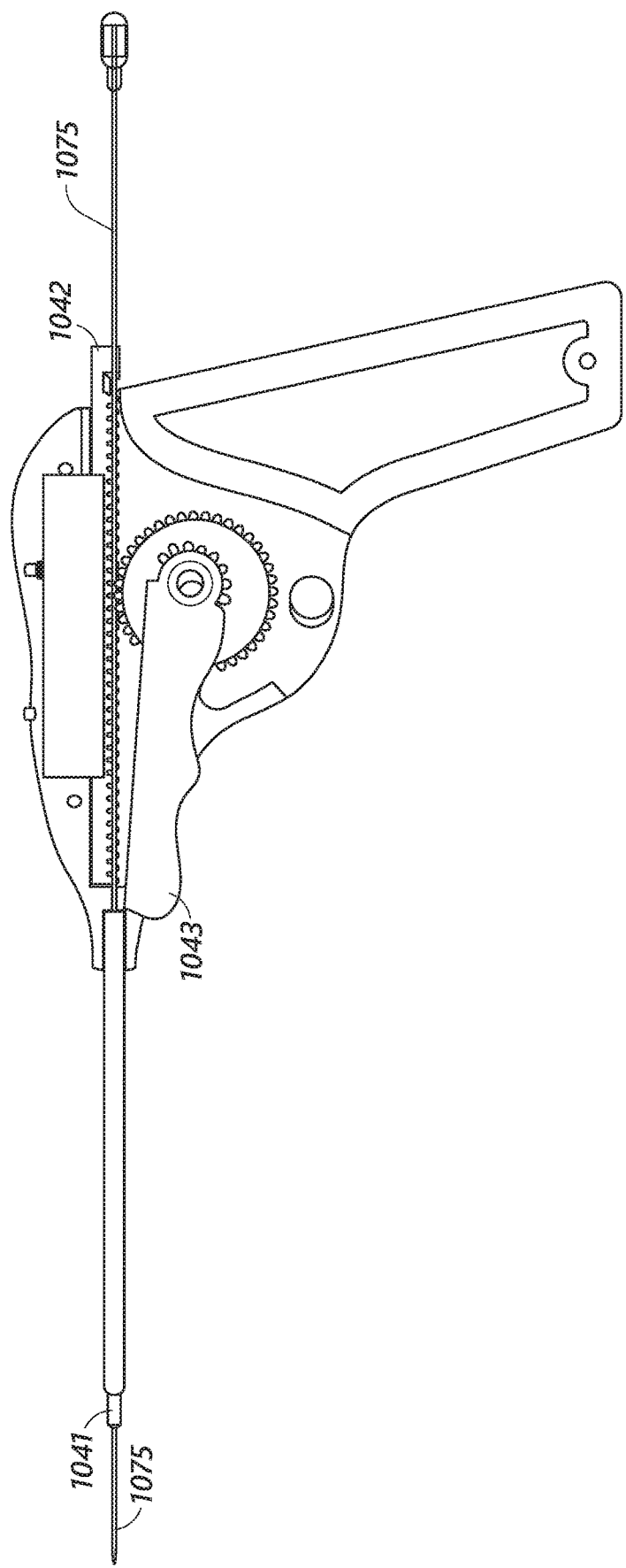

FIG. 18E illustrates that a slotted needle knot holder 1075 can be inserted through the knot holder 1041. The slotted needle 1075 can be configured to allow a locking suture to be formed thereon.

FIGS. 18F and 18G illustrate a deployable locking suture 1037 formed on the needle knot holder with a threader 1070 interweaved through the pre-formed locking suture, ready to receive suture ends. The ends 1037B of the locking suture 1037 are fed through the knot holder 1041 and tied or otherwise secured to a proximal end of the rack 1042, as illustrated in FIG. 18G.

Figure 18H:
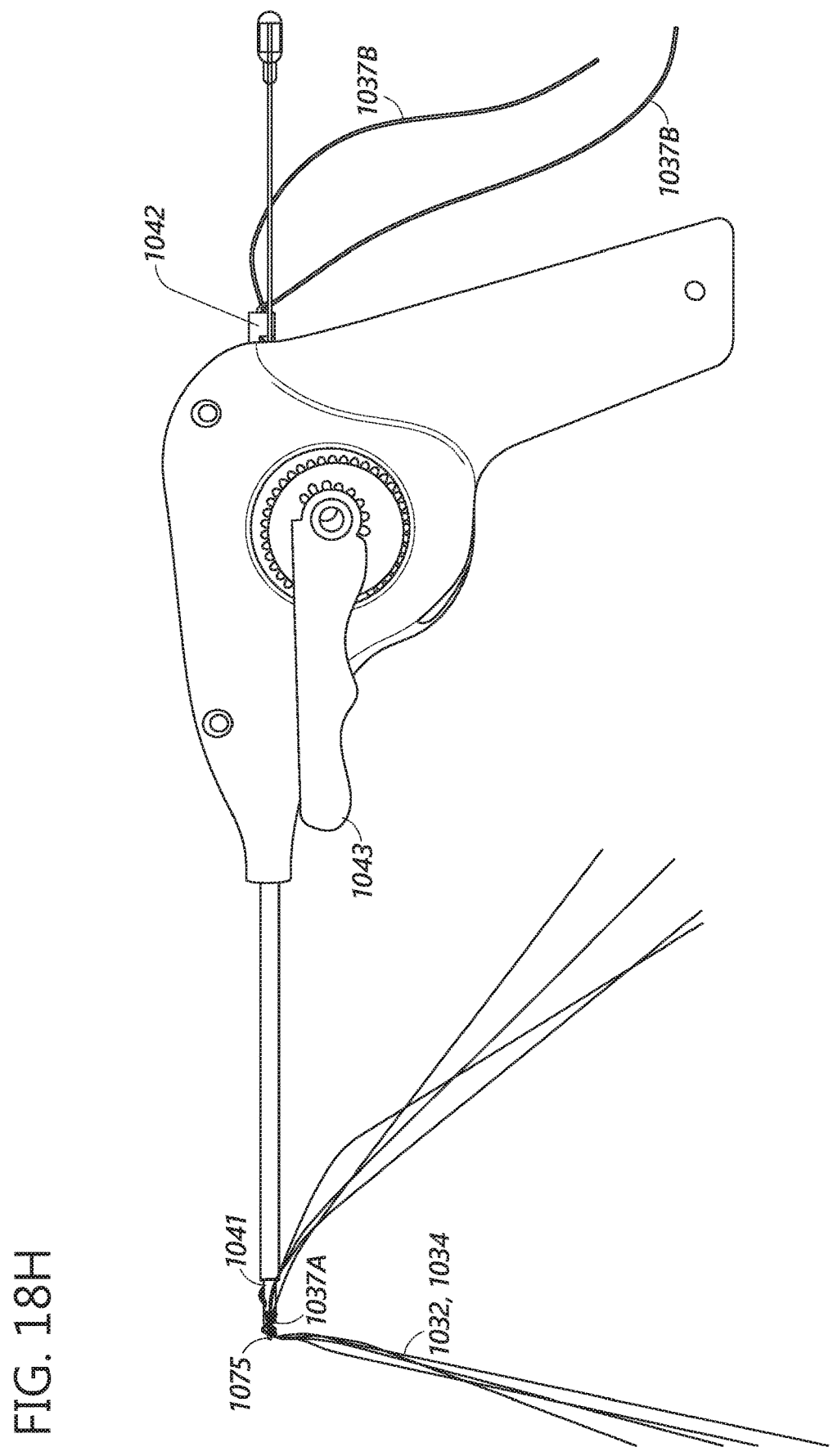

FIG. 18H illustrates the slotted needle 1075 being withdrawn after the threader 1070 has been used to interweave the sutures 1032, 1034 through the knot portion 1037A to leave the locking suture at the distal end of the knot holder 1041.

Figure 18I:
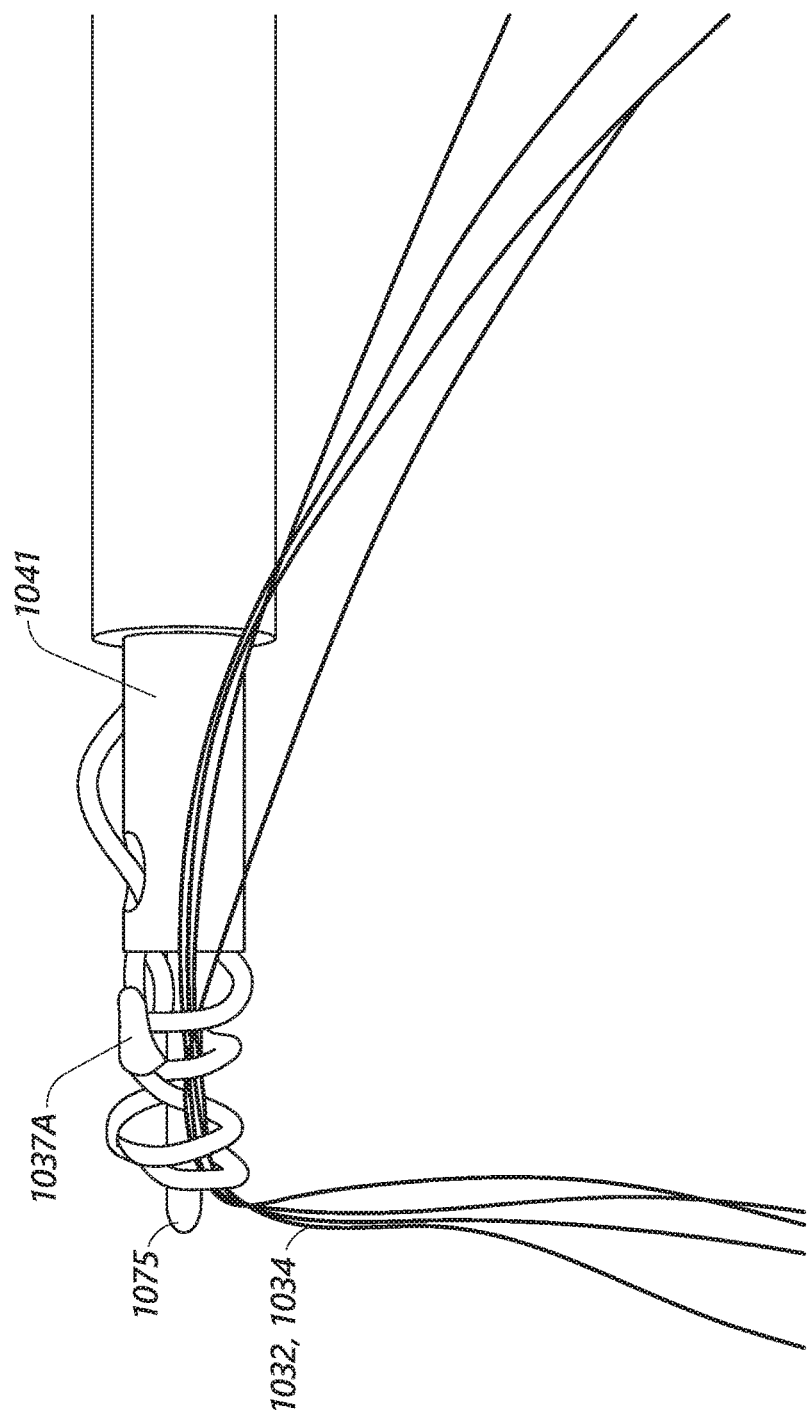
Figure 18J:
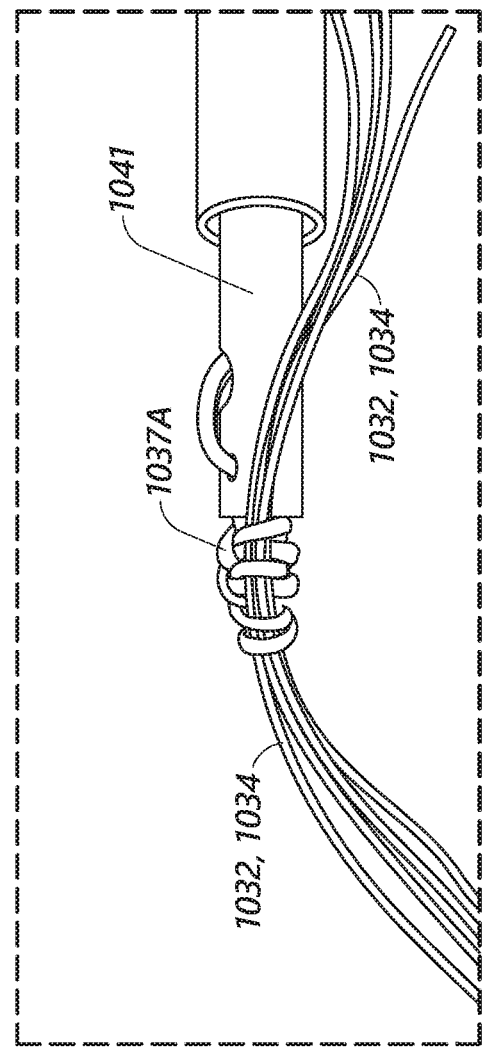

FIG. 18I illustrates the knot portion 1037A of the locking suture at the distal end of the knot holder 1041 with the sutures 1032, 1034 threaded through the knot and the slotted needle 1075 being withdrawn. FIG. 18J illustrates these same elements after the slotted needle 1075 has been completely withdrawn. Thus, the knot portion 1037A is positioned at the distal end of the knot holder 1041 prior to deployment.

FIGS. 18K and 18L illustrate the knot portion 1037A after the lever 1043 has been rotated to secure the knot 1037A. The rack 1042 is shown as protruding proximally from the proximal portion of the LS delivery device 1046 to demonstrate pulling or tensioning of the locking suture tethers 1037B. As illustrated in FIG. 18M, the knot portion 1037A has constricted and tightened around the suture ends 1032, 1034 and can be released from the knot holder 1041.

Figure 19:
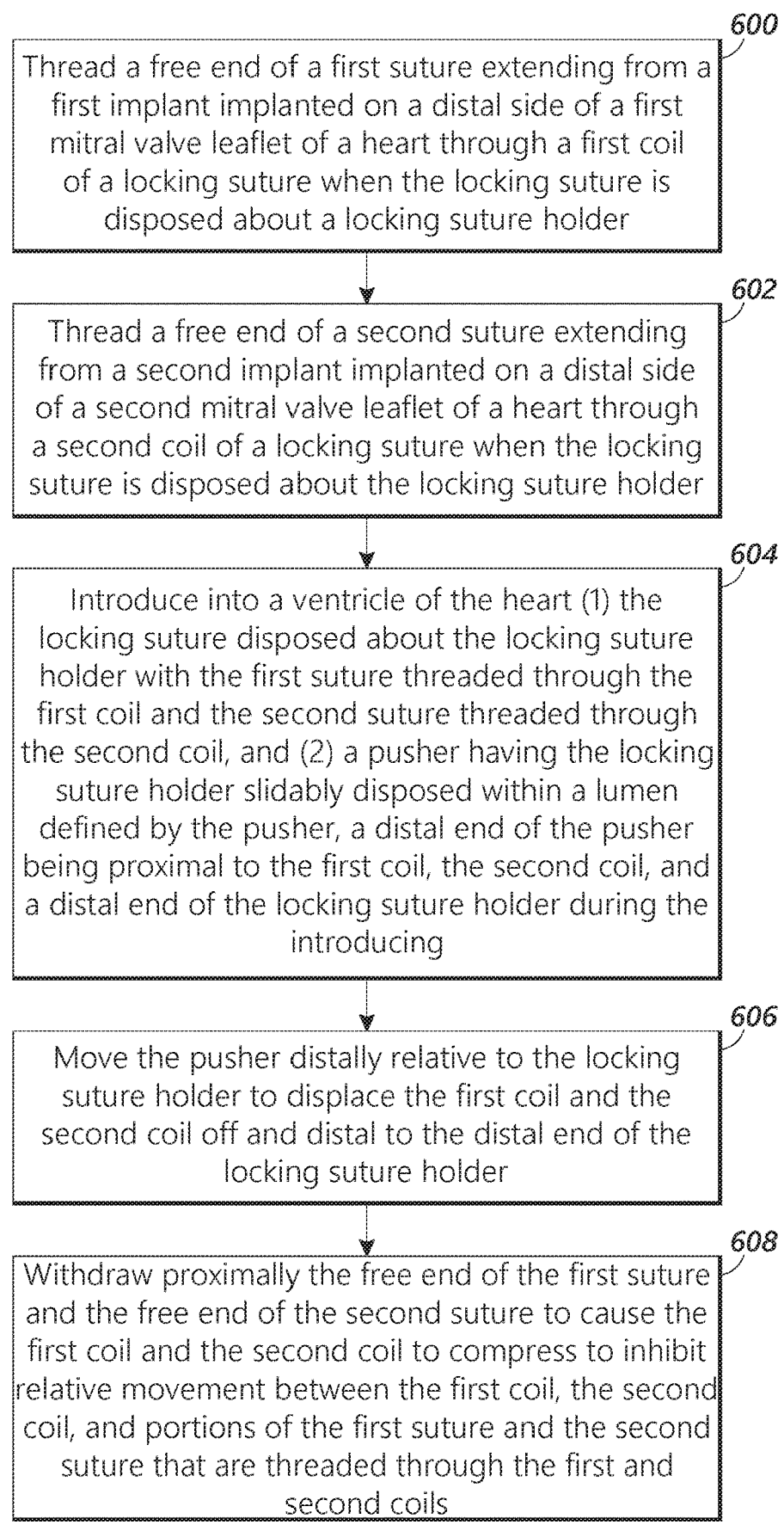
FIG. 19 illustrates a flowchart of an example method of delivering and deploying a locking suture to approximate mitral valve leaflets, according to an embodiment.

FIG. 19 is a flow chart that illustrates a method 600 of delivering and deploying a locking suture with a LS delivery device such as the LS delivery device 546, for example, to approximate mitral valve leaflets, according to an embodiment. In some embodiments, the method includes, at 600, threading a free end of a first suture extending from a first implant implanted on a distal side of a first mitral valve leaflet of a heart through a first coil of a locking suture when the locking suture is disposed about a locking suture holder. The method further includes, at 602, threading a free end of a second suture extending from a second implant implanted on a distal side of a second mitral valve leaflet of the heart through a second coil of the locking suture when the locking suture is disposed about the locking suture holder. The method further includes, at 604, introducing into a ventricle of the heart (1) the locking suture disposed about the locking suture holder with the first suture threaded through the first coil and the second suture threaded through the second coil, and (2) a pusher having the locking suture holder slidably disposed within a lumen defined by the pusher. During the introducing, a distal end of the pusher is proximal to the first coil, the second coil, and a distal end of the locking suture holder. The method further includes, at 606, moving the pusher distally relative to the locking suture holder to displace the first coil and the second coil off and distal to the distal end of the locking suture holder. The method further includes, at 608, withdrawing proximally the free end of the first suture and the free end of the second suture to cause the first coil and the second coil to compress to inhibit relative movement between the first coil, the second coil, and portions of the first suture and the second suture that are threaded through the first and second coils.

While in various embodiments described herein, methods have included forming the knot portion of the locking suture with three cow hitches, in other embodiments any suitable number of cow hitches and/or other suitable types of knot(s) could be used so long as the locking suture when deployed sufficiently secures the sutures disposed therein. In some embodiments, for example, a knot portion could be formed with less than three cow hitches (e.g., 1 or 2 cow hitches). In such embodiments, however, the gripping or securing force of the knot portion when deployed may be less than that of a knot portion formed with three cow hitches, as described above. Without sufficient gripping or securing force, the deployed locking suture may undesirably move or slip when under tension. In other embodiments, for example, more than three cow hitches could be used to form the knot portion. In such embodiments, however, additional cow hitches may increase the complexity and time required in forming the knot portion. Each additional cow hitch will require additional threading through the additional coils and may introduce additional slack or loose winds, thereby potentially reducing the effectiveness of the locking suture once deployed.

While in various embodiments described herein, methods have included delivering distally a knot portion of a locking suture in a delivery configuration to a suitable location within a target region, it should be understood that for any of these embodiments, the process of delivery (prior to deployment) is adjustable (including reversible) in real-time. In this manner, if an operator pushes or delivers the knot portion too far (e.g., identified as such under remote imaging or visualization), the operator can simply withdraw or retract proximally the LS delivery device or a suitable component thereof to withdraw or move proximally the knot portion to place the knot portion in a suitable location, and then deploy the knot portion as appropriate.

Figure 20:
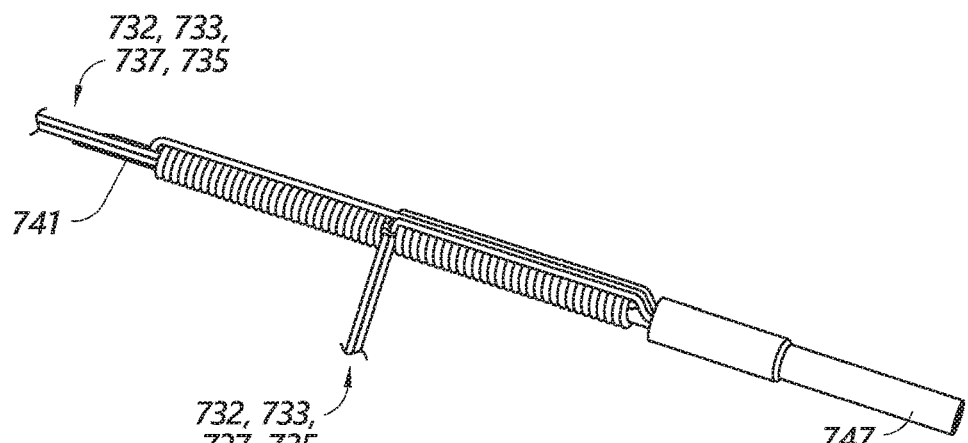
FIG. 20 illustrates a locking suture disposed about a knot holder in an elongated configuration, according to an embodiment.
Figure 21:
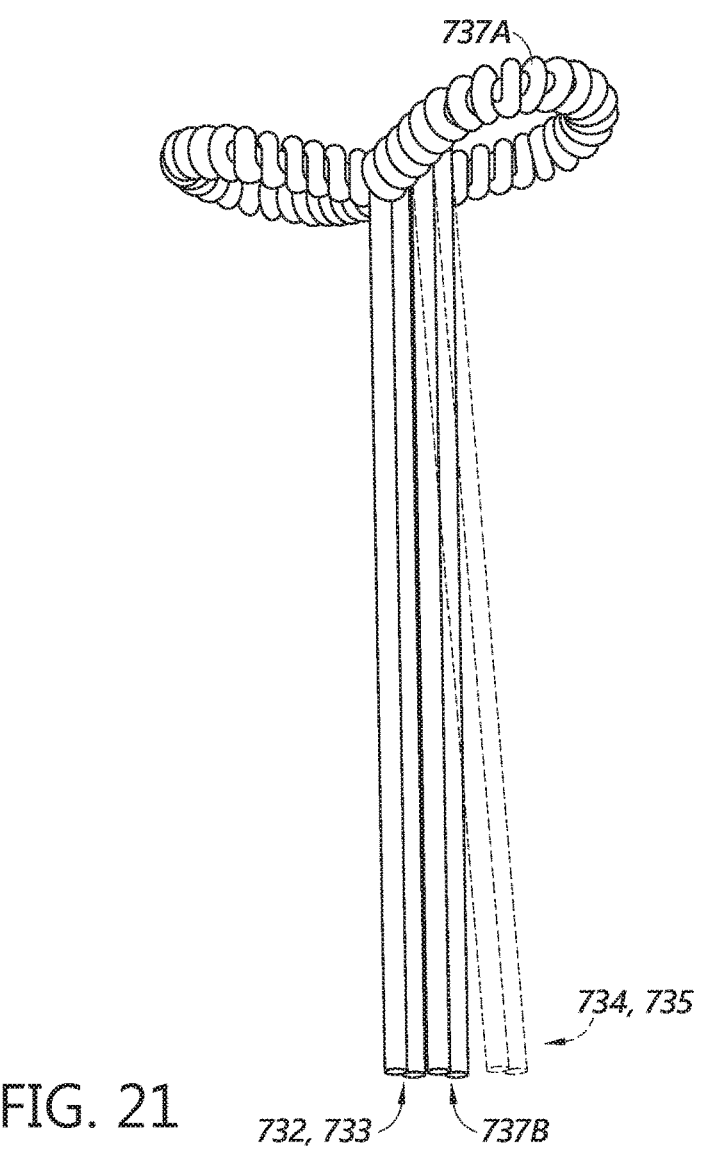
FIG. 21 illustrates the locking suture of FIG. 20 in a deployed knot configuration.

In alternative embodiments, instead of or in addition to using cow hitches, a locking suture can be in the form of one or more multi-turn coils of a suture that can be changed from an elongated configuration to a knot configuration by approximating opposite ends of the coil(s) towards each other, to form one or more loops, similar to or the same as any of the pre-formed knots or anchors described in U.S. Pat. No. 8,852,213 (the '213 patent) and/or in International Application No. WO 2017/059426, the disclosures of each of which are incorporated by reference herein in their entireties. Such a locking suture 737, for example, is shown in an elongated configuration in FIG. 20 and in a deployed, bulky knot configuration, in FIG. 21. As shown in FIG. 20, the locking suture 737 is disposed about a knot holder 741 that is slidably disposed within a lumen of a knot pusher 747. With the locking suture 737 disposed in its elongated configuration about the knot holder 741, the free ends of the suture portions 732, 733, 734, 735 (e.g., extending from implants implanted within a heart of a patient; not shown), are routed through the coils of the locking suture 737 from its distal end to a medial portion (e.g., through the portion separating the two loops formed during deployment, as described below and shown in FIG. 21). In this manner, the locking suture 737 can be deployed to change from its elongated configuration to its knot configuration, as shown in FIG. 21, by approximating opposite ends of the coils towards each other, to form two loops. For example, as described in connection with the distal anchor 140 of the '213 patent, the strands or lengths of the sutures can extend from opposite ends of the elongate coiled portion and extend through a delivery device, and then the proximal ends of the suture can be pulled proximally to cause opposite ends of the coiled portions to be pulled towards each other to form the loops. With the locking suture 737 deployed, the suture portions 732-736 can be secured to inhibit relative movement therebetween as described in connection with previous embodiments.

Although in this embodiment the suture portions are threaded through the distal end of the locking suture and out the medial portion, in other embodiments, the suture portions can be threaded in any suitable manner. For example, one or more (including all) of the suture portions can be threaded through the distal end to the proximal end of the coils, through the proximal end to the distal end of the coils, through the proximal end and out the medial portion of the coils, through the medial portion of the coils and to the distal or proximal end, and/or interlaced (e.g., in and out of) throughout the coils. In such embodiments, each free end or length of suture portion can be routed together or separately and through varying pathways. In yet further alternative embodiments, a single set of coils could be used and the suture tails or free ends can be interlaced with the locking suture in any suitable manner.

Repairing a cardiac valve (e.g., a mitral valve) by implanting a distal anchor or implant, as described herein, is often influenced by a patient's particular anatomy. When the combined length of the posterior leaflet and the anterior leaflet is significantly larger than the A-P dimension of the mitral valve, the likelihood of a successful repair is significantly higher. For example, a patient having a large posterior leaflet is desirable, as a large posterior leaflet provides a large surface of coaptation with the anterior leaflet, thereby providing a sufficient seal when the leaflets coapt, e.g., to limit regurgitation. Conversely, a patient having a small posterior leaflet will have a relatively smaller surface of coaptation. Similarly, a patient having a large anterior leaflet can help lead to a desirable and successful repair. Ultimately, the effectiveness and durability of a repair of this nature is influenced greatly by the amount of anterior and posterior leaflet tissue coapting together during systole. As another example, some patients have a relatively large valve orifice (e.g., the orifice may dilate over time due to illness), and as a result are prone to less leaflet coaptation and increased regurgitation. Ensuring sufficient coaptation is addressed by various embodiments described herein, including the following examples.

Figure 22A:
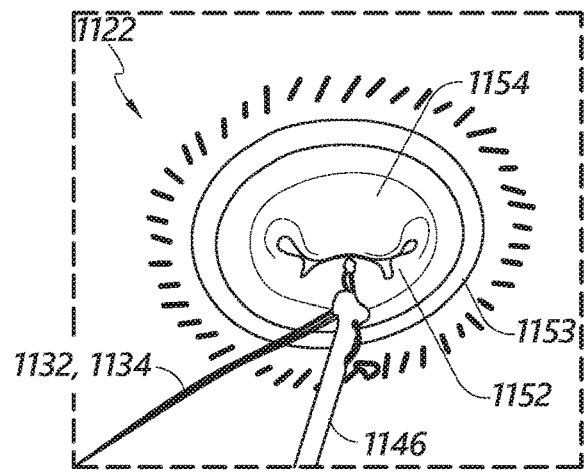
FIGS. 22A, 22B, and 22C illustrate an edge-to-edge procedure for a mitral valve using the locking sutures and delivery devices described herein.
Figure 22B:
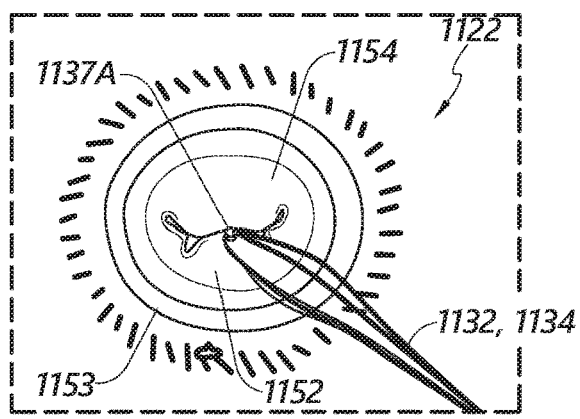
Figure 22C:
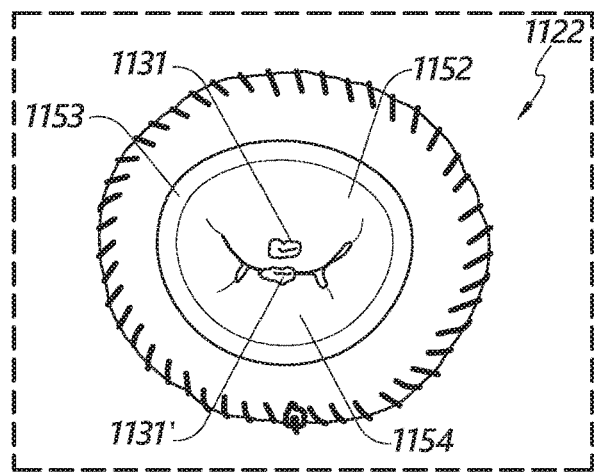

FIGS. 22A-22C illustrate an edge-to-edge procedure for a mitral valve 1122 using the locking sutures and delivery devices described herein. The mitral valve 1122 includes two leaflets, the anterior leaflet 1152 and the posterior leaflet 1154, and a diaphanous incomplete ring around the valve, called the annulus 1153. FIG. 22A illustrates the ventricular side of the mitral valve 1122. A delivery device 1146 delivers a locking suture to a targeted location along sutures 1132, 1134. FIG. 22B illustrates edge-to-edge approximation of the mitral valve leaflets 1152, 1154 with the locking suture 1137A placed at or near the tissue. FIG. 22C illustrates the atrial side of the mitral valve 1122, with distal anchors 1131, 1131' visible.

While various embodiments described above include deploying a locking suture to sutures extending from implants deployed near the free edge of mitral valve leaflets to perform an edge-to-edge or Alfieri procedure, in some implementations, the implants can be alternatively or additionally deployed in other locations to facilitate other types of cardiac repairs necessitated by various cardiac issues (e.g., small posterior leaflet, large orifice, leaflet clefts, etc.), some of which are described below.

In some embodiments, for example, the implants can be placed near the free edge of the anterior and posterior leaflets, and the cords extending therefrom can be approximated and secured together using the methods and devices described above to improve coaptation of the anterior and posterior leaflets. For example, in a patient who has a relatively large valve orifice (e.g., due to dilation of the orifice over time due to illness), and as a result is prone to less leaflet coaptation and increased regurgitation, approximating the implants can increase available leaflet surfaces for coaptation. Additionally, the secured sutures (and/or the tether portion of the locking suture) can be suitably tensioned and/or pulled towards the access site and into the ventricle of the heart, resulting in a larger surface area of coaptation, and improved coaptation between the leaflets.

Further, to promote a larger surface of coaptation, in some embodiments, implants can be deployed in the body of the leaflets and/or at or near the annulus of the anterior and posterior leaflets, and the cords extending therefrom can be secured together and pulled to move the posterior annulus towards the anterior leaflet and/or the anterior annulus towards the posterior leaflet, thereby reducing the distance between the anterior annulus and the posterior annulus, e.g., the septal-lateral distance, by about 10%-40%. Said another way, approximating the anterior annulus and the poster annulus in this manner can decrease the valve orifice, and thereby decrease, limit, or otherwise prevent undesirable regurgitation.

While various embodiments described herein have included two implants and two sets of cords, and one locking suture, in various implementations, any suitable number of implants and any suitable number of sets of cords and any suitable number of locking sutures can be delivered and deployed to approximate various portions of the heart to combat the cardiac issues described herein. For example, in some embodiments, three or more sets of cords can be approximated and secured together using one or more locking sutures to approximate two, three or more implants. In some instances, for example, the heart can be effectively re-shaped (e.g., improve orifice geometry, improve relative leaflet geometry, etc.) by strategically deploying multiple implants and securing multiple cords extending therefrom using the methods and devices described herein.

As another example, in some instances, it may be desirable to decrease a gap between a valve commissure (e.g., the edge of the valve where the leaflets come together). In such instances, a first implant can be deployed on the posterior leaflet near the commissure and a second implant can be deployed on the anterior leaflet near the commissure. With both the first implant and second implant deployed in this manner, the cords extending therefrom can be interlaced to approximate the first implant and the second implant such that the gap between the commissure is limited, decreased, or eliminated.

As another example, in some instances in which a patient has a clefted leaflet, two or more implants can be deployed on either side of the cleft. The cords extending therefrom can then be approximated and secured together to approximate the implants such that the cleft in the leaflet is limited, decreased, or eliminated.

As another example, the valve annulus and/or orifice can be optimized and/or reduced in size by deploying multiple anchors and cords extending therefrom in various locations within the heart to effectively deliver the equivalent of an additional papillary muscle or a prosthetic papillary muscle (PPM). For example, in some instances, six implants can be deployed to a mitral valve, and all the cords extending from the six implants can be approximated and secured together using a locking suture to effectively create a single anchor common to all of the cords. Deploying multiple implants and securing or approximating the cords in this manner can provide the functionality otherwise provided by a properly functioning papillary muscle.

The above-described procedures can be performed manually, e.g., by a physician, or can alternatively be performed fully or in part with robotic or machine assistance. For example, in some embodiments, a LS delivery device can be configured to deliver and deploy a locking suture automatically. Further, although not specifically described for some embodiments, in various embodiments, the heart may receive rapid pacing to minimize the relative motion of the edges of the valve leaflets during the procedures described herein (e.g., while the sutures and locking suture is being delivered and deployed).

Additional Embodiments and Terminology

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure. Various methods are described herein in connection with various flowchart steps and/or phases. It will be understood that in many cases, certain steps and/or phases may be combined together such that multiple steps and/or phases shown in the flowcharts can be performed as a single step and/or phase. Also, certain steps and/or phases can be broken into additional sub-components to be performed separately. In some instances, the order of the steps and/or phases can be rearranged and certain steps and/or phases may be omitted entirely. Also, the methods described herein are to be understood to be open-ended, such that additional steps and/or phases to those shown and described herein can also be performed.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems, and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method for using locking sutures to approximate anchor implants attached to targeted tissue, the method comprising:
    attaching two or more cords to targeted tissue, individual cords including a distal anchor implant and a suture extending proximally from the distal anchor implant;
    intertwining proximal end portions of the two or more sutures with a knot of a locking suture, the locking suture including a tether portion extending from the knot and configured to be manipulated to transition the knot from a delivery configuration to a deployed configuration;
    positioning the knot of the locking suture relative to the two or more sutures by sliding the knot along the two or more sutures to approximate portions of the targeted tissue; and
    transitioning the knot from the delivery configuration to the deployed configuration to lock the locking suture by creating a confined tortuous path for the two or more sutures through the knot of the locking suture.

2. The method of claim 1, wherein transitioning the knot to the deployed configuration does not increase proximal forces on the targeted tissue.

3. The method of claim 1, wherein the targeted tissue is within a targeted region and positioning the knot is done utilizing a locking suture device that is operated outside of the targeted region.

4. The method of claim 3, wherein the targeted region is the heart.

5. The method of claim 4 further comprising anchoring the proximal end portions of the two or more sutures.

6. The method of claim 5, wherein anchoring the proximal end portions of the two or more sutures includes securing the proximal end portions to an external wall of the heart.

7. The method of claim 1, wherein the targeted tissue includes a leaflet of a mitral valve.

8. The method of claim 1 further comprising securing the knot to a distal end of a locking suture delivery device.

9. The method of claim 8, wherein transitioning the knot to the deployed configuration includes manipulating an element of the locking suture delivery device to which the locking suture is secured.

10. The method of claim 8 further comprising applying sequential proximal forces to the proximal end portions of the two or more sutures using the locking suture delivery device.

11. The method of claim 1, wherein positioning the locking suture along the sutures of the two or more sutures results in a point of intersection that approaches the targeted tissue to change a force vector on the two or more cords attached to the targeted tissue.

12. The method of claim 1 wherein locking the locking suture includes constricting the knot to secure the knot to the two or more sutures.

13. The method of claim 1 wherein locking the locking suture inhibits relative motion between the knot and the two or more sutures in the deployed configuration.

14. The method of claim 1 wherein the knot forms multi-turn coils.

15. The method of claim 14 wherein intertwining proximal end portions of the two or more sutures with the knot includes feeding the proximal end portions of the two or more sutures through the multi-turn coils of the knot.

16. The method of claim 1 wherein, in the delivery configuration, the knot is sufficiently loose to allow the knot to slide along the two or more sutures and, in the deployed configuration, the knot is sufficiently tight to inhibit relative motion between the knot and the two or more sutures.

17. The method of claim 1 wherein, in the deployed configuration, the knot is constricted to create a tortuous path for the two or more sutures intertwined with the knot.

18. The method of claim 1 wherein transitioning the knot from the delivery configuration to the deployed configuration comprises applying a proximal force on the tether portion of the locking suture.

19. The method of claim 1 wherein the knot is in the form of braided, twisted, coiled, looped, or knotted sutures that is configured so that application of a proximal force on the tether portion causes the knot to constrict on the two or more sutures intertwined with the knot.

20. The method of claim 1 further comprising receiving feedback from a visualization system, the feedback including an approximation of the targeted tissue.

* * * * *